United States Patent
Ermantraut et al.

(10) Patent No.: US 9,580,745 B2
(45) Date of Patent: Feb. 28, 2017

(54) METHOD AND DEVICE FOR THE DETECTION OF MOLECULAR INTERACTIONS

(71) Applicant: CLONDIAG GMBH, Jena (DE)

(72) Inventors: Eugen Ermantraut, Jena (DE); Ralf Bickel, Jena (DE); Torsten Schulz, Jena (DE); Thomas Ullrich, Jena (DE)

(73) Assignee: CLONDIAG GMBH, Jena (DE)

( * ) Notice: Subject to any disclaimer, the term of this patent is extended or adjusted under 35 U.S.C. 154(b) by 0 days.

(21) Appl. No.: 14/474,274

(22) Filed: Sep. 1, 2014

(65) Prior Publication Data

US 2015/0284785 A1 Oct. 8, 2015

Related U.S. Application Data

(62) Division of application No. 12/092,643, filed as application No. PCT/EP2006/068155 on Nov. 6, 2006, now Pat. No. 8,828,741.

(30) Foreign Application Priority Data

Nov. 4, 2005 (DE) .................. 10 2005 052 713

(51) Int. Cl.
*G01N 21/64* (2006.01)
*C12Q 1/68* (2006.01)
(Continued)

(52) U.S. Cl.
CPC .......... *C12Q 1/6837* (2013.01); *B01L 3/5027* (2013.01); *B01L 3/502746* (2013.01); *G01N 21/6452* (2013.01); *G01N 21/6458* (2013.01); *B01L 7/52* (2013.01); *B01L 7/525* (2013.01); *B01L 2200/027* (2013.01); *B01L 2300/044* (2013.01); *B01L 2300/0636* (2013.01); *B01L 2300/0654* (2013.01);
(Continued)

(58) Field of Classification Search
CPC ................. C12Q 1/6837; B01L 3/5027; B01L 3/502746; B01L 7/525; B01L 7/52; G01N 21/6452; G01N 21/6458; B01F 11/0045
See application file for complete search history.

(56) References Cited

U.S. PATENT DOCUMENTS

| 5,795,748 A | 8/1998 | Cottingham |
| 5,910,288 A * | 6/1999 | Schembri ............ B01F 11/0045 422/551 |

(Continued)

FOREIGN PATENT DOCUMENTS

| WO | WO 00/05336 | 2/2000 |
| WO | WO 01/27327 | 4/2001 |

*Primary Examiner* — Melanie Y Brown
(74) *Attorney, Agent, or Firm* — Steptoe & Johnson LLP

(57) ABSTRACT

The present invention relates to devices and methods for the detection of analytes. In particular, the invention relates to methods for the qualitative and/or quantitative detection of analytes, comprising a microarray on a substrate, onto which probe molecules are immobilized on array elements, said microarray being disposed on a first surface of the device; and a detection chamber formed between the first surface including the microarray disposed thereon and a second surface, wherein the distance between the microarray and the second surface is variable, and wherein the second surface has a displacement structure.

8 Claims, 35 Drawing Sheets

(51) Int. Cl.
 *B01L 3/00* (2006.01)
 *B01L 7/00* (2006.01)
(52) U.S. Cl.
 CPC ............... *B01L 2300/0816* (2013.01); *B01L 2300/0819* (2013.01); *B01L 2300/0864* (2013.01); *B01L 2300/0877* (2013.01); *B01L 2300/1827* (2013.01); *B01L 2300/1838* (2013.01); *B01L 2400/0481* (2013.01)

(56) References Cited

U.S. PATENT DOCUMENTS

| | | |
|---|---|---|
| 6,569,674 B1 | 5/2003 | McGarry et al. |
| 6,881,541 B2 | 4/2005 | Petersen et al. |
| 6,953,551 B2 | 10/2005 | Chen et al. |
| 7,070,921 B2 | 7/2006 | Huang et al. |
| 7,332,328 B2 | 2/2008 | Webb |
| 8,916,348 B2 | 12/2014 | Bickel et al. |
| 2001/0012612 A1 | 8/2001 | Petersen et al. |
| 2001/0053334 A1 | 12/2001 | Chen et al. |
| 2002/0034766 A1 | 3/2002 | Huang et al. |
| 2002/0177157 A1 | 11/2002 | Luo et al. |
| 2003/0107946 A1* | 6/2003 | Cosby ................ B01F 11/0045 366/127 |
| 2003/0124029 A1 | 7/2003 | Webb |
| 2004/0018523 A1 | 1/2004 | Hawkins et al. |
| 2004/0137607 A1* | 7/2004 | Tanaami ........... B01L 3/502715 435/287.2 |
| 2005/0019898 A1 | 1/2005 | Adey et al. |
| 2005/0238534 A1* | 10/2005 | Chu ....................... G01N 1/312 435/6.11 |
| 2006/0094108 A1* | 5/2006 | Yoder .................... B01L 3/508 435/287.2 |
| 2007/0254372 A1 | 11/2007 | Bickel et al. |

* cited by examiner (1) Standard DNA ladder
(2) Test reactor 1
(3) Test reactor 2

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Cy3 modified

<400> SEQUENCE: 1
tgaggctggg aarctgaca                                                      19

<210> SEQ ID NO 2
<211> LENGTH: 19
<212> TYPE: DNA
```

<213> ORGANISM: Artificial Sequence
<220> FEATURE:
<223> OTHER INFORMATION: Description of Artificial Sequence: Synthetic primer
<220> FEATURE:
<223> OTHER INFORMATION: 3'-NH2 modified

<400> SEQUENCE: 2
gggygaggay aacgaaatc                                              19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gggygaggay aacgaaatc                                              19

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: 5'-Cy3 modified

<400> SEQUENCE: 4
ccctgaatgc ggctaat                                                17

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: 3'-NH2 modified

<400> SEQUENCE: 5
attgtcacca taagcagcc                                              19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
attgtcacca taagcagcc                                              19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: 5'-Cy3 modified

<400> SEQUENCE: 7
ctcgtaaaat ggcccctcc                                                    19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 3'-NH2 modified

<400> SEQUENCE: 8
cggccgtgtg acactatcg                                                    19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggccgtgtg acactatcg                                                    19

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-Cy3 modified

<400> SEQUENCE: 10
cgctctcgta aatgcttccc t                                                 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 3'-NH2 modified

<400> SEQUENCE: 11
tctacccaca acagacccac g                                                 21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tctacccaca acagacccac g                                                 21

<210> SEQ ID NO 13
<211> LENGTH: 14
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<223> OTHER INFORMATION: 5'-Cy3 modified

<400> SEQUENCE: 13
tcgcgtgctg cggc                                                       14

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 3'-NH2 modified

<400> SEQUENCE: 14
cggcatggcc cgtctat                                                    17

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cggcatggcc cgtctat                                                    17

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NH2 modified

<400> SEQUENCE: 16
tgttgggcaa ccaccgcact g                                               21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agagtttgat cctggctcag                                                 20

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
taccgtcacc ataaggcttc gtcccta                                         27
```

METHOD AND DEVICE FOR THE DETECTION OF MOLECULAR INTERACTIONS

SEQUENCE LISTING

The instant application contains a Sequence Listing which has been submitted electronically in ASCII format and is hereby incorporated by reference in its entirety. Said ASCII copy, created on Jun. 18, 2015, is named 15111.0101D1_SL.txt and is 4,888 bytes in size.

RELATED APPLICATIONS

This application claims the benefit of German patent application DE 10 2005 052 713, which is incorporated herein by reference in its entirety. The present application further relates to German patent application DE 10 2005 052 752 and to the International Patent Application entitled "Device and method for the detection of particles", filed on Nov. 6, 2006 (Maiwald reference number C 7759), both of which applications are incorporated herein by reference in their entireties.

FIELD OF THE INVENTION

The invention relates to devices and methods for the determination of analytes (e.g., target molecules) by, for example, the determination of interactions (e.g., specific interactions) between probe molecules and the target molecules.

BACKGROUND

Biomedical tests are often based on the detection of an interaction between a molecule, which is present in known amount and position (the molecular probe), and an unknown molecule to be detected or unknown molecules to be detected (the molecular target molecules). In current tests, probes are laid out in the form of a substance library on supports, the so-called microarrays or chips, so that a sample can be analyzed simultaneously at various probes in a parallel manner (see, for example, J. Lockhart, E. A. Winzeler, Genomics, gene expression and DNA arrays; Nature 2000, 405, 827-836). The probes are herein usually immobilized on a suitable matrix, as is for example described in WO 00/12575 (see, for example, U.S. Pat. No. 5,412,087, WO 98/36827), or synthetically produced (see, for example, U.S. Pat. No. 5,143,854) in a predetermined manner for the preparation of the microarrays.

A typical example for the use of microarrays in biological test methods is the detection of microorganisms in samples in biomedical diagnostics. Herein, it is taken advantage of the fact that the genes for ribosomal RNA (rRNA) are dispersed ubiquitously and have sequence portions, which are characteristic for the respective species. These species-characteristic sequences are applied onto a microarray in the form of single-stranded DNA oligonucleotides. The target DNA molecules to be examined are first isolated from the sample to be examined and are equipped with markers, for example fluorescent markers. Subsequently, the labeled target DNA molecules are incubated in a solution with the probes fixed on the microarray; nonspecifically occurring interactions are removed by means of corresponding washing steps and specific interactions are detected by means of fluorescence-optical evaluation. In this manner, it is possible to detect, for example, several microorganisms simultaneously in one sample by means of one single test. In this test method, the number of detectable microorganisms theoretically only depends on the number of the specific probes, which have been applied onto the microarray.

A variety of methods and technical systems, some of which are also commercially available, are described for the detection of molecular interactions with the aid of microarrays or probe arrays on solid surfaces.

Classical systems for the detection of molecular interactions are based on the comparison of the fluorescence intensities of spectrally excited target molecules labeled with fluorophores. Fluorescence is the capacity of particular molecules to emit their own light when excited by light of a particular wavelength. Herein, a characteristic absorption and emission behavior ensues. In analysis, a proportional increase of the fluorescence signal is assumed as labeled molecule density on the functionalized surface increases, for example, due to increasing efficiency of the molecular interaction between target and probe molecules.

In particular, quantitative detection of fluorescence signals is performed by means of modified methods of fluorescence microscopy. Herein, the light having the absorption wavelength is separated from the light having the emission wavelength by means of filters or dichroites and the measured signal is imaged on suitable detectors, like for example two-dimensional CCD arrays, by means of optical elements like objectives and lenses. In general, analysis is performed by means of digital image processing.

Hitherto known technical solutions vary regarding their optical setup and the components used. Problems and limitations can result from the signal noise (the background), which is basically determined by effects like bleaching and quenching of the dyes used, autofluorescence of the media, assembling elements, and optical components as well as by dispersions, reflections, and secondary light sources within the optical setup.

This leads to great technical effort for the setup of highly sensitive fluorescence detectors for the qualitative and quantitative comparison of probe arrays. In particular, for screening with medium and high throughputs, specially adapted detection systems are necessary, which exhibit a certain degree of automation.

For optimizing standard epifluorescence setups for reading out molecular arrays, CCD-based detectors are known, which implement the excitation of the fluorophores in the dark field by means of incident light or transmitted light for the discrimination of optical effects like dispersion and reflections (see, for example, C. E. Hooper et al., Quantitative Photon Imaging in the Life Sciences Using Intensified CCD Cameras, Journal of Bioluminescence and Chemiluminescence (1990), p. 337-344). Herein, imaging of the arrays is performed either in exposure or by means of rasterizing using higher resolution optics. The use of multispectral light sources allows a comparatively easy access to different fluorophores by means of using different excitation filters (combinations).

Further methods for the quantitative detection of fluorescence signals are based on confocal fluorescence microscopy. Confocal scanning systems, as for example described in U.S. Pat. No. 5,304,810, are based on the selection of fluorescence signals along the optical axis by means of two pinholes.

Currently, analyses based on probe arrays are normally read out fluorescence-optically (see, for example, A. Marshall and J. Hodgson, DNA Chips: An array of possibilities, Nature Biotechnology, 16, 1998, 27-31; G. Ramsay, DNA Chips: State of the Art, Nature Biotechnology, 16, January 1998, 40-44).

A variety of in particular, confocal systems are known, which are suitable for the detection of small-scale integrated substance libraries in array format, which are installed in fluidic chambers (see, for example, U.S. Pat. Nos. 5,324,633, 6,027,880, 5,585,639, WO 00/12759).

However, the above-described methods and systems can only be adapted in a very limited way for the detection of large-scale integrated molecular arrays, which are, in particular, installed in fluidic systems, in particular due to the dispersions, reflections, and optical aberrations occurring therein. Furthermore, in such large-scale integrated arrays, great demands are made concerning the spatial resolution, which could, however, up to now technically not be implemented.

Thus, there is a need for highly integrated arrays that allow for the quantitative and/or qualitative detection of the interaction between probes and targets with comparatively low technical effort and with great precision.

The increase in selectivity and the access to alternative components motivate the establishment of alternative imaging technologies such as fluorescence polarization and time-resolved fluorescence for assays bound to solid bodies. The effect of twisting the polarization axis by means of fluorophores excited in a polarized manner is used for quantification in microtiter format. Furthermore, there are approaches to set up inexpensive systems having a high throughput (HTS systems) by means of using correspondingly modified polymer foils as polarization filters (see I. Gryczcynski et al., Polarisation sensing with visual detection, Anal. Chem. 1999, 71, 1241-1251).

More recent developments utilize the fluorescence of inorganic materials, like lanthanides (M. Kwiatowski et al., Solid-phase synthesis of chelate-labelled oligonucleotides: application in triple-color ligase-mediated gene analysis, Nucleic Acids Research, 1994, 22, 13) and quantum dots (M. P. Bruchez et. al., Semiconductor nanocrystals as fluorescent biological labels, Science 1998, 281, 2013).

Optical setups for the detection of samples labeled by means of gold beads and their visualization by means of silver amplification are described in the International Patent Application WO 00/72018.

A method for the qualitative and/or quantitative detection of targets in a sample by means of molecular interactions between probes and targets on probe arrays was provided in WO 02/02810, wherein the time-dependent behavior of precipitation formation at the array elements is detected in the form of signal intensities, i.e. dynamic measurement is performed. On the basis of a curve function describing precipitation formation as a function of time, a value quantifying the interaction between probe and target on an array element and therefore the amount of targets bound is assigned to each array element.

In many tests in biomedical diagnostics, the problem occurs that the target molecules are at first not present in an amount sufficient for detection and therefore often have to be amplified from the sample prior to the actual test procedure. Typically, the amplification of DNA molecules is performed by means of the polymerase chain reaction (PCR). For the amplification of RNA, the RNA molecules have to be converted to correspondingly complementary DNA (cDNA) via reverse transcription. This cDNA can then also be amplified by means of PCR. PCR is a standard laboratory method (like, for example, in Sambrook et al. (2001) Molecular Cloning: A laboratory manual, 3rd edition, Cold Spring Harbor, N.Y., Cold Spring Harbor Laboratory Press).

The amplification of DNA by means of PCR is comparatively fast, allows a high sample throughput in small setup volumes by means of miniaturized methods, and is efficient in operation due to automation.

However, a characterization of nucleic acids by means of mere amplification is not possible. It is rather necessary to use analysis methods like nucleic acid sequence determinations, hybridization, and/or electrophoretic separation and isolation methods for the characterization of the PCR products subsequently to the amplification.

In general, devices and methods for the amplification of nucleic acids and their detection should be designed in such a way that as few interventions of the practitioner as possible are required. The advantages of methods allowing for multiplication of nucleic acids and their detection, and in the course of which the practitioner has to intervene only to a minimal extent, are self-evident. On the one hand, contaminations are avoided. On the other hand, the reproducibility of such methods is significantly increased, as they are accessible to automation. This may also be important with respect to the pharmaceutical approval of diagnostic methods.

At present, there are a multiplicity of methods for the amplification of nucleic acids and their detection, wherein first the target material is amplified by means of PCR amplification and subsequently the identity or the genetic state of the target sequences is determined by means of hybridization against a probe array. In general, amplification of the nucleic acid molecules or the target molecules to be detected is necessary in order to have at one's disposal amounts sufficient for a qualitative and quantitative detection within the scope of the hybridization.

Both PCR amplification of nucleic acids and their detection by hybridization are subject to several elementary problems. This applies in the same manner to methods combining PCR amplification of nucleic acids and their detection by means of hybridization.

If detectable markers, for example fluorescence labeled primers, are introduced into the nucleic acid molecules to be detected or target molecules to be detected in a method, which combines PCR amplification and detection by hybridization, a washing step is usually performed before the actual detection. Such a washing step provides for the removal of the non-converted primers, which are present in great excess compared to the amplification product, as well as of such nucleotides comprising a fluorescent label, which do not participate in the detection reaction and do not specifically hybridize with the nucleic acid probes of the microarray, respectively. In this manner, the high signal background caused by these molecules is to be reduced. However, such an additional procedure step considerably slows down the detection method. Furthermore, the detectable signal is considerably reduced also for those nucleic acids to be detected, which specifically hybridize with the nucleic acid probes of the microarray. The latter is largely based on the fact that no equilibrium between the targets bound by hybridization and targets in solution does exist anymore after the washing step. Nucleic acids, which had already hybridized with the nucleic acid probes located on the array, are detached from the binding site by washing and are therefore washed away together with the dissolved molecules. Washing or rinsing steps are typically intended to perform so that the wash or rinse liquid remains in contact with the nucleic acids for a period of time less than the average detachment time of the nucleic acids already hybridized.

Thus, there is a need for highly integrated arrays that allow for the quantitative and/or qualitative detection of the interaction between probes and targets with comparatively low technical effort and with great precision.

Furthermore, there is a need for devices which allow for the performance of PCR and analysis reaction, such as a hybridization reaction, in one reaction space.

In particular, it is a problem underlying embodiments of the present invention to provide methods and devices, respectively, by which molecular interactions between probes and targets on probe arrays can be detected in a quantitative and/or qualitative manner with great precision and high sensitivity as well as in an easy-to-do and cost-efficient manner.

Furthermore, it is a problem underlying embodiments of the present invention to provide methods and devices, respectively, for the amplification and for the qualitative and quantitative detection of nucleic acids, by which the interventions of the practitioner in the detection procedure can be minimized.

It is a further problem underlying embodiments of the present invention to provide methods and devices, respectively, for the qualitative and quantitative detection of target molecules, by which a high signal-to-noise ratio in the detection of interactions on the microarray is ensured without impairing the interaction between the target molecules and the probe molecules on the array.

It is a further problem underlying embodiments of the present invention to provide devices and methods, respectively, by which a high dynamic resolution in detection reaction is achieved, i.e. the detection of weak probe/target interactions is ensured aside of strong signals.

Furthermore, it is a problem underlying embodiments of the present invention to provide devices and methods, respectively, which allow an almost simultaneous amplification and characterization of nucleic acids at a high throughput rate.

SUMMARY OF THE INVENTION

In a first aspect, the present invention relates to a device for the qualitative and/or quantitative detection of analytes, the device comprising:
 a microarray on a substrate, onto which probe molecules are immobilized on array elements, said microarray being disposed on a first surface of the device; and
 a detection chamber formed between the first surface including the microarray disposed thereon and a second surface,
 wherein the distance between the microarray and the second surface is variable, and wherein the second surface has a displacement structure.

The displacement structure may be configured to displace at least some or substantially all of a mixture from between the microarray and the second surface or between the first and second surfaces. The mixture may comprise a liquid, a complex comprising an analyte (which is hereinafter also designated as a target molecule) and an optical label and/or the optical label in an uncomplexed state with respect to the analyte, the optical label in the uncomplexed state having a greater mobility than the complex.

In some embodiments, the detection chamber is configured as a capillary gap. In other embodiments, the detection chamber comprises at least two sub-chambers.

In a further embodiment of the invention, the displacement structure is located on the side of the second surface that is facing the microarray. In this embodiment, the displacement structure may be located on the side of the second surface that is facing the microarray in such a way that, when the distance between the microarray and the second surface is reduced, it is located at least partially opposite the surface of the microarray.

In exemplary embodiments, the displacement structure is formed of an elastically deformable material, which may be optically transparent and have low autofluorescence at a wavelength of light used to excite fluorescence from molecules of the array.

Preferred displacement structures of the invention are made of an elastically deformable material that is particularly preferably optically transparent and not autofluorescent.

In one embodiment, the first surface is planar and the displacement structure is formed in that the second surface is non-planar.

In a further embodiment, the displacement structure, when viewed from the first surface, has a convex shape. E.g., the displacement structure is configured as bulge of the second surface.

The second surface may be made of an optically transparent material such as glass.

In a further embodiment, the reaction chamber formed between the first and the second surface is laterally limited by elastic seals. The first surface may also be elastically deformable, at least in the surface area beneath the microarray.

In a further embodiment, the first surface, at least in the region beneath the microarray, is configured in such a way that the microarray can be guided relatively to the second surface in such a way that the distance between the microarray and the second surface is variable.

The inventive device may further comprise at least one actuator or means by which the microarray can be guided relatively to the second surface, preferably by applying pressure and/or traction to the first surface via the means. Such an actuator may be configured to reduce a distance between the first and second surfaces or between the microarray and the second surface and displace at least some or substantially all of the mixture from between the first and second surfaces or between the microarray and the second surface.

In a second aspect, the present invention relates to a method for the qualitative and/or quantitative detection of analytes, the method comprising the following steps:
 introducing a sample containing analytes into a detection chamber of a device as defined in the invention;
 detecting an interaction between the analytes and probe molecules immobilized on the substrate.

In one embodiment of the invention, for detection the distance between the microarray and the second surface is reduced. In this embodiment, said distance may be reduced to such an extent that the sample solution or mixture to be analyzed is substantially displaced from the reaction chamber. The mixture may comprise a liquid, a complex comprising an analyte (which is hereinafter also designated as a target molecule) and an optical label and/or the optical label in an uncomplexed state with respect to the analyte, the optical label in the uncomplexed state having a greater mobility than the complex.

In some embodiments, the target molecules are provided with a detectable label such as a fluorescence label. The probe molecules and/or target molecules are preferably biopolymers, in particular nucleic acids and/or nucleic acid analogs.

In a further embodiment, the target molecules to be analyzed are amplified in the reaction chamber by means of a cyclic amplification reaction, wherein the detection may be performed during the cyclic amplification reaction after completion of one or more cycles and/or after the overall completion of the cyclic amplification reaction.

Further, in a third aspect, the invention relates to a method for the qualitative and/or quantitative detection of molecular interactions between probe and target molecules, the method comprising the following steps:

introducing a sample containing target molecules into a reaction chamber having a microarray, said microarray comprising a substrate onto which probe molecules are immobilized on array elements; and detecting an interaction between the target molecules and the probe molecules immobilized on the substrate, wherein between introducing the sample containing target molecules into the reaction chamber and the detection no replacement of solutions in the reaction chamber and/or removal of solutions from the reaction chamber takes place.

In a fourth aspect, the invention relates to a method comprising:

forming a mixture comprising (a) a liquid, (b) a complex comprising an analyte and an optical label and (c) the optical label in an uncomplexed state with respect to the analyte, the optical label in the uncomplexed state having a greater mobility than the complex, with at least some of the mixture positioned between first and second surfaces, reducing a distance separating the first and second surfaces and displacing at least some of the mixture from between the first and second surfaces, optically detecting optical label remaining between the first and second surfaces, and determining the presence of the analyte based on the detected optical label;

wherein, during at least a portion of the step of reducing the distance separating the first and second surfaces, the distance separating the surfaces changes as a function of position along the first surface.

In one embodiment of this method, the first surface is planar and the second surface is non-planar.

In a further embodiment, when viewed from the first surface, the second surface is convex.

In a further embodiment, the forming a mixture comprises forming a mixture comprising multiple different complexes, each of the complexes is immobilized with respect to the first surface, the immobilized complexes define an array, and, during the step of reducing a distance, a distance between a central portion of the array and the second surface is less than a distance between a peripheral portion of the array and the second surface.

In a further embodiment, a shape defined by a distance variation between the first and second surfaces extending from a central portion of the array to peripheral portions of the array is arcuate.

In a further embodiment, the complex is immobilized with respect to a particle disposed between the first and second surfaces.

In a further embodiment, the particle is a cell.

In a fifth aspect, the invention relates to a device, comprising:

a detection zone defined at least in part between first and second surfaces, the detection zone being configured to accommodate a mixture comprising (a) a liquid, (b) a complex comprising an analyte and an optical label and (c) the optical label in an uncomplexed state with respect to the analyte, the optical label in the uncomplexed state having a greater mobility than the complex, an actuator configured to reduce a distance between the first and second surfaces and displace at least some of the mixture from between the first and second surfaces, and a detector configured to determine the presence of the optical label in the complexed state with the at least some mixture in the displaced state;

wherein the actuator and first and second surfaces are configured so that, when the actuator reduces a distance between the first and second surfaces, the distance between the first and second surfaces changes as a function of position along the first surface.

In one embodiment of this device, the actuator is configured to displace at least some of the mixture without first introducing a liquid free of the optical label to between the first and second surfaces.

BRIEF DESCRIPTION OF THE DRAWINGS

FIGS. 25A-23B illustrate the process of introducing a sample into a reaction cartridge having an integrated filling unit.

DETAILED DESCRIPTION OF THE INVENTION

Figure 1:
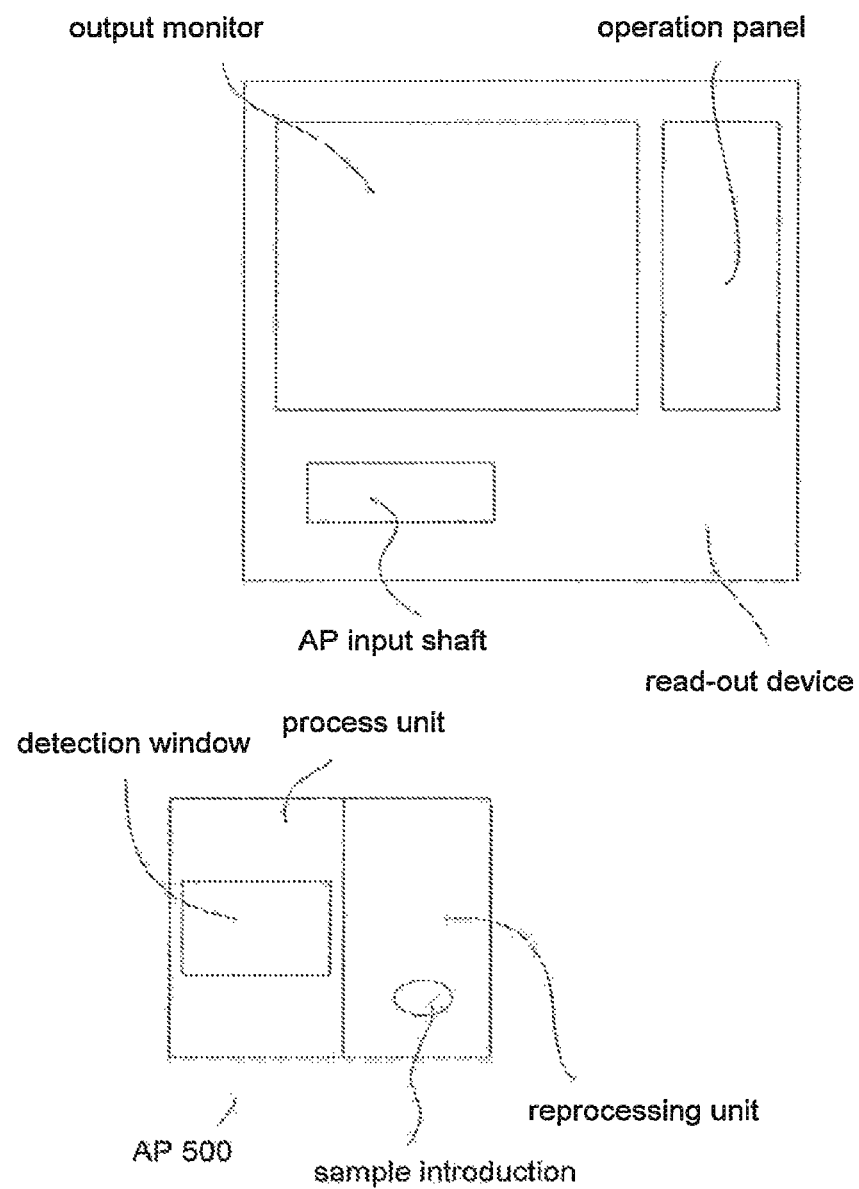
FIG. 1 is a schematic illustration of a device according to the invention.

According to the present invention, methods for the qualitative and/or quantitative detection of analytes are provided, wherein the replacement and/or the removal of solutions, i.e. in particular washing or rinsing steps, can be omitted. In one embodiment, analytes are detected by detecting molecular interactions between probe molecules and analytes. Analytes are hereinafter also referred to as target molecules.

Such methods according to the present invention may comprise the following steps:
a) introducing a sample containing target molecules into a reaction chamber having a microarray, said microarray comprising a substrate onto which probe molecules are immobilized on array elements; and
b) detecting an interaction between the target molecules and the probe molecules immobilized on the substrate,
wherein after introducing the sample containing target molecules and prior to and during the detection no replacement of solutions in the reaction chamber and/or removal of solutions from the reaction chamber takes place.

Furthermore, within the scope of the present invention devices are provided that are suitable for performing such methods.

In one embodiment, a device for the qualitative and/or quantitative detection of analytes is provided, comprising:
a) a microarray on a substrate, onto which probe molecules are immobilized on array elements, said microarray being disposed on a first surface of the device; and
b) a detection chamber formed between the first surface including the microarray disposed thereon and a second surface,
wherein the distance between the microarray and the second surface is variable, and wherein the second surface has a displacement structure.

The variability of the distance between the microarray and the second surface, which usually represents the detection surface of the inventive device, may allow for a significant reduction or the complete prevention of a signal background that is caused by labeled target molecules having no specific affinity for the probe molecules of the microarray and thus do not interact with them.

In one embodiment, the second surface has a displacement structure located on the surface that is facing the microarray. This displacement structure may cause a substantially complete displacement of the solution from the reaction chamber if the first and the second surface approach each other.

The invention further relates to a method for the qualitative and/or quantitative detection of analytes or target molecules, which comprises the following steps:
a) introducing a sample comprising target molecules into a detection chamber of an inventive device as described above;
b) detecting an interaction between the target molecules and the probe molecules immobilized on the substrate.

The methods and devices according to the present invention for the detection of target molecules are configured in such a way, that as few interventions of the practitioner in the reaction chamber as possible are required for performing the detection method and, optionally, an amplification of the target molecules. This has an advantage that contaminations can be avoided. Furthermore, the reproducibility of the methods according to the present invention is considerably increased compared to conventional methods, as the inventive method is accessible to automation due to the minimization of external interventions. The above-mentioned advantages may play an important role in terms of the approval of diagnostic methods.

For the description of the present invention, inter alia the following definitions are used:

Within the scope of the present invention, a probe or a probe molecule or a molecular probe is understood to denote a molecule, which is used for detecting other molecules by means of a particular characteristic binding behavior or a particular reactivity. As for the probes arranged on the array, any type of molecule that can be coupled to solid surfaces and that show a specific affinity can be used. In a preferred embodiment, such molecules are biopolymers, in particular biopolymers from the classes of peptides, proteins, antigens, antibodies, carbohydrates, nucleic acids, and/or analogs thereof and/or copolymers of the above-mentioned biopolymers. Particularly preferred probes are nucleic acids and/or nucleic acid analogs.

In some embodiments, nucleic acid molecules having a defined and known sequence, which are used for the detection of target molecules in hybridization methods, are referred to as probe. Both DNA and RNA molecules can be used as nucleic acids. For example, the nucleic acid probes or oligonucleotide probes can be oligonucleotides having a length of about 10 to about 100 bases, about 15 to about 50 bases, or about 20 to about 30 bases. Typically, according to the present invention, the probes are single-stranded nucleic acid molecules or molecules of nucleic acid analogs, preferably single-stranded DNA molecules or RNA molecules having at least one sequence region, which is complementary to a sequence region of the target molecules. Depending on detection method and use, the probes can be immobilized on a solid support substrate, e.g. in form of a microarray. Furthermore, depending on the detection method, they can be labeled radioactively or non-radioactively, so that they are detectable by means of detection methods conventional in the state of the art.

Within the scope of the present invention, an analyte or a target or a target molecule is understood to denote a molecule to be detected by means of a molecular probe. In a preferred embodiment of the present invention, the targets to be detected are nucleic acids. In an analogous manner, the probe array according to the invention can be used for the detection of peptide-probe interactions, protein-probe interactions, carbohydrate-probe interactions, antibody-probe interactions etc.

If the targets according to the present invention are nucleic acids or nucleic acid molecules, which are detected by means of a hybridization against probes located on a probe array, said target molecules normally comprise sequences of a length of 40 to 10,000 bases, 60 to 2,000 bases, 60 to 1,000 bases, 60 to 500 bases or 60 to 150 bases. Optionally, their sequence comprises the sequences of primers as well as the sequence regions of the template, which are defined by the primers. In particular, the target molecules can be single-stranded or double-stranded nucleic acid molecules, one or both strands of which are labeled radioactively or non-radioactively, so that they are detectable by means of a detection method conventional in the state of the art.

According to the present invention, a target sequence denotes the sequence region of the target, which is detected by means of hybridization with the probe. According to the present invention, this is also referred to as said region being addressed by the probe.

Within the scope of the present invention, a substance library is understood to denote a multiplicity of different molecules, e.g. at least two to 1,000,000 different molecules, or at least 10 to 10,000 different molecules, or between 100 to 1,000 different molecules. In special embodiments, a substance library can also comprise only at least 50 or less or at least 30,000 different molecules. In some embodiments, the substance library is arranged as an array on a support within the reaction chamber of an inventive device.

Within the scope of the present invention, a probe array is understood to denote an array of molecular probes or a substance library on a support, wherein the position of each probe is determined separately. Typically, the array comprises defined sites or predetermined regions, so-called array elements, which are particularly preferably arranged in a specific pattern, wherein each array element typically comprises only one species of probes. The arrangement of the molecules or probes on the support can be generated by means of covalent or non-covalent interactions. Therefore, the probes are arranged on the side of the support that is facing the reaction chamber. A position within the arrangement, i.e. within the array, is usually referred to as spot.

Within the scope of the present invention, an array element or a predetermined region or a spot or an array spot is understood to denote an area on a surface, which is determined for the deposition of a molecular probe, the entirety of all occupied array elements being the probe array.

Within the scope of the present invention, a support element or a support or a substance library support or a substrate is understood to denote a solid body, onto which the probe array is located. The support, which is usually denoted a substrate or a matrix, can be, for example, an object slide or a wafer or ceramic materials. In a specific embodiment, the probes may also be immobilized on the first surface, preferably in a portion of the first surface.

The entirety of molecules deposited on a substrate in form of an array and of the substance library deposited on a substrate or the detection surface in form of an array and the support or substrate, respectively, is often also denoted "chip", "microarray", "DNA chip" or "probe array".

Within the scope of the present invention, a detection surface (plane) is understood to denote the second surface of the inventive device. In some embodiments, during detection the probes deposited on the microarray are substantially located in the detection plane, in particular due to the fact that the distance between microarray and second surface is reduced to about zero.

A displacement structure is denoted to be a structure, e.g. configured as a bulge of the second surface, that is located, at least partially, in the area of the second surface, which is located opposite to the microarray and arranged on the side of the second surface that is facing the microarray. The displacement structure may be configured to displace at least some or substantially all of the mixture from between the microarray and the second surface or between the first and second surfaces. The mixture may comprise a liquid, a complex comprising an analyte (which is hereinafter also designated as a target molecule) and an optical label and/or the optical label in an uncomplexed state with respect to the analyte, the optical label in the uncomplexed state having a greater mobility than the complex.

The displacer may be configured to substantially displace the (fluorescent) solution between the detection surface (second surface) and the first surface. In embodiments described below without having a displacement structure, a problem may occasionally arise that remnants of fluorescent solution remain between the two surfaces, thus causing the background noise mentioned above.

This can be avoided by employing a displacement structure, which may be configured as a bulge of the second surface.

Numerous materials can be used for displacement structures, with elastic or soft and ductile materials being preferred. In some embodiments, said materials are optically transparent and not autofluorescent, respectively, so that they do not adversely interfere with detection. Suitable materials may be, for example, silicone rubbers or silicone elastomers, "classic" rubbers, polyurethanes, acrylics, acrylates, and TPE.

Particularly preferred are two-component platinum-crosslinking silicone rubbers, such as PDMS. These are optically transparent, not autofluorescent and biologically inert.

Likewise, a liquid, which cannot be mixed with the fluorescent analyte solution or cannot be dissolved in the fluorescent analyte solution, for example silicone oil, may be employed. For example, a silicone rubber (such as Dow Corning Sylgard 184); which does not necessarily be cured, may be employed. These materials are preferably not autofluorescent.

The softer the material employed, the better it compensates for unevennesses present in the surface and for the potential roughness of a surface of the microarray, respectively. If liquid materials are used, they may wet the surface in order to allow an optimal displacement of the fluorescent solution.

The displacement structure, which may be configured as bulge of the second surface in direction to the first surface, i.e. into the detection chamber, typically has an outer shape, which allows for displacing liquid from the reaction chamber and/or from the surface of the microarray in an as efficient manner as possible. Thus, the geometric shape of the displacement structure, when viewed from the first surface may be convex. As a matter of course, planar, rectangular, or round shapes may be employed as well. In the compressed state, the displacement structure may, for example, cover the entire microarray or only parts thereof. Convex displacement structures may only contact one point of the opposite surface when the reaction chamber is compressed, and, as compression continues, may ensure a plane covering, wherein the liquid is laterally displaced from the reaction chamber or from the surface of the microarray. Geometric shapes achieving similar goals are also suitable.

The displacer may be glued on, dripped on, or deposited and fixed by a suitable means. Other methods, however, are not excluded. For instance, the displacement structure may be configured as one element together with the second surface and thus be manufactured from one piece.

Figure 32:
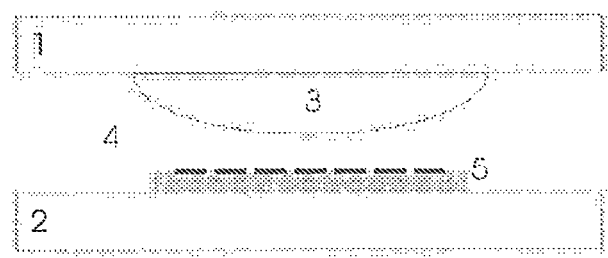
FIG. 32 is a schematic view of a reaction chamber according to the invention comprising a displacement structure located on the second surface.

The principle of a displacement structure is exemplarily depicted in FIG. 32.

Within the scope of the present invention, a chamber body is understood to denote the one or more substrates forming the reaction chamber. Usually, the substance library support or the chip is part of the chamber body, wherein the substance library support can be made of a different material than the rest of the chamber body.

Within the scope of the present invention, a chamber or detection chamber or detection zone is understood to denote the space formed between first surface and second surface or detection surface, e.g. between microarray and second surface. The detection chamber may be configured in form of a variable capillary gap. The detection chamber may also be referred to as a detection and/or reaction chamber, a reaction chamber, or a reaction space. The detection chamber can be laterally limited by side walls, which can, for example, be implemented as elastic seals. The probes immobilized on the microarray are located on the side facing the interior of the reaction chamber. The base area of the detection chamber is defined by the first surface or the second surface of the array. The distance between second surface or detection surface and the surface of the substrate or of the microarray is referred to as thickness of the reaction space or of the reaction chamber or of the capillary gap, respectively. Within the scope of the present invention, a detection chamber usually has a small thickness, such as a thickness of at most 1 cm, at most 5 mm, at most 3 mm or at most 1 mm.

Within the scope of the present invention, the distance between the microarray and the second surface is understood to denote the distance between the surface of the microarray substrate, i.e. of the side of the microarray facing the chamber, and the side of the second surface facing the chamber. If the distance between microarray and second surface is about zero, this means that the surface of the substrate rests evenly on the second surface.

Within the scope of the present invention, a capillary gap is understood to denote a detection chamber, which can be filled by means of capillary forces acting between the microarray and the second surface. Usually, a capillary gap has a small thickness, for example of at most 1 mm, preferably of at most 750 µm, and particularly preferably of at most 500 µm. Furthermore, according to the present invention, a thickness of the capillary gap in the range of 10 µm to 300 µm, of 15 µm to 200 or of 25 µm to 150 µm is preferred. In special embodiments of the present invention, the capillary gap has a thickness of 50 µm, 60 µm, 70 µm, 80 µm or 90 µm. Within the scope of the present invention, the detection chamber or reaction chamber will not be referred to as a capillary gap anymore, if the detection chamber or the reaction chamber has a thickness of more than 2 mm.

Within the scope of the present invention, a cartridge or reaction cartridge is understood to denote a unit consisting of the detection chamber with a chamber body and a corresponding casing.

Within the scope of the present invention, a confocal fluorescence detection system is understood to denote a fluorescence detection system, wherein the object is illuminated in the focal plane of the objective by means of a point light source. Herein, point light source, object and point light detector are located on exactly optically conjugated planes. Examples for confocal systems are described in A. Diaspro, Confocal and 2-photon-microscopy: Foundations, Applications and Advances, Wiley-Liss, 2002.

Within the scope of the present invention, a fluorescence optical system imaging the entire volume of the reaction chamber is understood to denote a non-confocal fluorescence detection system, i.e. a fluorescence detection system, wherein the illumination by means of a point light source is not limited to the object. Such a fluorescence detection system therefore has no focal limitation.

Conventional arrays or microarrays within the scope of the present invention comprise about 50 to 10,000 or about 150 to 2,000 different species of probe molecules on a, typically square, surface of 1 mm to 4 mm×1 mm to 4 mm, e.g. of 2 mm×2 mm, for example. In further embodiments within the scope of the present invention, microarrays comprise about 50 to about 80,000, about 100 to about 65,000, or about 1,000 to about 10,000 different species of probe molecules on a surface of several $mm^2$ to several $cm^2$, e.g. about 1 $mm^2$ to 10 $cm^2$, or 2 $mm^2$ to 1 $cm^2$, or about 4 $mm^2$ to 6.25 $mm^2$. For example, a conventional microarray has 100 to 65,000 different species of probe molecules on a surface of 2 mm×2 mm.

Within the scope of the present invention, a label or a marker is understood to denote a detectable unit, for example a fluorophore or an anchor group, to which a detectable unit can be coupled.

Within the scope of the present invention, a duplication or amplification reaction comprises typically 10 to 50 or more amplification cycles, e.g. about 25 to 45 cycles, or about 40 cycles. Within the scope of the present invention, a cyclic amplification reaction is preferably a polymerase chain reaction (PCR).

Within the scope of the present invention, an amplification cycle denotes a single amplification step of the cyclic amplification reaction. An amplification step of the PCR is also referred to as PCR cycle.

Within the scope of the present invention, an amplification product denotes a product resulting from the duplication or the copying or the amplification of the nucleic acid molecules to be amplified by means of the cyclic amplification reaction, preferably by means of the PCR. A nucleic acid molecule amplified by means of PCR is also referred to as PCR product.

Within the scope of the present invention, the denaturation temperature is understood to denote the temperature at which double-stranded DNA is separated in the amplification cycle. Usually, the denaturation temperature, in particular in a PCR, is higher than 90° C., e.g. about 95° C.

Within the scope of the present invention, the annealing temperature is understood to denote the temperature at which the primers hybridize to the nucleic acid to be detected. Usually, the annealing temperature, in particular in a PCR, lies in a range of 50° C. to 65° C. and e.g. is about 60° C.

Within the scope of the present invention, the chain extension temperature or extension temperature is understood to denote the temperature at which the nucleic acid is synthesized by means of insertion of the monomer components. Usually, the extension temperature, in particular in a PCR, lies within a range of about 68° C. to about 75° C. and e.g. is about 72° C.

Within the scope of the present invention, an oligonucleotide primer or primer denotes an oligonucleotide, which binds or hybridizes the DNA to be detected, also referred to as target DNA, wherein the synthesis of the complementary strand of the DNA to be detected in a cyclic amplification reaction starts from the binding site. In particular, primer denotes a short DNA or RNA oligonucleotide having preferably about 12 to 30 bases, which is complementary to a portion of a larger DNA or RNA molecule and has a free 3-OH group at its 3'-end. Due to said free 3'OH group, the primer can serve as substrate for any optional DNA or RNA polymerases, which synthesize nucleotides to the primer in 5'-3'-direction. Herein, the sequence of the newly synthesized nucleotides is predetermined by that sequence of the template hybridized with the primer, which lies beyond the free 3'OH group of the primer. Primers of conventional length comprise between 12 and 50 nucleotides, e.g. between 15 and 30 nucleotides.

A double-stranded nucleic acid molecule or a nucleic acid strand serving as template for the synthesis of complementary nucleic acid strands is usually referred to as template or template strand.

Within the scope of the present invention, a molecular interaction or an interaction is understood to denote a specific, covalent or non-covalent bond between a target molecule and an immobilized probe molecule. In one embodiment of the present invention, the interaction between probe and target molecules is a hybridization.

The formation of double-stranded nucleic acid molecules or duplex molecules from complementary single-stranded nucleic acid molecules is referred to as hybridization. Herein, the association preferably always occurs in pairs of A and T or G and C. Within the scope of a hybridization, for example DNA-DNA duplexes, DNA-RNA duplexes, or RNA-RNA duplexes can be formed. By means of a hybridization, duplexes with nucleic acid analogs can also be formed, like for example DNA-PNA duplexes, RNA-PNA duplexes, DNA-LNA duplexes, and RNA-LNA duplexes. Hybridization experiments are usually used for detecting the sequence complementarity and therefore the identity of two different nucleic acid molecules.

Within the scope of the present invention, processing is understood to denote purification, concentration, labeling, amplification, interaction, hybridization, and/or washing and rinsing steps as well as further method steps performed when detecting targets by using substance libraries. Detection itself does not fall under the term processing.

Within the scope of the present invention, a sample or sample solution or solution or mixture is a liquid to be analyzed, which in particular contains the target molecules to be detected and, optionally, to be amplified. Furthermore, beside conventional additives such as buffers, such a solution may inter alia also contain substances required for performing amplification reactions, like primers.

Within the scope of the present invention, a replacement of solutions in the reaction chamber from the reaction chamber refers, in particular, to rinsing or washing steps. The replacement of solutions serves, for example, for removing molecules labeled with detectable markers, which do not specifically interact with probes on the microarray, by replacing the sample solution with a non-labeled solution after the interaction has occurred. Molecules not specifically interacting with probes on the microarray are, for example, primers labeled with a detectable marker, which have not been converted during the amplification reaction, or target molecules labeled with a detectable marker, which do not have a complementary probe on the array, which specifically interacts with said target molecule.

Within the scope of the present invention, a removal of solutions from the reaction chamber is understood to denote steps, by means of which molecules labeled with detectable markers, which do not specifically interact with probes, are removed from the reaction chamber. Molecules not specifically interacting with probes arc, for example, primers labeled with a detectable marker, which have not been converted during the amplification reaction, or target molecules labeled with a detectable marker, which do not have a complementary probe on the array, which specifically interacts with said target molecule.

If, within the scope of the present invention, no replacement of solutions in the reaction chamber and/or removal of solutions from the reaction chamber is performed between feeding the sample containing target molecules into a reaction chamber and detecting the interaction, it is, however, conceivable that during this time period solutions can additionally be introduced into the reaction chamber without performing a replacement or removal of the solutions already present in the reaction chamber.

A first object of the present invention thus relates to a method for the qualitative and/or quantitative detection of targets and, in particular, of molecular interactions between probe and target molecules, in particular comprising the following steps:

a) introducing a sample containing target molecules into a reaction chamber having a microarray, said microarray comprising a substrate onto which probe molecules are immobilized on array elements; and
b) detecting an interaction between the target molecules and the probe molecules immobilized on the substrate, wherein after introducing the sample containing target molecules and prior to and during the detection no replacement of solutions in the reaction chamber and/or removal of solutions from the reaction chamber takes place.

In this aspect, detection of an interaction between the target molecules to be detected and the probe molecules immobilized on the microarray substrate can typically be performed without first contacting the microarray with a liquid free of the target molecules. That is, the detection of the interaction between targets and probes can occur without rinsing or washing steps after the interaction reaction has taken place and/or without the removal of molecules from the reaction chamber that do not specifically interact with probes on the microarray after the interaction reaction has taken place This may be ensured in the inventive method by means of foci-selective detection methods, such as confocal techniques or the evanescent de-coupling of excitation light (TIRF) in the sample substrate based on the use of a depth-selective illumination due to, for example, total reflection, or the use of methods based on waveguides. Such foci-selective methods may be used in cases when a further exclusion of the background signals caused by the fluorescence molecules present in the liquid, i.e. not hybridized, is required in order to increase sensitivity. By using fluorescence-labeled target molecules, the specific interaction signals can thus be discriminated from the background fluorescence by employing methods such as total internal reflection fluorescence microscopy (TIRF) or confocal fluorescence microscopy.

Examples for this are CCD-based detectors, which implement the excitation of the fluorophores in the dark field by means of incident light or transmitted light for the purpose of discriminating optical effects like dispersion and reflections (see for example C. E. Hooper et al., Quantitative Photone Imaging in the Life Sciences Using Intensified CCD Cameras, Journal of Bioluminescence and Chemoluminescence (1990), 337-344). Further alternatives for fluorescence detection systems, which can be used in the method according to the present invention, are white light setups, like for example described in WO 00/12759, WO 00/25113, and WO 96/27025; confocal systems, like for example described in U.S. Pat. Nos. 5,324,633, 6,027,880, 5,585,639, and WO 00/12759; confocal excitation systems based on Nipkow discs in confocal imaging, as for example described in U.S. Pat. No. 5,760,950; systems based on structured excitation distribution, as for example described in WO 98/57151; large-scale integrated fluorescence detection systems using micro-optics, like for example described in WO 99/27140; and laser scanning systems, as for example described in WO 00/12759. A general procedure of fluorescence detection methods using such conventional fluorescence detection systems is, for example, described in U.S. Pat. No. 5,324,633.

The devices described in WO 2004/087951, wherein the reaction chamber is formed by a capillary gap, are particularly suitable for performing a detection method according to the present invention without replacing solutions in the reaction chamber and/or removing solutions from the reaction chamber. The relevant contents of WO 2004/087951 are hereby explicitly referred to.

In a further embodiment of this aspect of the present invention, replacing and/or removing solutions from the reaction chamber is avoided by performing the detection by means of detecting the mass alteration on the array surface, as described, for example, in WO 03/004699. The relevant contents of WO 03/004699 are hereby explicitly referred to.

In a further embodiment of this aspect of the present invention, replacing and/or removing solutions from the reaction chamber is avoided by performing the detection by means of detecting acoustic surface waves, as is described, for example, in Z. Guttenberg et al., Lab Chip. 2005; 5(3):308-17.

In a further embodiment of this aspect of the present invention, replacing and/or removing solutions from the reaction chamber is avoided by performing the detection by means of electrochemical detection via electrodes on the surface of the substrate onto which the probes are immobilized, like, for example, by means of measuring the alteration of redox potentials (see, for example, X. Zhu et al., Lab Chip. 2004; 4(6):581-7) or cyclic voltometry (see, for example, J. Liu et al., Anal Chem. 2005; 77(9):2756-2761; J. Wang, Anal Chem. 2003; 75(15):3941-5).

In a further embodiment of this aspect of the present invention, replacing and/or removing solutions from the reaction chamber is avoided by performing the detection by means of electric detection via electrodes on the surface of the substrate, onto which the probes are immobilized, like, for example, by means of impedance measurement (see, inter alia, S. M. Radke et al., Biosens Bioelectron. 2005; 20(8): 1662-7).

In a further embodiment of this aspect of the present invention, replacing and/or removing solutions from the reaction chamber is avoided by employing a substrate having FRET probes (FRET, fluorescence resonance energy transfer). The use of such FRET probes is based on the formation of fluorescence quencher pairs, so that a fluorescence signal only occurs, if a target molecule has bound to the complementary probe on the surface. The use of FRET probes is, for example, described in B. Liu et al., PNAS 2005, 102, 3, 589-593; K. Usui et al., Mol Divers. 2004; 8(3):209-18; J. A. Cruz-Aguado et al., Anal Chem. 2004; 76(14):4182-8 and J. Szollosi et al., J Biotechnol. 2002; 82(3):251-66.

In a further embodiment of this aspect of the present invention, replacing and/or removing solutions from the reaction chamber is avoided by means of employing an inventive device for the qualitative and/or quantitative detection of analytes, as detailed below, wherein the device comprises:

a) a microarray on a substrate, onto which probe molecules are immobilized on array elements, said microarray being disposed on a first surface of the device; and b) a detection chamber formed between the first surface including the microarray disposed thereon and a second surface, wherein the distance between the microarray and the second surface is variable.

A further object of the present invention relates to the use of FRET probe molecules, as described above, and/or detection methods selected from the group consisting of total internal reflection fluorescence microscopy (TIRF), as described above, confocal fluorescence microscopy, as described above, methods for detecting mass alterations, as described above, methods for detecting acoustic surface waves, as described above, methods for the electrochemical and/or electric detection, as described above, for avoiding replacement of solutions in a reaction chamber and/or removal of solutions from a reaction chamber during or after introducing a sample containing target molecules into the reaction chamber and before or during the detection in a method for the qualitative and/or quantitative detection of molecular interactions between probe and target molecules, in particular comprising the following steps:

a) introducing a sample containing target molecules into a reaction chamber having a microarray, said microarray comprising a substrate onto which probe molecules are immobilized on array elements; and b) detecting an interaction between the target molecules and the probe molecules immobilized on the substrate.

A further object of the present invention particularly relates to a device for the qualitative and/or quantitative detection of analytes, e.g. by detection of molecular interactions between probe molecules and analytes, comprising:

a) a microarray on a substrate, onto which probe molecules are immobilized on array elements, said microarray being disposed on a first surface of the device; and
b) a detection chamber formed between the first surface including the microarray disposed thereon and a second surface,
wherein the distance between the microarray and the second surface is variable.

After an interaction between probe molecules and target molecules has taken place, an undesired background is caused by the labeled molecules present in the sample solution, which do not interact with the probe molecules. In case the probe and/or target molecules are nucleic acids and/or nucleic acid analogs, said background is caused, in particular, by the labeled primers and/or labeled nucleic acids present in the sample solution, which are not hybridized with the probe molecules.

A known possibility of removing disturbing background signals is the replacement of the sample solution after completed interaction with a non-labeled, for example non-fluorescent, solution. However, this variant is generally lavish and prone to interference owing to corrosion, aging of the solutions and impermeability problems.

Typically, the distance between the microarray and the second surface is variable. A variable distance between the microarray and the second surface means that the detection chamber of the device can be varied, by, for example, compression (e.g., by an external force applied to a detection chamber). In particular, the distance between the microarray and the second surface is variable in such a way that the microarray can rest evenly and/or reversibly with its active surface, i.e. the surface on which the nucleic acid probes are immobilized, on the second surface or can be pressed onto the same. This also applies, if the inventive device has a displacement structure located on the second surface, as described above.

A compressible chamber therefore allows displacement of sample solution containing labeled molecules, which do not interact with the probe molecules and therefore constitute an undesired background, by reducing the distance between the microarray and the second surface before performing the detection. In this manner, a detection of interactions between probe and target molecules using any optical detection systems is possible without replacing the sample solution with a non-labeled solution before the detection. For example, simple fluorescence-microscopic imaging of the DNA chip for detecting the interaction signals by means of the device according to the present invention without replacing the sample solution with a non-labeled, in particular weakly fluorescent, liquid, is possible. In particular, this applies, if the inventive device has a displacement structure located on the second surface, as described above.

In some embodiments of the device, the focusing requirements are reduced as compared to a device in which the detection chamber does not have variable internal distance. Thus, the device according to the present invention may allow, for example, the use of a simple fluorescence microscope device without autofocus function as reading device for the detection of the hybridization between targets and probes without necessitating liquid-handling steps like, in particular, washing steps, for removing target molecules not bound to the array, like for example non-hybridized target nucleic acids, contrarily to the fluorescence-optical detection systems hitherto used for the detection of nucleic acids. This also applies, if the inventive device has a displacement structure located on the second surface, as described above.

Despite multifunctional sample treatment and analysis, which is feasible by means of the device according to the present invention, a very cost-efficient system for detecting and, optionally, amplifying target molecules in a sample is provided. The devices according to the present invention, in particular in connection with an optical detection system, are furthermore robust to such an extent that they are also suitable for mobile use.

By means of suitably selecting the chip, processing protocols, and analysis chemicals, the device according to the present invention can be employed for the most different types of gene analyses, like for example predisposition diagnostics, germ diagnostics and typing. Thus, a complete genetic analysis is conductible with little equipment effort in the device according to the present invention, which can also be implemented as a disposable cartridge. Therefore, the device according to the present invention allows performing detection methods on-site, for example during blood donation. A measured result can be quickly obtained, e.g. within 0.5 to 2 hours. All the steps practicable with the device according to the present invention, like purification, processing, amplification of nucleic acids, and the actual hybridization can be conducted automatically. The operator only needs to be familiar with sample withdrawal, sample feeding into the device according to the present invention, and taking notice of the analysis results.

In some embodiments, the distance between the microarray and the second surface is variable in a range of about 0 to about 1 mm. Further suitable lower limits for the distance between microarray and second surface are about 0.1 μm, about 1 μm, and about 10 μm. Further suitable upper limits for the distance between the microarray and second surface are about 0.01 mm, about 0.5 mm, about 1 mm and about 0.3 mm. Surprisingly, the interaction between probes and targets is not even affected if the distance between substrate surface and second surface is approximately zero or about zero. This also applies, if the inventive device has a displacement structure located on the second surface, as described above.

In a further embodiment, the device according to the present invention further comprises a detection system. Herein, the detection system may be an optical system. Examples for systems suitable within the scope of the present invention are detection systems based on fluorescence, optical absorption, resonance transfer, and the like. Preferably, the optical detection system is a fluorescence-optical system. E.g., the fluorescence-optical system is a fluorescence microscope without autofocus, for example a fluorescence microscope with fixed focus.

In a further embodiment, the detection system is connected with at least one spacer, which adjusts a distance between the detection system and the second surface when resting upon the second surface. If the distance between the microarray and the second surface is about zero, the spacer also determines the distance between the surface of the chip and the optical system of the detection device. It is thus possible to keep the variance of the distance between optical detection device and microarray surface very small. The variance only comprises the thickness variance of the second surface, in general a glass surface, the deflection of the second surface, and the thickness of a layer caused by possible impurities at the pressing surfaces between chip and detection plane or between spacer and detection plane. This renders re-focusing for bringing the optical system into focus unnecessary, which considerably simplifies the operation of the device and/or renders an expensive autofocus installation unnecessary.

In a further embodiment, laterally limiting compensation zones, which keep the volume in the detection chamber basically constant when the distance between microarray and second surface is reduced, are provided for the reaction space formed between the first and the second surface. This also applies, if the inventive device has a displacement structure located on the second surface, as described above.

In addition, the reaction space formed between the first and the second surface may be laterally limited by elastic seals. In some embodiments, the elastic seals are made of silicone rubber. This also applies, if the inventive device has a displacement structure located on the second surface, as described above.

In order to ensure the detection of interactions between probe and target molecules, the second surface may be made of an optically transparent material, e.g. glass. The same also applies to an optional displacement structure which, however, may also be made of an elastic and optionally transparent material.

In a further embodiment of the device according to the present invention, the first surface is, at least in the region of the microarray configured in such a way that the first surface can be guided relatively to the second surface in such a way that the distance between the micro array and the second surface is variable.

Herein, the first surface can, at least in the region on which the probes can be immobilized, be configured in such a way that this region can be guided in the direction towards the second surface so that the distance between the first surface and the second surface can be reduced and/or that the micro array can be guided in a direction away from the second surface in a way that that the distance between the microarray and the second surface can be increased. This also applies, if the inventive device has a displacement structure located on the second surface, as described above.

In this embodiment, the first surface may be, at least in the region of the micro array, elastically deformable. E.g., the first surface may be made of an elastic synthetic material, for example an elastic membrane. This also applies, if the inventive device has a displacement structure located on the second surface, as described above.

In a further embodiment, the first surface is formed by two superimposed layers, wherein an outer layer of the two superimposed layers has a cut-out at least in the region below the micro array. In this embodiment, an inner layer of the two superimposed layers may be formed by an elastic seal or a sealing membrane, which usually also limits the reaction space laterally (see FIGS. 6A and 6B). The sealing membrane can be guided toward the second surface. The sealing membrane closes a recess in the outer layer, which usually corresponds to the lower side of the chamber body. During the performance of a peR in the reaction chamber, an internal pressure, which renders the reaction chamber pressure-resistant despite the relatively labile sealing membrane, is generated due to the higher temperatures prevailing in a PCR. This embodiment thus corresponds to a self-closing valve. In order to ensure the elasticity of the sealing membrane, the membrane is preferably provided with a compensation fold (see FIGS. 6A and 6B). This also applies, if the inventive device has a displacement structure located on the second surface, as described above.

It can further be provided that the device comprises at least one means, by which the microarray can be guided relatively to the second surface. In the following, said means will be referred to as means for guiding the first surface or actuator. Said means for guiding the first surface is preferably selected from the group consisting of a rod, a pin, a tappet, a stencil and a screw. This also applies, if the inventive device has a displacement structure located on the second surface, as described above.

Herein, the device can comprise at least one means for guiding the first surface, by which the first surface can be guided towards the second surface in such a way that the distance between the micro array and the second surface can be reduced and/or by which the micro array can be guided away from the second surface in such a way that the distance between the micro array and the second surface can be increased. This also applies, if the inventive device has a displacement structure located on the second surface, as described above.

In one embodiment, the micro array can be guided relatively to the second surface by applying pressure and/or fraction, which is exerted on the first surface by the means.

Herein, the above-mentioned spacers resting on the second surface can serve as holders for the means for guiding the first surface.

In a further embodiment, the first surface can be caused to vibrate by the means for guiding the first surface, in particular to vibrate at a frequency of 10 to 30 Hz, particularly preferably of about 20 Hz. In this manner, bubbles present above the chip, which would impede detection, can be removed and/or the interaction speed, for example the hybridization speed, can be increased by a thorough mixing owing to the vibration of the means for guiding the first surface.

In a further embodiment, the second surface can be guided relatively to the first surface in such a way that the distance between the first and the second surface is variable.

There, the second surface can be guided relatively to the first surface in such a way that the distance between the microarray and the second surface can be reduced and/or that the distance between the microarray and the second surface can be increased.

In particular, this can be ensured by the second surface being guidable relatively to the first surface by means of the spacer exerting pressure and/or traction on the second surface, such that the distance between the microarray and the second surface is variable at least in that area where the detection of the target is to be performed.

In a further embodiment of the device according to the present invention, both the first surface and the second surface can be guided in such a way that the distance between the microarray and the second surface is variable.

In a further embodiment, the device according to the present invention is developed in such a way that, already in the original state, the microarray mounted on the first surface rests, preferably evenly, on the second surface forming the detection plane. The first surface can be guided in such a way that the distance between the microarray and the second surface can be increased. Herein, the first surface may be made of an elastic material.

In a further embodiment of the device according to the present invention, the first surface is developed in a pivotable manner around a rotation axis. The rotation axis divides the first surface into two sides. In this embodiment, the microarray is arranged on a first flanking portion of the first surface. The rotation axis for the swiveling motion may run through the center of the first surface, i.e. the two flanking portions preferably are of equal size. The first surface may be made of an elastic material.

In a first position of the pivotable first surface, the first surface is arranged basically parallel to the second surface. In the first position, the surface of the microarray contacts the second surface basically evenly, i.e. the substrate surface with the probe molecules immobilized thereon is basically not moistened by the sample solution. In said first position, a space, which is also referred to as processing chamber in the following, is formed between the second flanking portion of the first surface and the second surface. Said processing chamber can serve as chamber for processing the sample solution.

In a second position of the pivotable first surface, the first surface is arranged at an angle other than 180° in relation to the second surface. In said second position, the surface of the microarray does not contact the second surface, i.e. the probe molecules immobilized on the substrate of the microarray are freely accessible for the target molecules present in the sample solution and can therefore interact with the latter. In the second position, the processing chamber is compressed.

The pivotable first surface can preferably be swiveled by means of exerting traction on the first flanking portion of the first surface and/or by means of exerting pressure on the second flanking portion of the first surface. Pressure and/or traction can be exerted by means of a means for guiding the first surface, as described above.

All preceding embodiments preferably have a displacement structure located on the second surface, as described above, namely on the side of the second surface that is facing detection chamber, i.e. the microarray. Thereby, the displacement structure is positioned in such a way that it is located opposite to the microarray and evenly rests on it in the compressed state, wherein during compression the analyte solution being is substantially displaced from the reaction chamber and the surface of the microarray, respectively.

The chip or the substrate or the first surface may consist of silicon, ceramic materials like aluminum oxide ceramics, borofloat glasses, quartz glass, single-crystal $CaF_2$, sapphire discs, topaz, PMMA, polycarbonate, and/or polystyrene. The selection of the materials is also to be made dependent on the intended use of the device or the chip. If, for example, the chip is used for characterizing PCR products, only those materials may be used, which can resist a temperature of 95° C.

In some embodiments, the chips are functionalized by means of nucleic acid molecules, in particular by means of DNA or RNA molecules. However, they can also be functionalized by means of peptides and/or proteins, like for example antibodies, receptor molecules, pharmaceutically active peptides, and/or hormones, carbohydrates and/or mixed polymers of said biopolymers.

In a further embodiment, the molecular probes are immobilized on the substrate surface via a polymeric linker, for example a modified silane layer. Such a polymeric linker can serve for the derivative preparation of the substrate surface and therefore for the immobilization of the molecular probes. In the case of covalent binding of the probes, polymers, for example silanes, are used, which have been functionalized or modified by means of reactive functionalities like epoxides or aldehydes. Furthermore, the person skilled in the art is also familiar with the activation of a surface by means of isothiocyanate, succinimide, and imido esters. To this end, amino-functionalized surfaces are often correspondingly derivatized. Furthermore, the addition of coupling reagents, like for example dicyclohexylcarbodiimide, can ensure corresponding immobilizations of the molecular probes The chamber body of the reaction chamber may consist of materials like glass, synthetic material, and/or metals like high-grade steel, aluminum, and brass. For its manufacturing, for example synthetic materials suitable for injection molding can be used. Inter alia, synthetic materials like macrolon, nylon, PMMA, and teflon are conceivable. In special embodiments, electrically conductive synthetic materials like polyamide with 5 to 30% carbon fibers, polycarbonate with 5 to 30% carbon fibers, polyamide with 2 to 20% stainless steel fibers, and PPS with 5 to 40% carbon fibers and, in particular, 20 to 30% carbon fibers are preferred. Alternatively and/or in addition, the reaction space between first and second surface can be closed by means of septa, which, for example, allow filling of the reaction space by means of syringes. In a further embodiment, the chamber body consists of optically transparent materials like glass, PMMA, polycarbonate, polystyrene, and/or topaz. Herein, the selection of materials is to be adjusted to the intended use of the device. For example, the temperatures the device will be exposed to are to be considered when selecting the materials. If, for example, the device is to be used for performing a peR, for example, only those synthetic materials may be used, which remain stable for longer periods at temperatures like 95° C.

In particular, the chamber body is developed in such a way that the micro array can be pressed against the second surface evenly and/or reversibly with its active side, i.e. the side of the array, whereon the nucleic acid probes are immobilized.

Figure 2:
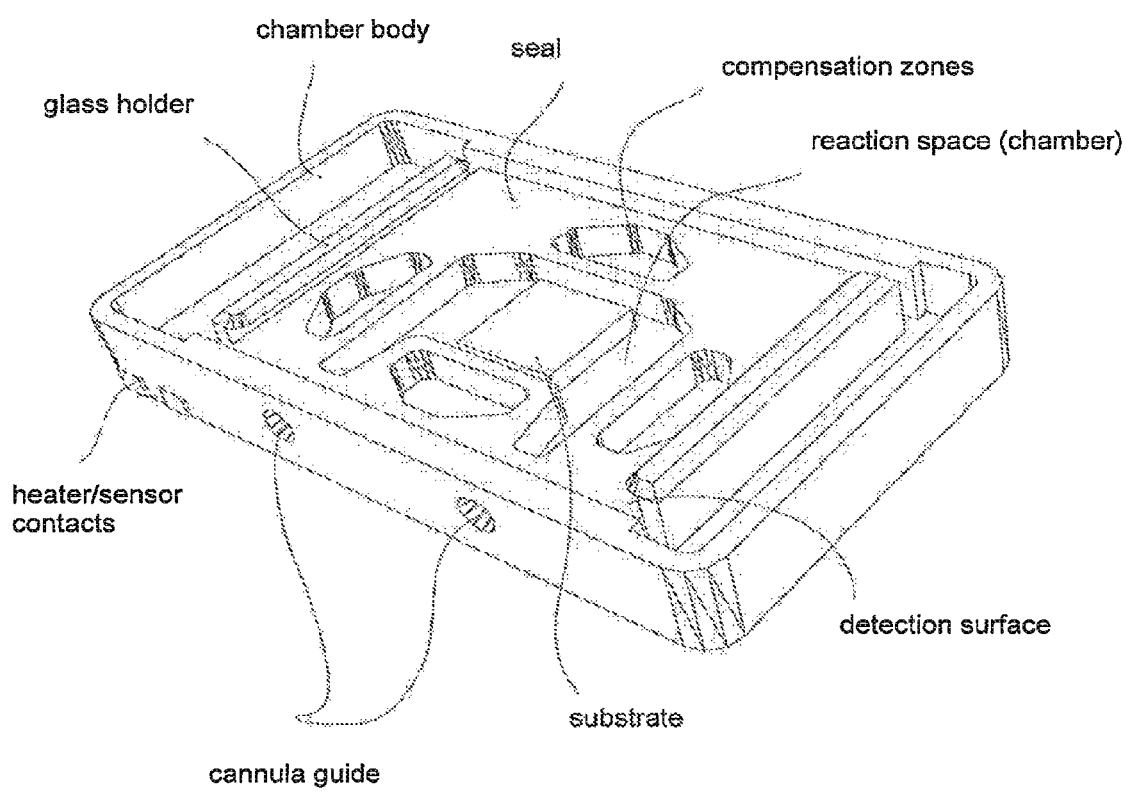
FIG. 2 is a perspective view of the process unit of a device according to the invention.
Figure 3:
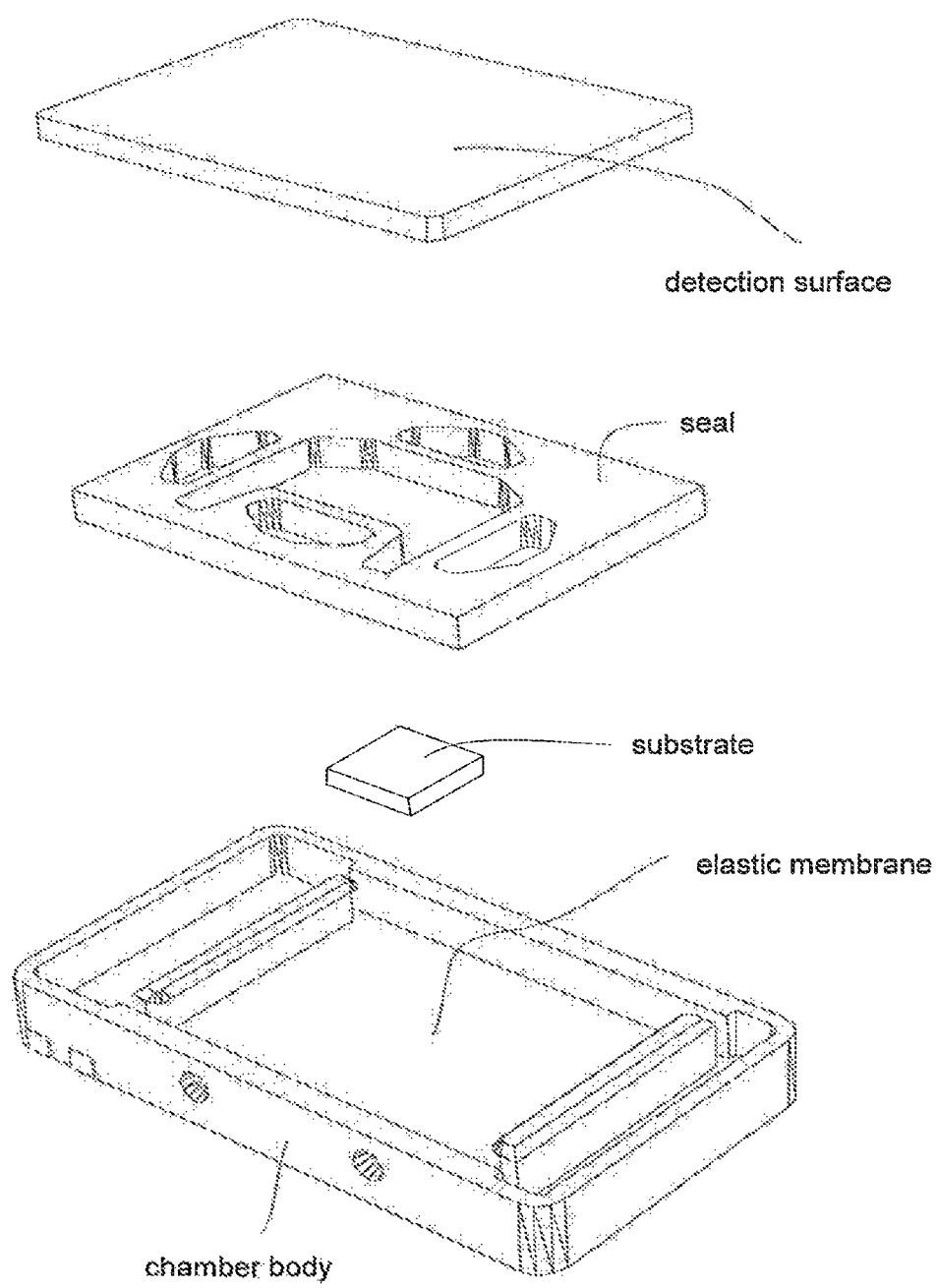
FIG. 3 is an exploded view of the process unit of a device according to the invention.

In a special embodiment, the device according to the present invention comprises modules selected from the group consisting of a chamber body, preferably made of a synthetic material, a septum or a seal sealing the reaction chamber, a DNA chip, and/or a second optically transparent surface, preferably a glass pane, wherein the second surface can optionally also serve as chip simultaneously (see FIG. 2 and FIG. 3). In this embodiment, chamber body and seal are developed elastically, so that the DNA chip can be pressed evenly and reversibly to the glass cover with its active side. Thereby, the labeled analysis liquid located between DNA chip and detection surface is entirely displaced (see FIGS. 5A-C and FIGS. 6A and 6B). In this manner, a highly sensitive fluorescence detection, for example a computer-imaging fluorescence microscopy, can be conducted without being impaired by a background fluorescence of the sample solution.

The second surface of the chamber body may consist of transparent materials like glass and/or optically permeable synthetic materials, for example PMMA, polycarbonate, polystyrene, or acryl. The displacement structures mentioned above, if present, may be made of these materials or of the above-mentioned materials.

In some embodiments, the detection and/or reaction chamber is developed between the second surface and the microarray in the form of a capillary gap having variable thickness. By forming a capillary gap between chip and detection plane, capillary forces can be utilized for safely filling the reaction chamber. Said capillary forces already occur in the non-compressed state of the reaction chamber; they can, however, be increased by compressing the reaction chamber. Particularly preferably, the capillary gap has a thickness in the range of about 0 µm to about 100 µm. This also applies, if a displacement structure is present, as described above From the possibility of being able to compress the reaction space and therefore to reduce the width of the gap between microarray and detection plane, further possibilities of handling the liquid within the reaction chamber arise. Thus, in a further embodiment of the present invention, several sub-chambers are provided instead of one single chamber, wherein the partitions between said sub-chambers do not reach the height of the second surface, so that a fluid connection is generated between the sub-chambers in a non-compressed state of the reaction chamber. By compressing the reaction chamber, the chambers can be separated. Thus, by compressing, the partitions between the chambers can be operated like valves.

A special embodiment of said sub-chambers separated by valves is the subdivision of the reaction space of the device according to the present invention into different PCR chambers. In each chamber, individual primers are presented. In the beginning, the sub-chambers are simultaneously filled with the analyte. Subsequently, the reaction space is compressed. Afterwards, the reaction space is subjected to the temperature cycle for the PCR. As each sub-chamber is filled with different primers, a different amplification reaction takes place in each chamber. An exchange between the chambers does not occur.

After the PCR has been performed, hybridization takes place. Herein, each sub-chamber can contain an individual chip region or an individual chip. However, it is also possible to facilitate a fluid connection between the sub-chambers by increasing the distance between microarray and second surface, so that the different substances to be amplified mix and in this manner hybridize to a chip surface.

The embodiment having sub-chambers separated by valves may result in an increase in multiplexity of the PCR, i.e. the number of independent PCRs with one sample, which is limited for biochemical reasons in a one-stage reaction. Thus, it is possible to adjust the number of PCRs to the possible number of probes on the chip surface.

In a further embodiment of the present invention, the reaction chamber thus comprises at least two sub-chambers, wherein in a first non-compressed state the sub-chambers are in fluid connection and in a second compressed state there is no fluid connection between the sub-chambers.

In one embodiment, each sub-chamber is assigned to a defined region of the microarray.

In particular, the sub-chambers can be formed by equipping the microarray and/or the second surface with cavities, which serve as walls between the sub-chambers.

The walls between the sub-chambers may be formed by elastic seals.

As a matter of course, this embodiment of the process unit having sub-chambers separated by valves can arbitrarily be combined with any of the above-described compression principles.

In a further embodiment of the device according to the present invention, the first surface is made of a partially deformable elastic material, for example an elastic membrane. In that only a part of the reaction space can be compressed, sub-chambers, wherein the chip is guided toward the second surface, sub-chambers, which cannot be separated from each other, and sub-chambers, which cannot be altered, can, inter alia, be generated. Thereby, simple pump systems, which can, for example, be used for pumping salts into the hybridization chamber at the end of an amplification reaction, can be implemented in the reaction space. This can, for example, be advantageous for optimizing the chemical hybridization conditions of the PCR buffer, wherein the PCR buffer is optimized only for the conduction of the PCR.

When subdividing the reaction chamber into several sub-chambers, it is preferred to use several means for agitating. Usually, the means for agitating are identical with the means for guiding the first surface. Thereby, individual chambers can be specifically agitated. This can, for example, be appropriate for implementing separate amplification spaces and/or hybridization spaces.

Of course, this embodiment of the device according to the present invention having several means for agitating can also be arbitrarily combined with any of the above-described compression principles.

The above-described components or modules of the device according to the present invention selected from the group consisting of a chamber body, seals laterally limiting the reaction space, micro-array, and detection plane form the so-called process unit of the inventive device. In the process unit, PCR, hybridization reactions, detection and/or evaluation can be performed.

The process unit of the device according to the present invention may be constructed in a modular manner. This means that the process unit can comprise any arbitrary combination of the modules. The modules can also be exchanged during analysis.

All preceding embodiments preferably have a displacement structure located on the second surface, as described above, namely on the side of the second surface that is facing the microarray. Thereby, the displacement structure is positioned in such a way that it is located opposite to the microarray and evenly rests on it in the compressed state, wherein during compression the analyte solution being is substantially displaced from the reaction chamber and the surface of the microarray, respectively.

In a further embodiment, the device according to the present invention in addition comprises a temperature controlling and/or regulating unit for controlling and/or regulating the temperature in the reaction chamber. Such a temperature controlling and/or regulating unit for controlling and/or regulating the temperature in the reaction chamber in particular comprises heating and/or cooling elements or temperature blocks. Herein, the heating and/or cooling elements or the temperature blocks can be arranged in such a way that they contact the first surface and/or the second surface. By means of contacting both the first and the second surface, particularly efficient temperature controlling and regulating is ensured.

In this embodiment, the substrate of the microarray or the first surface and/or the second surface is connected with heating and/or cooling elements and/or temperature blocks and should then preferably consist of materials with good heat-conducting properties. Such heat conductive materials offer the considerable advantage of ensuring a homogenous temperature profile throughout the entire surface of the reaction space and therefore allowing temperature-dependent reactions, like for example a PCR, to be conducted homogenously throughout the entire reaction chamber, delivering high yields, and controllably or regulatably with high accuracy.

Thus, in one embodiment, the substrate of the microarray or the first surface or the second surface consist of materials having a good heat conductivity, e.g. having a heat conductivity in a range of 15 to 500 $Wm^{-1}K^{-1}$, in a range of 50 to 300 $Wm^{-1}K^{-1}$, or in a range of 100 to 200 $Wm^{-1}K^{-1}$, wherein the materials are usually not optically transparent. Examples for suitable heat conductive materials are silicon, ceramic materials like aluminum oxide ceramics, and/or metals like high-grade steel, aluminum, copper, or brass.

If the substrate of the microarray or the first surface or the second surface of the device according to the present invention substantially consists of ceramic materials, the use of aluminum oxide ceramics is preferred. Examples for such aluminum oxide ceramics are the ceramics A-473, A-476, and A-493 by Kyocera (Neuss, Germany).

In one embodiment, the substrate of the microarray or the first surface or the second surface is equipped with optionally miniaturized temperature sensors and/or electrodes or has heater structures on its back side, i.e. the side facing away from the reaction chamber, so that tempering the sample liquid and mixing the sample liquid by means of an induced electro-osmotic flow is possible.

The temperature sensors, for example, can be developed as nickel-chromium thin film resistance temperature sensors.

The electrodes, for example, can be developed as gold-titanium electrodes and, in particular, as quadrupole.

The heating and/or cooling elements can be selected in such a way that fast heating and cooling of the liquid in the reaction chamber is possible. Herein, fast heating and cooling is understood to denote that temperature alterations in a range of 0.2 K/s to 30 K/s, of 0.5 K/s to 15 K/s, of 2 K/s to 15 K/s, or of 8 K/s to 12 K/s or about 10 K/s can be mediated by the heating and/or cooling elements. Temperature alterations of 1 K/s to 10 K/s can also be mediated by the heating and/or cooling elements.

The heating and/or cooling elements, for example resistance heaters, can, for example, be developed as nickel-chromium thin film resistance heaters.

For further details on the specification and dimension of the temperature sensors, heating and/or cooling elements or means for increasing the temperature and of the electrodes, it is referred to the contents of the International Patent Application WO 01/02094.

In a further embodiment, tempering of the reaction chamber is ensured by using a chamber body consisting of electrically conductive material. Such an electrically conductive material may be an electrically conductive synthetic material, like for example polyamide, optionally having 5 to 30% carbon fibers, polycarbonate, optionally having 5 to 30% carbon fibers, and/or polyamide, optionally having 2 to 20% stainless steel fibers. Preferably, PPS (polyphenylenesulfide) with 5 to 40% carbon fibers, particularly preferably 20 to 30% carbon fibers, is used as electrically conductive synthetic material. It is further preferred that the chamber body is developed in such a way that it has swellings and tapers. Such swellings or tapers in the chamber body allow specific heating of the reaction chamber or the corresponding surfaces. Furthermore, the use of such volume conductors has the advantage that, also with optionally lower heat conductivity of the material used, homogenous tempering of the chamber or the corresponding surfaces is ensured, as heat is released in each volume element.

Coupling and educing heat into the reaction space can be conducted in different ways. Inter alia, it is intended to bring in heat via external microwave radiation, internal or external resistance heating, internal induction coils or surfaces, water cooling and heating, friction, irradiation with light, in particular with IR light, air cooling and/or heating, friction, temperature emitters, and peltier elements.

Measuring the temperature in the reaction space can be conducted in different ways, for example by means of integrated resistance sensors, semi-conductor sensors, light waveguide sensors, polychromatic dyes, polychromatic liquid crystals, external pyrometers like IR radiation and/or temperature sensors of all types, which are integrated in the means for guiding the microarray.

Measuring the temperature in the reaction chamber can furthermore be conducted by means of integrating a temperature sensor in the chamber body, for example by means of injection in the course of the production process of the chamber body, by means of non-contact measurement with the aid of a pyrometer, an IR sensor, and/or thermopiles, by means of contact measurement, for example with a thermal sensor integrated in the device and contacting a suitable surface or a suitable volume of the chamber body or the chamber, by means of measuring the temperature-dependent alteration of the refraction index at the detection plane, by means of measuring the temperature-dependent alteration of the color of specific molecules, for example in the solution, on the probe array, or in the chamber seal, and/or by means of measuring the temperature-dependent alteration of the pH-value of the solution used by means of measuring the color alteration of a pH-sensitive indicator, for example by means of measuring its absorption.

Furthermore, automatic limitation of temperature can occur due to a surge of the resistance of the heater, wherein the corresponding threshold temperature preferably lies in a range of 95° C. to 110° C. When reaching the threshold temperature, the resistance of the heater surges, whereby virtually no current flows and therefore virtually no heat is emitted anymore. In particular, polymers, like electrically conductive polyamides, whose resistance increases at the threshold temperature due to the alteration of the matrix of the polymer or a phase alteration, can be used for such heaters.

In one embodiment, the temperature controlling and regulating unit can be integrated in the first surface and/or the second surface. In said embodiment, the process unit is, in particular, equipped with a heater (see FIG. 4), which serves for implementing the temperature alterations in PCR and hybridization.

The process unit may have a low heat capacity, so that maximum temperature alteration speeds of, for example, at least 5 K/s are practicable at a low power demand. In order to ensure fast cooling of the process unit, another preferred embodiment intends providing a cooling system, for example an air cooling system.

Cooling of the process unit can also be achieved by means of permanently tempering the space surrounding the process unit to a lowered temperature and thereby passively cooling the cartridge. This renders active cooling of the reaction cartridge unnecessary.

In a further embodiment, the temperature controlling and regulating unit can comprise temperature blocks, which are each pre-heated to a defined temperature. In said embodiment the process unit, in particular, has no integrated heater. Owing to the omission of an integrated heating system, the process unit can be provided even more cost-efficiently.

Figure 7:
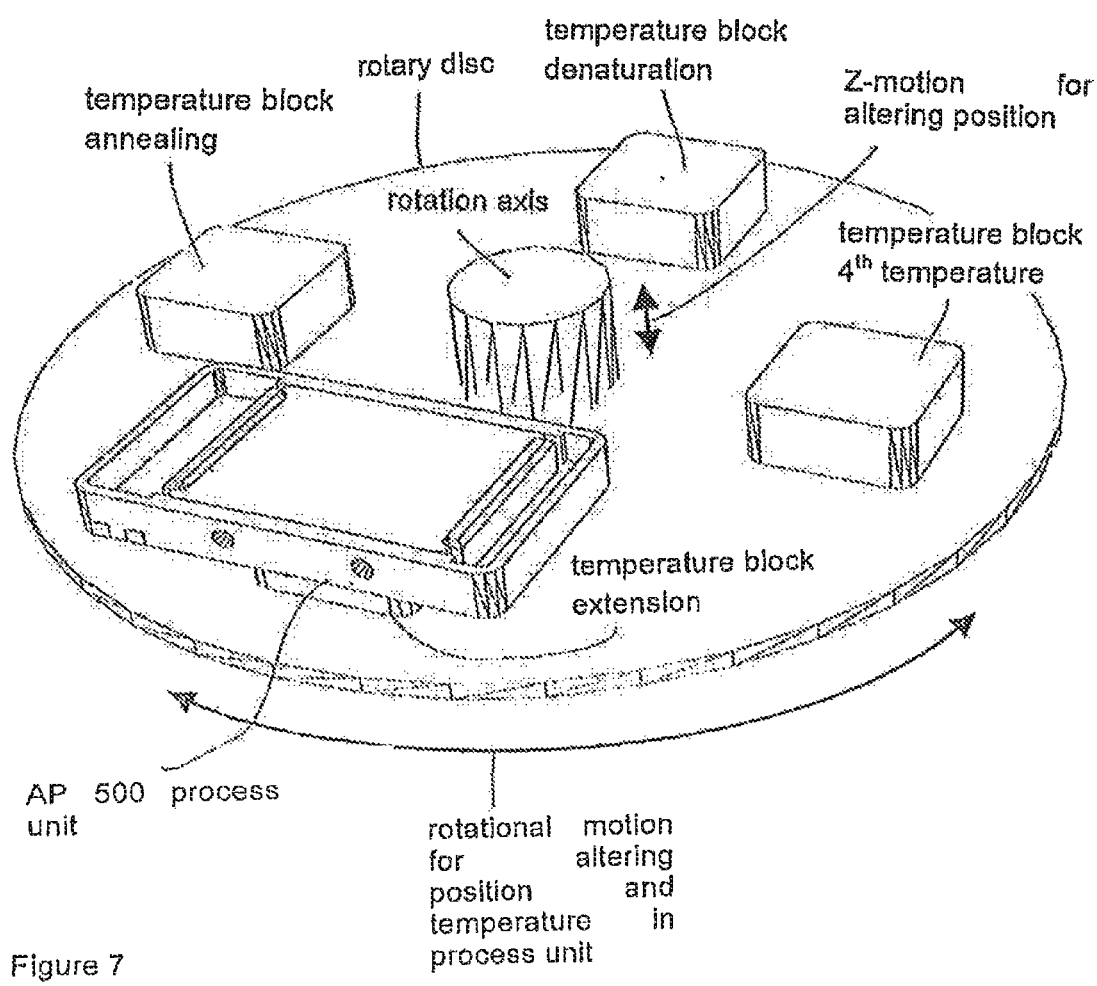
FIG. 7 is a view of an inventive device comprising four temperature blocks mounted on a rotary disc.

Heat transfer between the temperature blocks of the temperature controlling and regulating unit is preferably ensured in that the temperature blocks contact the first surface and/or second surface of the device according to the present invention. The temperature blocks can be arranged linearly or on a rotary disc and, for example, be integrated in the detection device in this manner. FIG. 7 shows a rotary disc having several temperature blocks, each of which is adjusted to a defined temperature. By means of exchanging the temperature blocks below the process unit, the process unit is brought to a specific temperature defined by the temperature block. The temperature blocks may be manufactured in such a way, that they have a significantly higher heat capacity than the process unit, so that maximal temperature alteration speeds of, for example, at least 5 K/s are also practicable in this embodiment. The temperature blocks may only be thermostaticized instead of heated or cooled, so that the energy demand is also minimal in this case. In this embodiment, cooling or heating the process unit can be omitted.

In a further embodiment, the temperature controlling and regulating unit is integrated in the means for guiding the first surface and/or in the means for agitating, and/or in the spacer. In this embodiment, heat transfer is conducted by means of contacting the means and/or the spacer with the first surface and/or the second surface.

The device additionally may comprise a reprocessing unit for purifying and/or re-concentrating the sample solution and/or for controlling the loading and unloading of the reaction chamber with fluids. Within the scope of the present invention, fluids are understood to denote liquids and gases. Furthermore, the analysis solution can be re-buffered in the reprocessing unit. The reprocessing unit can finally also be used for providing the necessary analysis chemicals. The connection of the fluid containers with the reaction chamber can, for example, be developed as described in the International Patent Application WO 01/02094.

In this embodiment, the reaction chamber and the reprocessing unit may be connected via two cannulas, wherein the cannulas are arranged in such a way that a first cannula ensures the feeding of fluids from the reprocessing unit into the reaction chamber and a second cannula ensures the escape of air dislocated by the fed fluids from the reaction chamber. A sample fed into the reprocessing unit can thus reach the reaction chamber of the process unit via the cannulas. To this end, the cannulas are arranged in such a way that they reach into the reaction chamber via the cannula guide.

The reprocessing unit can be developed in such a way that it can be separated from the process unit. After filling the reaction chamber with the sample solution and, optionally, with further reaction liquids, the reprocessing unit can thus be separated from the process unit, preferably be disengaged, and, optionally, be discarded.

All preceding embodiments preferably have a displacement structure located on the second surface, as described above, namely on the side of the second surface that is facing the microarray. Thereby, the displacement structure is positioned in such a way that it is located opposite to the microarray and evenly rests on it in the compressed state, wherein during compression the analyte solution being is substantially displaced from the reaction chamber and the surface of the microarray, respectively.

In the following, embodiments of integrated or non-integrated units for filling the reaction chamber, which will also be referred to in the following as filling unit or reprocessing unit, will be described. These embodiments may have the above-mentioned displacements structures located on the second surface.

Conventionally, the reaction solution is brought into a specific opening of the filling unit by means of a suitable tool, for example, a pipette. The transport of liquids into the device is performed via the pressure exerted by the pipette or by means of another pressure-generating tool, like for example a syringe or an automated unit, which is, for example, a functional component of a processing automat.

The filling unit may be developed for manual operation in an ergonomically suitable way. Furthermore, it may have easily accessible additional openings at the outsides for feeding the reactive substances.

In one embodiment, a filling unit furthermore has a suitable fluid interface for penetrating the seal of the chamber body. To this end, specific cannulas are used, which, for example, consist of high-grade steel or polymers and usually have a diameter of 0.05 mm to 2 mm. At least one or more cannulas may be arranged, particularly preferably two, wherein one can be used for filling with a reactive liquid and another for ventilation of the reaction space and for taking up surplus fluids. Such cannulas can be connected with the filling unit in a fixed or an interchangeable manner, wherein preferably a connection, which cannot be detached by the operator, for implementing disposable filling items is implemented.

The filling unit can furthermore comprise a unit for covering the cannulas, so that any possible injury of the operator or contamination of the environment can be avoided after separation of the systems.

The filling unit furthermore may comprise a suitable mechanical interface for snug-fit contacting of the reaction cartridge. Said interface can be developed, for example, in the form of specific snaps. In this manner, penetration of the seal of the chamber body at preferred sites can be ensured.

When processing the reaction cartridge in corresponding processing automats, suitable mechanical measures are to be taken, which allow adjustment and accurate positioning in the devices. This particularly applies to the positioning for the replacement and/or the feeding of liquids and the positioning of the reaction cartridge for detection of the signals after conduction of the reactions in the reaction chamber.

The device or the filling unit can furthermore comprise an integrated waste container, which serves for taking up surplus or dislocated gaseous or liquid media, like for example protective gas fillings or buffers. The waste container can, for example, be filled with a further gaseous, liquid, or solid medium, which binds the liquid or gaseous substances reversibly or irreversibly, like for example cellulose, filter materials, silica gels. In addition, the waste container can have a ventilation opening or can exhibit a negative pressure for improving the filling behavior of the entire unit.

Alternatively, the waste container can also be developed as separate module. In this case, the filling unit is equipped with corresponding fluid interfaces which can correspond to commercial standards, like for example LuerLock, and which lead to the outside. Such interfaces can have a form or force connection with continuing systems.

Figure 22:
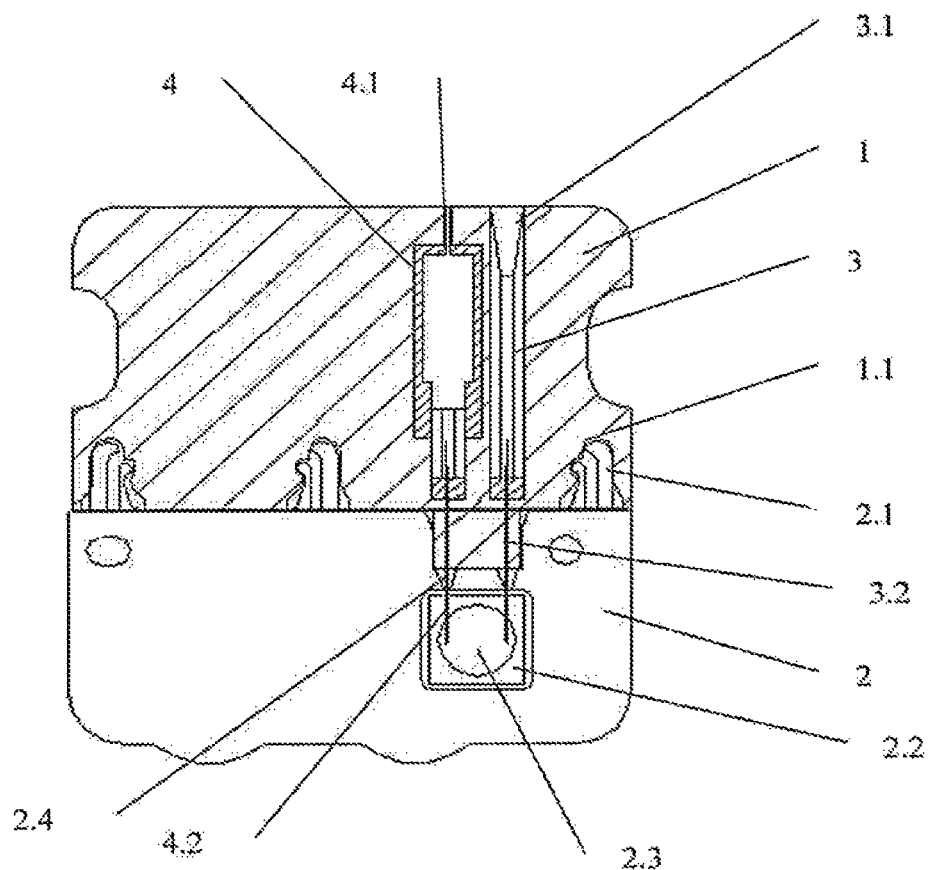
FIG. 22 is a schematic view of a detachable filling unit of a device according to the invention.
Figure 23A:
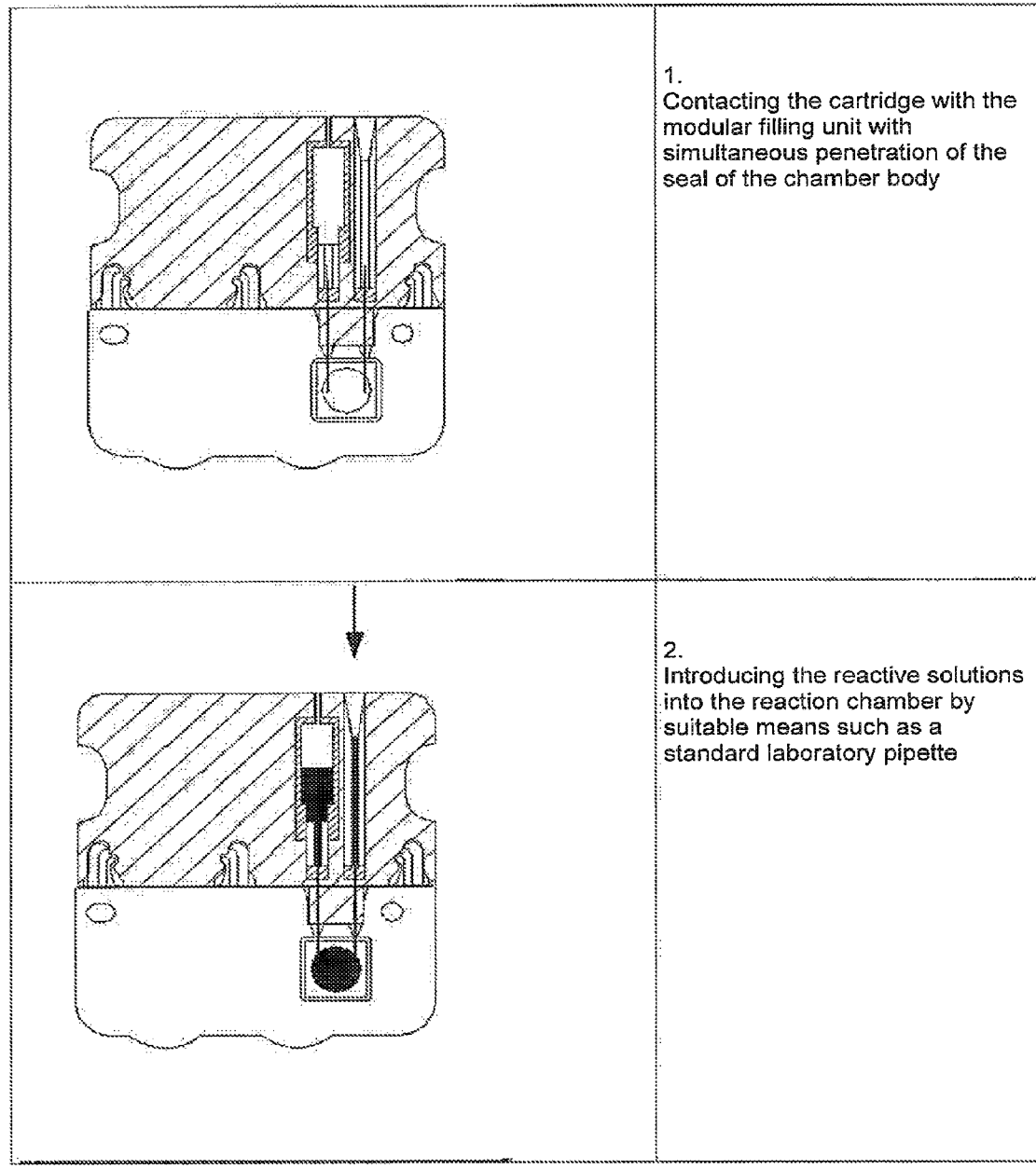
FIGS. 23A-23B illustrate the process of introducing a sample into a reaction cartridge by means of a modular filling unit.
Figure 23B:
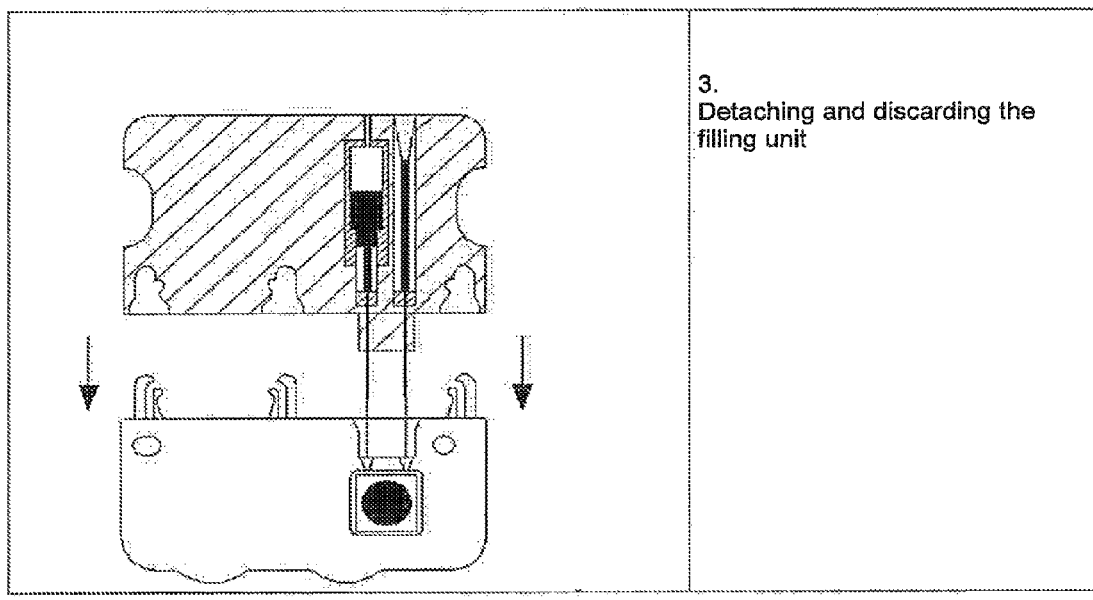

In a first special embodiment, filling is conducted by means of a detachable filling unit having an integrated waste container. In particular, the filling unit serves for non-recurrent filling of the reaction chamber. The filling unit is, for example, developed in such a way that it is plugged or temporarily attached to the cartridge, the samples are fed into the reaction space, and, after filling is completed, the filling unit is again separated from the cartridge and is discarded. In this special first embodiment, the filling unit further comprises an integrated waste container, which can be developed as described above. An example for this embodiment is shown in FIG. 22. The procedure for filling a reaction cartridge by means of a modular filling unit is shown in FIGS. 23A and 23B.

Figure 24:
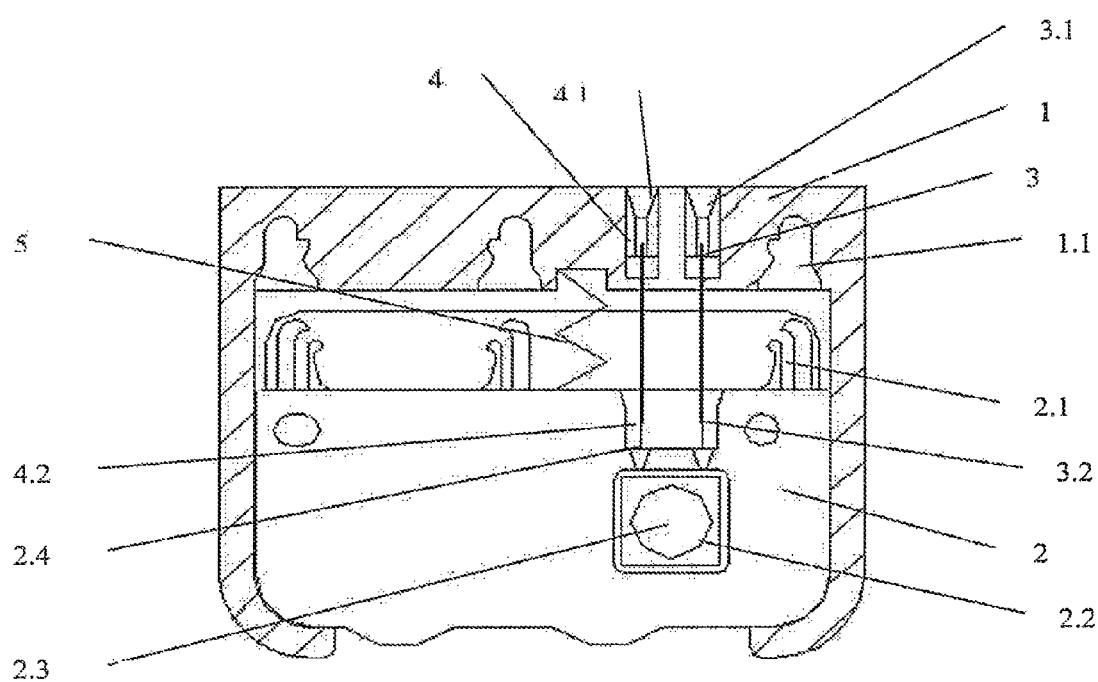
FIG. 24 is a schematic view of an integrated filling unit of a device according to the invention.
Figure 25A:
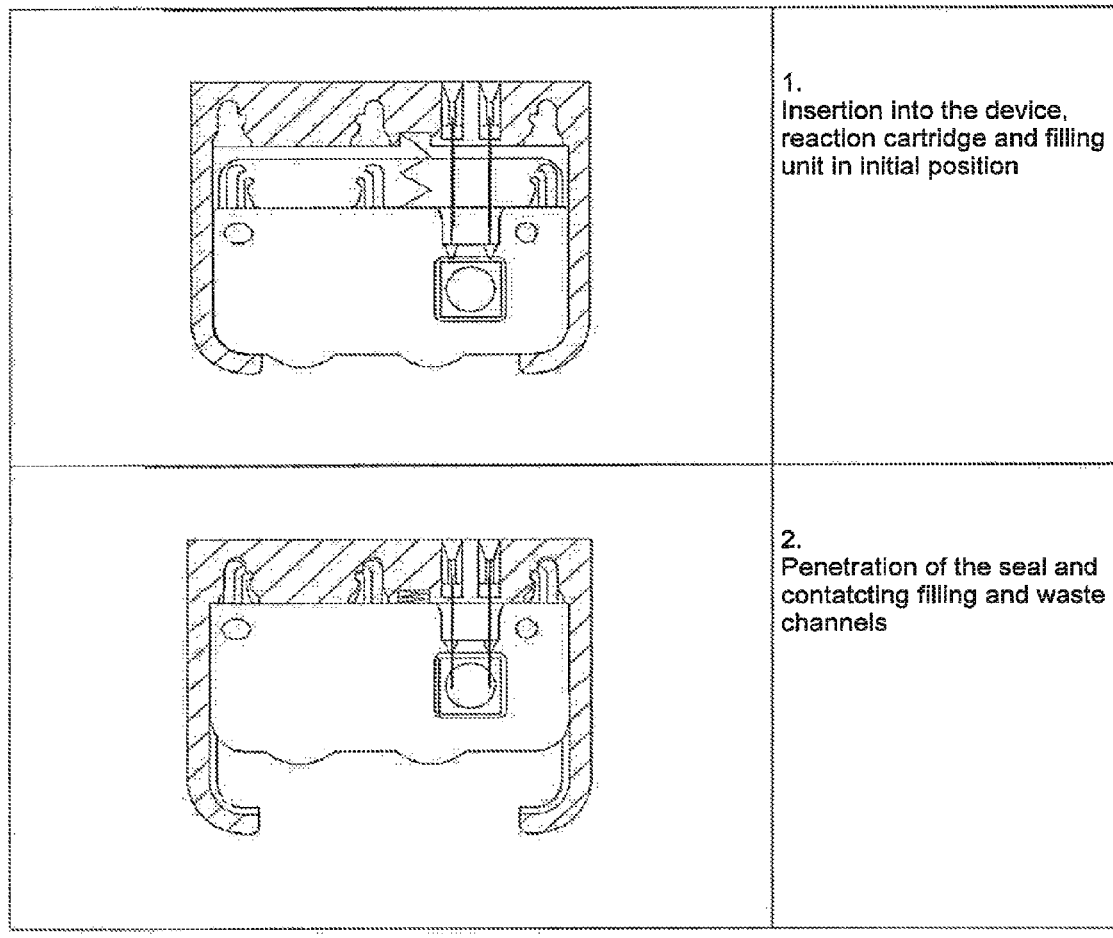
Figure 25B:
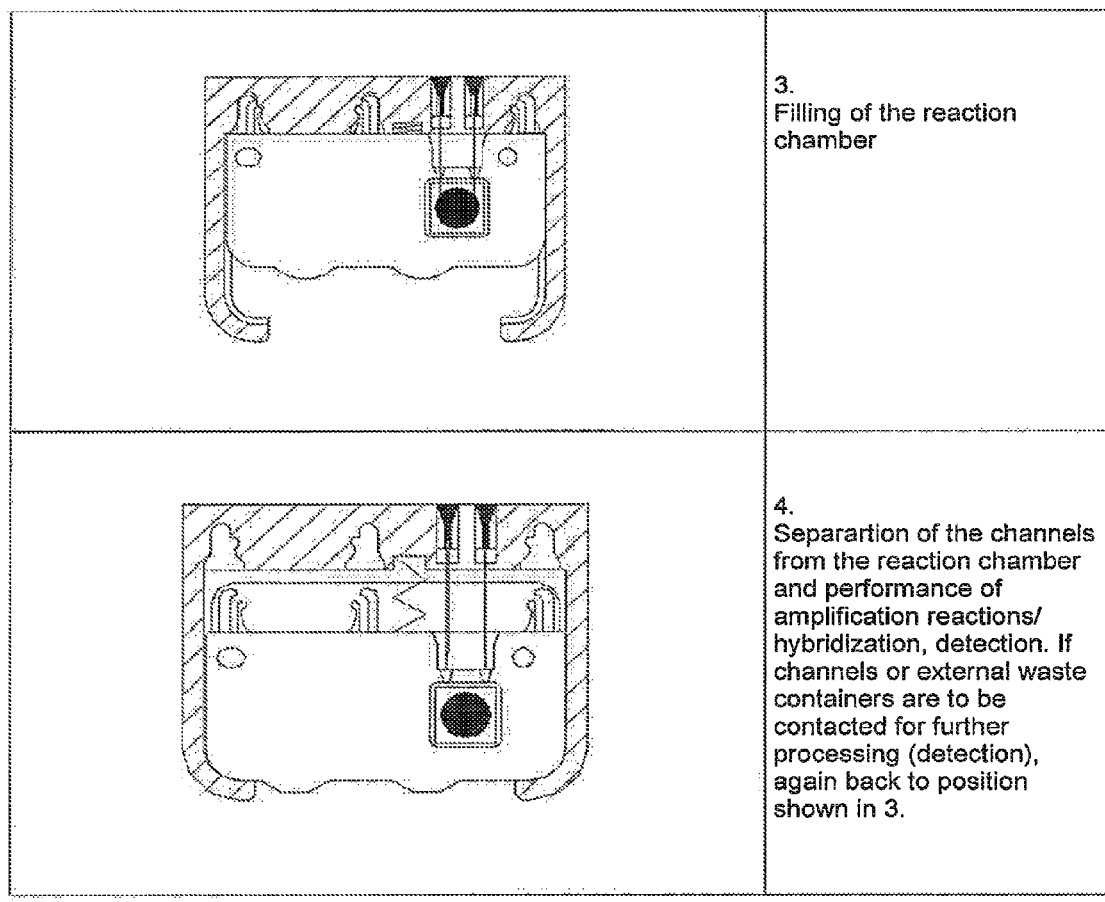

In a second special embodiment, filling is conducted by means of an integrated filling unit. Herein, the filling unit is an integrated component of the reaction cartridge and is therefore not separated from the latter; discarding the tilling unit and the cartridge is conducted simultaneously. Herein, the filling unit may be used for non-recurrent filling of the reaction chamber and possibly for further process-internal fluid steps. In this embodiment, the filling unit furthermore may comprise a technical device, which implements a preferred position of the cannulas in the system, in particular for preventing inadvertent piercing of the cannulas into the seal of the 20 chamber body. It is, however, also conceivable that the cannulas pierce the seal of the chamber body in said preferred position. Said technical device can, for example, be implemented by means of establishing springs, elastic elements, or specific recesses and bumps for implementing a catch. In this embodiment, the filling unit further comprises a filling and waste channel, which comprises corresponding fluid interfaces, which can also correspond to commercial standards, like for example LuerLock, and which lead to the outside. Such interfaces can have a positive or nonpositive interlocking with continuing systems and serve for feeding and/or removing gaseous and/or liquid media. An example for this embodiment is shown in FIG. 24. The procedure for filling a reaction cartridge having an integrated filling unit is shown in FIGS. 25A and 25B.

In a third special embodiment, filling is conducted via an integrated filling unit having an integrated waste container. In said embodiment, the filling unit is an integrated component of the reaction cartridge and is therefore not separated from the latter; tilling unit and cartridge are discarded simultaneously. Herein, the tilling unit is preferably used for non-recurrent filling of the reaction chamber and possibly for further process-internal fluid steps.

Figure 26:
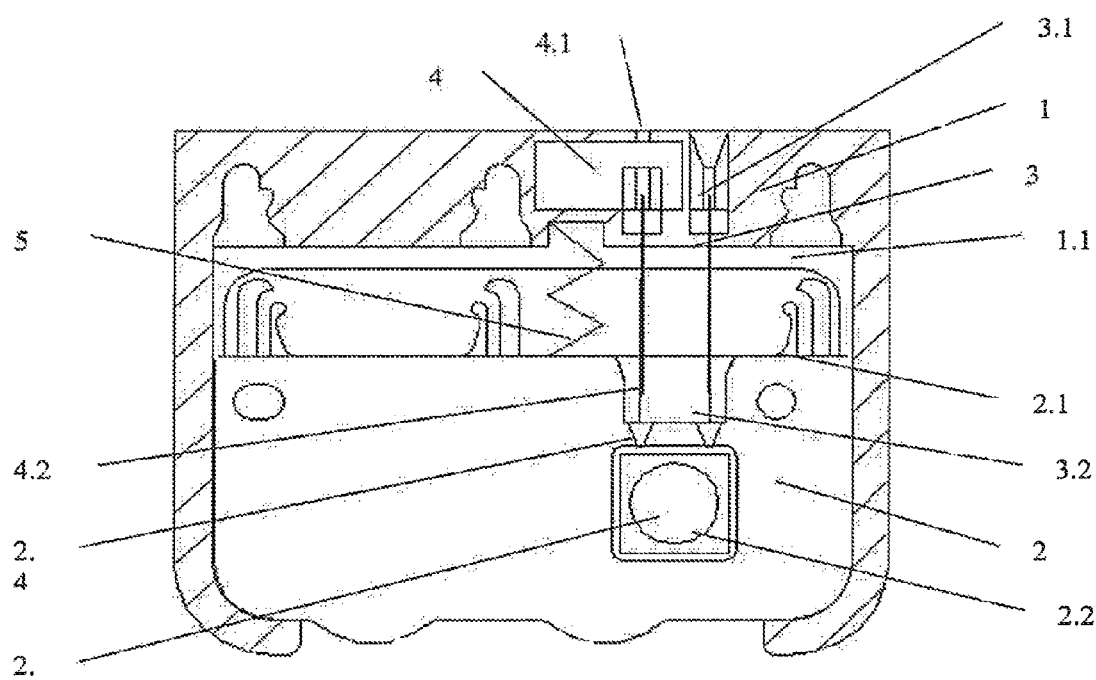
FIG. 26 is a schematic view of an integrated filling unit having an integrated waste container of a device according to the invention.

In this embodiment, the filling unit furthermore may also comprise a technical device, which implements a preferred position of the cannulas in the system, preferably for preventing inadvertent piercing of the cannulas into the seal of the chamber body. It is, however, also conceivable that the cannulas pierce the seal of the chamber body in said preferred position. Said technical device can, for example, be implemented by means of establishing springs, elastic elements, or specific recesses and bumps for implementing a catch. In this embodiment, the tilling unit furthermore comprises an integrated waste container, which can be developed as described above. An example for this embodiment is shown in FIG. 26. The procedure for filling a reaction cartridge with an integrated filling unit and integrated waste container can, for example, be conducted by means of combining the procedures described in FIGS. 23A-B and 25A-B.

Figure 27A:
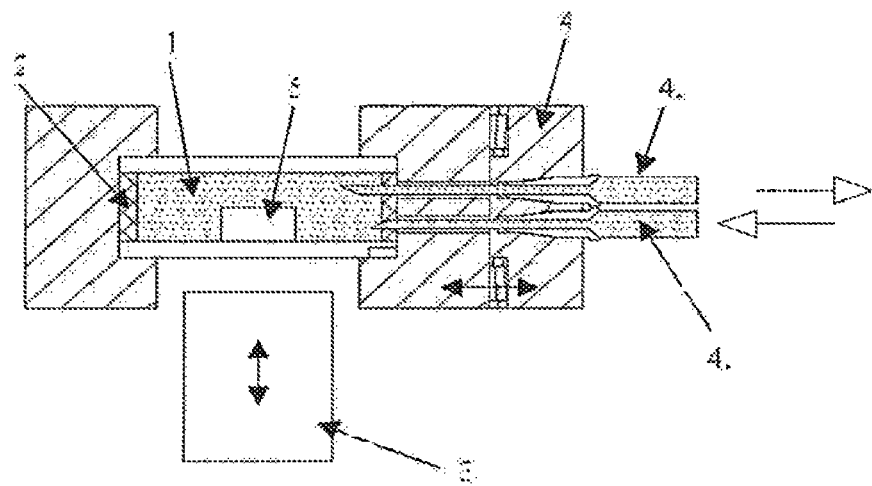
FIG. 27A illustrates the filling of the reaction space when removing the surplus liquid into a waste container or channel
Figure 27B:
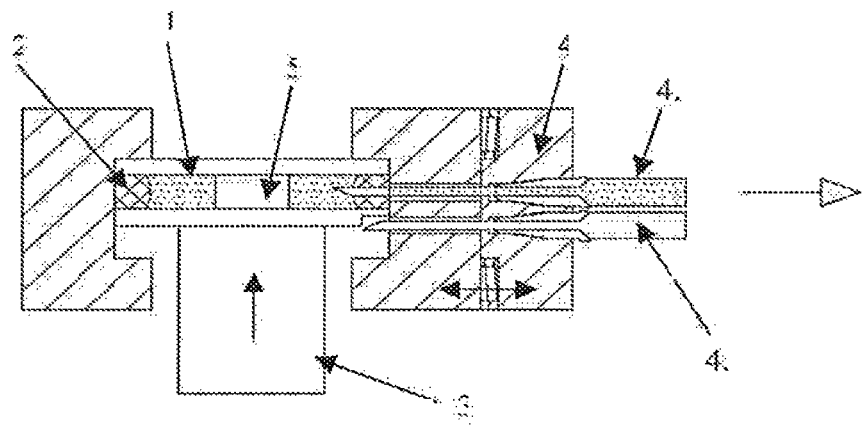
FIG. 27B illustrates the removal of surplus liquid when reducing the reaction space for detection.

In the following, a special embodiment for arranging cannulas for pressure balance during the compression procedure will be described. The cannulas of a filling tool for the cartridge can, for example, be arranged in such a way that both filling in a noncompressed state and transfer of surplus reaction solutions during a compression of the reaction space is possible. This can be achieved by means of adapted construction of the seal and a cannula arrangement, wherein the cannulas may pierce the compensation regions within the reaction chamber. Such an arrangement is particularly suitable, if the surplus volume cannot be taken up by means of a special seal design. An example for a possible vertical cannula arrangement with unaltered form of the seal is shown in FIGS. 27A and 27B.

The device according to the present invention can further comprise a unit, which is connected to the detection system, for controlling the test procedure and/or for processing the signals recorded by means of the detection system. The controlling and/or processing unit can be a micro-controller or an industrial computer. This coupling of detection unit and processing unit, which ensures the conversion of the reaction results to the analysis result, allows, inter alia, the use of the device according to the present invention as hand-held device, for example, in medical diagnostics.

In addition, the device according to the present invention furthermore may have an interface for external computers. Inter alia, this allows the transfer of data for external storage.

In a further embodiment, the device is equipped with a coding, preferably a data matrix and/or a bar code, containing information on the substance library and/or the conduction of the amplification and/or detection reaction. By means of such an individual identification number, the reading or detection device can automatically recognize, which test has been conducted. To this end, a data record containing information on the substance library, the conduction of the detection reaction, and the like is stored in a database when manufacturing the device according to the present invention. Thus, the data record can, in particular, contain information on the layout of the probes on the array and information as to how evaluation is to be conducted in the most advantageous manner. The data record or the data matrix can further contain information on the temperature-time regime of a PCR to be optionally conducted for amplifying the target molecules. The data record thus obtained may preferably be given a number, which is attached to the holder in the form of the data matrix. Via the number recorded in the data matrix, the set data record can then optionally be called when reading out the substance library. Finally, the data matrix can be read out by the temperature controlling or regulating unit and other controllers, like for example a control for filling and unloading of the reaction chamber via the fluid containers, and an automatic conduction of amplification and detection reaction can thus be ensured.

The coding, like a data matrix, does not compellingly have to contain the entire information. It can also simply contain an identification or access number, by means of which the necessary data are then downloaded from a computer or a data carrier.

All preceding embodiments preferably have a displacement structure located on the second surface, as described above, namely on the side of the second surface that is facing the microarray. Thereby, the displacement structure is positioned in such a way that it is located opposite to the microarray and evenly rests on it in the compressed state, wherein during compression the analyte solution being is substantially displaced from the reaction chamber and the surface of the microarray, respectively.

Figure 10:
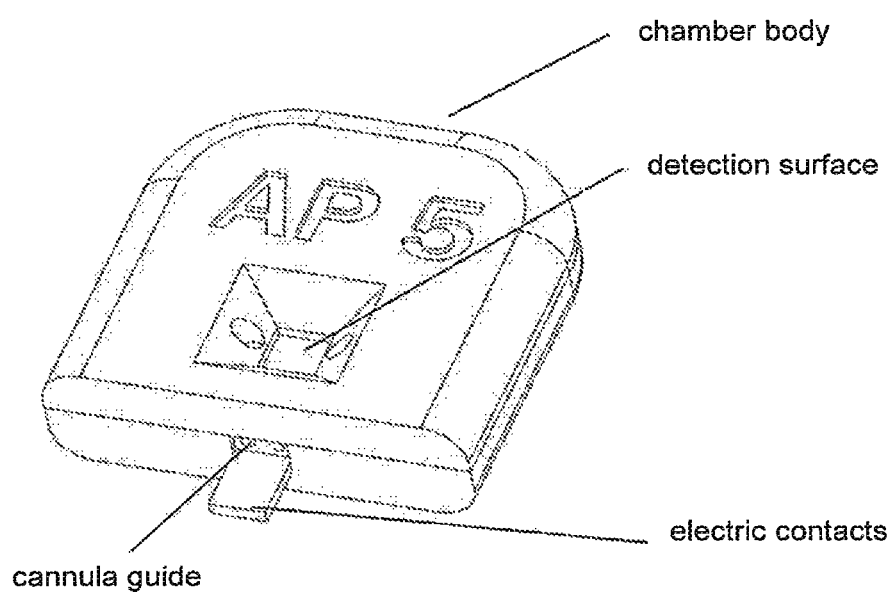
FIG. 10 is a perspective view of a process unit of a device according to the invention.
Figure 11:
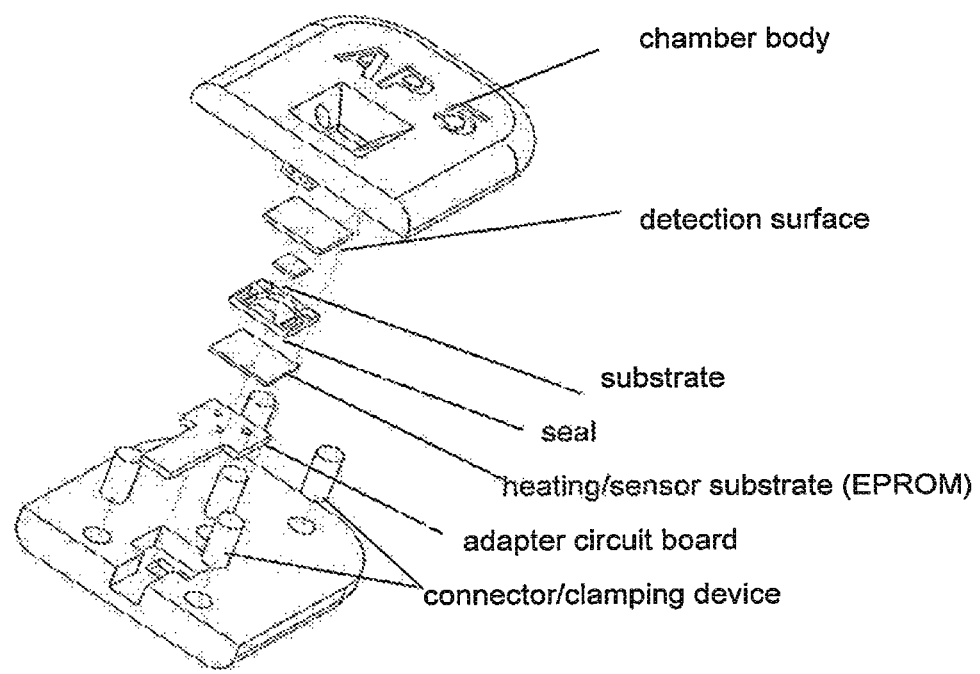
FIG. 11 is an exploded view of the process unit shown in FIG. 10.

The device according to the present invention can be very easily manufactured. In FIG. 3 it is shown that the process unit can consist of only four individual components, which are simply fit into one another. FIGS. 10 and 11 show embodiments, which can also be easily manufactured due to the construction according to the present invention, although they consist of several components. The geometric tolerances of the dimensions of the individual components can be very large with, for example, 1/10 to 2/10 mm, so that, for example, the large-scale injection molding of seal and chamber body can be conducted in a very cost-efficient manner. The low tolerances are facilitated by means of pressing the chip against the detection plane, as thereby the optical path to the detection microscope is hardly influenced by the components of the process unit. The only geometric quantities having a low tolerance are the x,y-position of the chip and the thickness of the detection plane. The variance of the z-position of the chip, however, only plays a subordinate part. Despite these low technical requirements, a focusing device at the optical system, for example a fluorescence detection microscope, is not required. These properties clearly show the suitability of the device according to the present invention for mobile on-site use. The preceding advantages also apply, if the devices have the above-mentioned displacement structure.

In a further aspect of the present invention, a method for qualitatively and/or quantitatively detecting molecular interactions between probe and target molecules is provided, which comprises the following steps:

a) introducing a sample, preferably a sample solution comprising target molecules, into a reaction chamber of a device according to the present invention as described above; and b) detecting an interaction between the target molecules and the probe molecules immobilized on the substrate.

The method according to the present invention may allow the qualitative and/or quantitative detection of molecular interactions between probe and target molecules in a reaction chamber, without necessitating a replacement of the sample or reaction liquids in order to remove a disturbing background after the interaction is completed and before the detection.

Within the scope of the present invention, the detection of an interaction between the probe and the target molecule is usually conducted as follows: Subsequently to fixing the probe or the probes to a specific matrix in the form of a microarray in a predetermined manner or subsequently to providing a microarray, the targets are contacted with the probes in a solution and are incubated under defined conditions. As a result of the incubation, a specific interaction or hybridization occurs between probe and target. The bond occurring herein is significantly more stable than the bond of target molecules to probes, which are not specific for the target molecule.

The detection of the specific interaction between a target and its probe can be performed by means of a variety of methods, which normally depend on the type of the marker, which has been inserted into target molecules before, during or after the interaction of the target molecule with the microarray. Typically, such markers are fluorescent groups, so that specific target/probe interactions can be read out fluorescence-optically with high local resolution and, compared to other conventional detection methods, in particular mass-sensitive methods, with little effort (see, for example, A. Marshall, J. Hodgson, DNA chips: An array of possibilities, Nature Biotechnology 1998, 16, 27-31; G. Ramsay, DNA Chips: State of the art, Nature Biotechnology 1998, 16, 40-44).

Depending on the substance library immobilized on the microarray and the chemical nature of the target molecules, interactions between nucleic acids and nucleic acids, between proteins and proteins, and between nucleic acids and proteins can be examined by means of this test principle (for survey see F. Lottspeich, H. Zorbas, 1998, Bioanalytik, Spektrum Akademischer Verlag, Heidelberg/Berlin, Germany).

Herein, substance libraries, receptor libraries, peptide libraries, and nucleic acid libraries are considered as substance libraries, which can be immobilized on microarrays or chips.

The nucleic acid libraries take by far the most important role. Concerned are microarrays, on which deoxyribonucleic acid (DNA) molecules or ribonucleic acid (RNA) molecules are immobilized.

In one embodiment of the method according to the present invention, before detection the distance between microarray and second surface is kept in a position in step b), which allows processing of the sample solution and/or the interaction between the target molecules and the probe molecules immobilized on the substrate, for example amplification of nucleic acids to be detected and/or hybridization between nucleic acids to be detected and the nucleic acid probes immobilized on the substrate.

In a further embodiment, in step b) the distance between the first and the second surface is altered, preferably reduced. I.e. the detection may be conducted with a reduced distance between at least one area of the first surface, on which the detection has to take place and the probes can be immobilized, respectively, and detection plane. E.g., the distance between first surface and detection plane is about zero during detection.

In one embodiment, the microarray is guided towards the second surface in order to reduce the distance between first and second surface. This may be ensured by pressing the first surface by applying pressure exerted via at least one means for guiding the first surface, for example a tappet, a stencil, a rod, a pin and/or a screw, wherein the pressure point of the means is located particularly below the microarray.

Pressing the microarray towards the second surface or the detection surface can be facilitated in that the first surface is elastically deformable at least in the region below the microarray. Alternatively, the first surface can be developed by means of two superimposed layers, wherein one outer layer of the two superimposed layers has a cut-out at least in the region below the microarray, and an inner layer of the two superimposed layers is formed by an elastic seal. Pressure is then exerted on the inner layer in the area of the cut-out by the means for guiding the first surface.

The means for guiding the first surface, for example a pin, a stencil, a rod, a tappet and/or a screw, cannot only serve for exerting a pressure on the first surface, however. In the event that bubbles should form on the DNA chip, which would impede the detection, these bubbles can be removed by means of agitation by the means for guiding the first surface, for example by means of a vibration frequency of about 20 Hz applied to the first surface, in particular in the form of an elastic membrane.

All preceding embodiments preferably have a displacement structure located on the second surface, as described above, namely on the side of the second surface that is facing the microarray. Thereby, the displacement structure is positioned in such a way that it is located opposite to the microarray and evenly rests on it in the compressed state, wherein during compression the analyte solution being is substantially displaced from the detection and/or reaction chamber and the surface of the microarray, respectively.

Furthermore, there is often the problem that the interaction, for example the hybridization, at the chip surface takes a very long time. Among other reasons, this is due to the fact that the speed of interaction or hybridization is determined by diffusion. Preferably, the interaction or hybridization speed can be increased by means of agitation via the means for guiding the first surface, for example by means of a vibration frequency of about 20 Hz applied to the first surface, in particular in the form of an elastic membrane, as the agitation or vibration leads to mixing in the reaction chamber.

In a further embodiment, the second surface is guided towards the first surface in order to reduce the distance between the microarray and the second surface. In particular, this can be ensured in that the second surface is guided toward the first surface by means of pressure exerted on the second surface by the spacer.

In a further embodiment, the first surface is guided towards the second surface and the second surface is guided towards the first surface in order to reduce the distance between the microarray and the second surface. In all preceding embodiments, the above-described displacement structures may be present.

In the following, further embodiments for guiding the first surface relatively to the second surface or the second surface relatively to the first surface will be described.

Said embodiments are not only suitable for positioning the first surface or the region, onto which probes can be immobilized or the detection of the targets can take place, relatively to the second surface or the detection surface, but can, in particular, also be used for moving the probe array relatively to the detection surface. By means of such a motion, for example an agitation of the solution in the reaction chamber can be achieved.

In one embodiment, the probe array is moved relatively to the detection surface or moved within the chamber by means of a magnetic field. The substrate and/or the second surface, for example, contain a magnetic material or a component, whereto a magnetic material has been added, and/or is mounted in a holder consisting of an entirely or partially magnetic material. It can further be preferred that the probe array and/or the second surface are moved passively by moving a magnetic body, which is arranged below the respective surface and is, for example, connected with said surface, by means of a magnetic field.

In a further embodiment, the substrate is moved and/or positioned relatively to the detection surface by means of gravitational impact.

In a further embodiment, the probe array is moved and/or positioned relatively to the detection surface by means of a stream generated in the reaction chamber. To this end, the device can, for example, be developed in such a way that, in case the probe array is surrounded by a liquid stream, a negative pressure is generated at one side of the reaction chamber and a positive pressure is generated at the opposite side, which leads to movement of the probe array in the reaction chamber. Such a stream can, for example, be implemented by means of thermal convection, which is caused by local temperature differences in the chamber.

In a further embodiment, the substrate is moved and/or positioned relatively to the detection surface by means of impact of an electric field.

In a further embodiment, a gas bubble is generated below the probe array by means of local overheating, due to which the chip is moved in the chamber or is guided toward the detection surface. In the preceding embodiments, the above-mentioned displacement structures may be present as well.

By means of reducing the distance between the microarray and the second surface prior to detection, the sample solution preferably is substantially removed from the region between microarray and detection surface. Thereby, background signals, which are caused by labeled molecules, which are not bound to the array surface, for example by labeled primers and/or labeled target nucleic acids, which are not bound to the array surface, are reduced.

Thus, in the detection of step b), the distance between the microarray and the second surface is preferably altered in such a way that the sample solution between the microarray and the second surface is substantially removed. Then, the microarray is placed substantially within the detection plane and an interfering background is almost entirely avoided. This also applies in the presence of a displacement structure.

In a further alternative embodiment, the microarray rests evenly on the second surface forming the detection plane already in the original state of the device and is not only brought into the detection plane by means of guiding the first surface toward the second surface and/or guiding the second surface toward the first surface. In this embodiment, the first surface is not moistened by the sample solution during the processing steps. For conducting the interaction reaction, for example a hybridization, the first surface, which may be made of an elastic material, for example an elastic membrane, is guided away from the detection surface. Thereby, the chip surface is moved away from the detection surface and is moistened by the sample solution. The interaction, for example a hybridization, can take place. For conducting the detection and further processing, the first surface, for example in the form of an elastic membrane, is released again, due to which it leaps back to its originally adjusted position, which can be accelerated by means of pressure exerted by a means for guiding the first surface, for example a pin, a stencil, a rod, a screw and/or a tappet. Thereby, the microarray is pressed towards the detection plane again and the detection can be conducted without having background. This also applies in the presence of a displacement structure.

In a further embodiment of the method according to the present invention, a device according to the present invention, as described above, is used, the first surface of which is developed in a pivotable manner around a rotation axis.

In a first position, which is also referred to as initial position, the surface of the microarray located on the first flanking portion rests substantially evenly on the second surface, i.e. the substrate surface with the probe molecules immobilized thereon is substantially not moistened by the sample solution. In the space formed in the first position between the second flanking portion of the first surface and the second surface, i.e. the processing chamber, the processing of the reaction solution preferably occurs in this first position, that is in particular in particular purification, concentration, washing, rinsing and/or amplification steps.

Subsequently, the pivotable first surface is brought to a second position, wherein the first surface is arranged relatively to the second surface at an angle other than 180°, preferably at an angle of 45°. This may be conducted by means of traction exerted on the first flanking portion of the first surface and/or pressure exerted on the second flanking portion of the first surface by means of a means for guiding the first surface, as described above. By means of guiding the first surface to the second position, the microarray is guided away from the second surface and the sample solution penetrates the cavity forming between microarray and second surface. The probe molecules immobilized on the substrate of the microarray are freely accessible for the target molecules present in the sample solution, so that an interaction reaction between probe and target molecules can occur. In this embodiment of the method according to the present invention, pressure and/or traction exerted on the first surface has the advantage that, in this manner, the sample solution is moved and thus the interaction reaction can be accelerated.

For conducting the detection and, optionally, further processing, the pivotable first surface is guided back to the first position, for example by means of pressure exerted on the first flanking portion of the first surface and/or traction exerted on the second flanking portion of the first surface or, in the case of elastic development of the first surface, by means of releasing the first flanking portion. Now, the mentioned region of the first surface again rests essentially evenly on the second surface, so that the sample solution between the second surface and the microarray is essentially displaced in this position and an essentially background-free detection can take place. The preceding embodiment may also comprise a displacement structure.

The targets to be examined can be present in any kind of sample, preferably in a biological sample.

The targets may be isolated, purified, copied, and/or amplified before their detection and quantification by means of the method according to the present invention.

The method according to the present invention may further allow the amplification and the qualitative and/or quantitative detection of nucleic acids in a reaction chamber, wherein the detection of molecular interactions or hybridizations can be conducted after completion of a cyclic amplification reaction without necessitating replacement of the sample or reaction liquids. The method according to the present invention further also ensures a cyclic detection of hybridization events in an amplification, i.e. a detection of the hybridization even during the cyclic amplification reaction. Finally, with the aid of the method according to the present invention, the amplification products can be quantified during the amplification reaction and after completion of the amplification reaction.

Usually, the amplification is performed by means of conventional PCR methods or by means of a method for the parallel performance of amplification of the target molecules to be analyzed by means of PCR and detection by means of hybridization of the target molecules with the substance library support, as is described above.

In a further embodiment, the amplification is performed as a multiplex PCR in a two-step process (see also WO 97/45559). In a first step, a multiplex PCR is performed by means of using fusion primers, whose 3'-ends are gene specific and whose 5'-ends represent a universal region. The latter is the same in all forward and reverse primers used in the multiplex reaction. In this first stage, the amount of primer is limiting. Hereby, all multiplex products can be amplified until a uniform molar level is achieved, given that the number of cycles is adequate for reaching primer limitation for all products. In a second stage, universal primers identical to the 5'-regions of the fusion primers are present. Amplification is performed until the desired amount of DNA is obtained.

In a further embodiment of the method according to the present invention, detection is performed during the cyclic amplification reaction and/or after completion of the cyclic amplification reaction. Preferably, detection is performed during the amplification reaction, in every amplification cycle. Alternatively, detection can also be determined in every second cycle or every third cycle or in any arbitrary intervals.

In the conduction of a linear amplification reaction, wherein the target amount increases by a certain amount with each step, or an exponential amplification reaction, for example a PCR, wherein the DNA target amount multiplies with each step, in the process unit, the chip can thus be pressed towards the detection plane after every amplification step and therefore the detection can be conducted. It is thus possible to perform on-line surveillance of the amplification reaction. In particular in the case of non-linear amplification reactions, it is thereby possible to determine the initial concentration of the DNA target amount.

In this manner, the number of amplification steps can furthermore be optimized on-line. As soon as the DNA target amount has reached a specific concentration, the amplification is discontinued. If the initial target concentration is low, the number of amplification steps is increased in order to be able to conduct an assured analysis of the products. In the case of reduced reaction time of positive controls, the analysis process can be discontinued very early.

The chemicals necessary for conducting an amplification reaction, like for example polymerase, buffer, magnesium chloride, primers, labeled, in particular fluorescence-labeled primers, dNTPs and the like, can be provided in the reaction chamber, for example in freeze-dried form.

Usually, the cyclic amplification reaction is a PCR. In a PCR, three temperatures for each PCR cycle are usually passed through. Preferably, the hybridized nucleic acids detach from the microarray at the highest temperature, i.e. the denaturation temperature. A preferred value for the denaturation temperature is 95° C. Therefore, a hybridization signal, which serves as zero value or reference value for the nucleic acids detected in the respective PCR cycle, can be determined at this denaturation temperature.

At the temperature following in the PCR cycle, an annealing temperature of, for example, about 60° C., a hybridization between the nucleic acids to be detected and the nucleic acids immobilized on the substrate of the microarray is facilitated. Therefore, in one embodiment of the method according to the present invention, the detection of target nucleic acids present in a PCR cycle is performed at the annealing temperature.

In order to enhance the sensitivity of the method according to the present invention, it can further be advantageous to lower the temperature below the annealing temperature, so that the detection is preferably performed at a temperature below the annealing temperature of an amplification cycle. For example, the detection can be performed at a temperature in a range of 25° C. to 50° C. and preferably in a range of 30° C. to 45° C.

In a further alternative embodiment of the method according to the present invention, the hybridization between nucleic acids to be detected and the nucleic acids immobilized on the substrate of the microarray is at first performed at a low temperature, in order to subsequently raise the hybridization temperature. Such an embodiment has the advantage that the hybridization time is reduced compared to hybridizations at temperatures of more than 50° C. without losing specificity in the interactions.

If the zero value or reference value determined at denaturation temperature is subtracted from the measured value determined at or below the annealing temperature, a measured result free of disturbances, in which fluctuation and drift are eliminated, can be obtained.

Usually, the target molecules to be detected are equipped with a detectable marker. In the method according to the present invention, the detection is thus preferably conducted by means of equipping the bound targets with at least one label, which is detected in step b).

As already mentioned above, the label coupled to the targets or probes may be a detectable unit or a detectable unit coupled to the targets or probes via an anchor group. With respect to the possibilities for detection or labeling, the method according to the present invention is very flexible. Thus, the method according to the present invention is compatible with a variety of physical, chemical, or biochemical detection methods. The only prerequisite is that the unit or structure to be detected can directly be coupled or can be linked via an anchor group, which can be coupled with the oligonucleotide, to a probe or a target, for example an oligonucleotide.

The detection of the label can be based on fluorescence, magnetism, charge, mass, affinity, enzymatic activity, reactivity, a gold label, and the like. Thus, the label can, for example, be based on the use of fluorophore-labeled structures or components. In connection with fluorescence detection, the label can be an arbitrary dye, which can be coupled to targets or probes during or after their synthesis. Examples are Cy dyes (Amersham Pharmacia Biotech, Uppsala, Sweden), Alexa dyes, Texas Red, Fluorescein, Rhodamin (Molecular Probes, Eugene, Oreg., USA), lanthanides like samarium, ytterbium, and europium (EG&G, Wallac, Freiburg, Germany).

In some embodiments, said detectable marker is a fluorescence marker. As already mentioned above, the use of the device according to the present invention in the method according to the present invention ensures the detection of the fluorescence markers by means of a fluorescence microscope without autofocus, for example a fluorescence microscope with fixed focus.

Apart from fluorescence markers, luminescence markers, metal markers, enzyme markers, radioactive markers, and/or polymeric markers can also be used within the scope of the present invention as labeling and/or detection unit, which is coupled to the targets or the probes.

Likewise, a nucleic acid, which can be detected by means of hybridization with a labeled reporter (sandwich hybridization), can be used as label (tag). Diverse molecular biological detection reactions like primer extension, ligation, and RCA are used for the detection of the tag.

In an alternative embodiment of the method according to the present invention, the detectable unit is coupled with the targets or probes via an anchor group. Preferably used anchor groups are biotin, digoxigenin, and the like. In a subsequent reaction, the anchor group is converted by means of specifically binding components, for example streptavidin conjugates or antibody conjugates, which in turn are detectable or trigger a detectable reaction. With the use of anchor groups, the conversion of the anchor groups to detectable units can be performed before, during, or after the addition of the sample comprising the targets, or, optionally, before, during, or after the cleavage of a selectively cleavable bond in the probes. Such selectively cleavable bonds in the probes are, for example, described in the International Patent Application WO 03/018838, the relevant contents of which are hereby explicitly referred to.

According to the present invention, labeling can also be performed by means of interaction of a labeled molecule with the probe molecules. For example, labeling can be performed by means of hybridization of an oligonucleotide labeled as described above with an oligonucleotide probe or an oligonucleotide target.

Further labeling methods and detection systems suitable within the scope of the present invention are described, for example, in Lottspeich and Zorbas, Bioanalytik, Spektrum Akademischer Verlag, Heidelberg, Berlin, Germany 1998, chapter 23.3 and 23.4.

In a further embodiment of the method according to the present invention, detection methods are used, which in result yield an adduct having a particular solubility product, which leads to a precipitation. For labeling, in particular substrates or educts are used, which can be converted to a hardly soluble, usually stained product. In this labeling reaction, for example, enzymes can be used, which catalyze the conversion of a substrate to a hardly soluble product. Reactions suitable for leading to a precipitation at the array elements as well as possibilities for the detection of the precipitation are, for example, described in the International Patent Application WO 00/72018 and in the International Patent Application WO 02/02810, whose relevant contents are hereby explicitly referred to.

In a further embodiment of the method according to the present invention, the bound targets are equipped with a label catalyzing the reaction of a soluble substrate or educt to form a hardly soluble precipitation at the array element, where a probe/target interaction has occurred or acting as a crystal nucleus for the conversion of a soluble substrate or educt to a hardly soluble precipitation at the array element, where a probe/target interaction has occurred.

In this manner, the use of the method according to the present invention allows for the simultaneous qualitative and quantitative analysis of a variety of probe/target interactions, wherein several array elements having a size of ≤1000 µm, preferably of ≤100 µm, and particularly preferably of ≤50 µm may be realized.

The use of enzymatic labels is known in immunocytochemistry and in immunological tests based on microtiter plates (see E. Lidell and I. Weeks, Antibody Technology, BIOS Scientific Publishers Limited, 1995). Thus, for example, enzymes catalyze the conversion of a substrate to a hardly soluble, usually stained product.

In one embodiment, the reaction leading to precipitation formation at the array elements is a conversion of a soluble substrate or educt to a hardly soluble product, catalyzed by an enzyme. In a special embodiment, the reaction leading to precipitation formation at the array elements is an oxidation of 3,3',5,5'-tetramethylbenzidine, catalyzed by a peroxidase.

For the oxidation of 3,3',5,5'-tetramethylbenzidine, horseradish peroxidase may be used However, additional peroxidases are known by the skilled person, which can be used for the oxidation of 3,3',5,5'-tetramethylbenzidine.

3,3',5,5'-tetramethylbenzidine, when exposed to a peroxidase, is assumed to be oxidized in a first step to form a blue-stained radical cation (see, for example, Gallati and Pracht, J. Clin. Chem. Clin. Biochem. 1985, 23, 8, 454). This blue-stained radical cation is precipitated in form of a complex by using a polyanion, such as dextran sulfate. The precipitation reaction by means of peroxidase-catalyzed oxidation of 3,3',5,5'-tetramethylbenzidine is, for example, described in EP 0 456 782.

Without any intention of being complete, the following Table 1 summarizes several reactions that are suitable to cause a precipitation at array elements, where an interaction between target and probe has occurred:

TABLE 1

| catalyst or crystal nucleus | substrate or educt |
|---|---|
| horseradish peroxidase | DAB (3,3'-diaminobenzidine) |
| | 4-CN (4-chloro-1-naphthol) |
| | AEC (3-amino-9-ethylcarbazole) |
| | HYR (p-phenylenediamine-HCl and pyrocatechol) |
| | TMB (3,3',5,5'-tetramethylbenzidine) |
| | naphthol/pyronin |
| alkaline phosphatase | brom-chlor-indolyl-phosphate (BCIP) and nitroblue tetrazolium (NBT) |
| glucose oxidase | t-NBT and m-PMS (nitroblue tetrazolium chloride and phenazine methosulfate |
| gold particles | silver nitrate |
| | silver tartrate |

The detection of probe/target interactions via insoluble precipitates is also described in WO 02/02810.

In the following, embodiments of the present invention are described, which can serve to overcome problems likely to arise in the detection of molecular interactions on solid supports, such as for preventing the possible formation of Newton's rings between detection surface and probe array.

The manifestation of Newton's rings is essentially determined by the type of illumination, the wavelength of the light used for detection, the distance between detection plane and probe array, and the refraction index of the solution located in the chamber. Such Newton's rings can, for example, be prevented by means of altering the wavelength of the light used for detection, by using a solution having the same or a similar refraction index as the detection surface and/or the probe array, and/or by using an immersion liquid between detection surface and probe array.

Furthermore, Newton's rings can be prevented by means of applying spacers on the chip or on the regions on the side of the detection surface facing the chip.

Furthermore, Newton's rings can be prevented by means of applying the probe array onto a rough support surface.

Furthermore, Newton's rings can be prevented by means of applying the probe array onto a light-absorbing surface.

As a further possibility the contact pressure by which the first surface is guided relatively to the detection surface may be permanently varied during detection. Thus, the thickness of the gap between chip and detection surface, and therefore also the position of Newton's rings, is altered. By integrating the fluorescence signal to be detected over time, a falsification of the measured values of the spots in relation to each other is prevented.

It is a further possibility of preventing Newton's rings to use several light sources from different directions for illuminating and therefore agitating the fluorophores of the bound targets.

Background fluorescence caused by fluorophores of unbound targets in the displaced liquid can lead to falsification of the signal detected. This can preferably be prevented by means of using an aperture, which is, for example, mounted on the detection surface or the chip and/or the regions around the chip or the imaging optics, and is configured in such a way that only the surface of the probe array is illuminated or imaged.

By using appropriate light sources, such as lasers, illumination may be inhomogenous due to coherence of the light. Such inhomogeneities can be reduced or prevented by using waveguides and/or combining filters and/or light of different wavelengths. Likewise, movement of the light source in order to eliminate such effects is also conceivable.

By using an organic or inorganic light-absorbing layer, which is non-fluorescent in the selected wavelength range, on the substrate of the probe array, the fluorescence background signal caused by the array support and/or elements located behind the same, can be reduced or prevented. Preferably, a black chromium layer is employed as protective layer.

In all above-described embodiments of the inventive method, a pre-amplification of the material to be analyzed is not required. From the sample material extracted from bacteria, blood, or other cells, specific partitions can be amplified using a PCR (polymerase chain reaction), in particular in the presence of the inventive device or the substance library support, as is described in DE 102 53 966, and hybridized to the support. This represents a substantial reduction of labor effort.

Thus, the method according to the present invention is suitable for the parallel amplification of the target molecules to be analyzed by PCR and the detection by hybridization of the target molecules with the substance library support. There, the nucleic acid to be detected is first amplified by PCR, wherein at least one competitor inhibiting the formation of one of the two template strands amplified by PCR may be initially added to the reaction. In particular, a DNA molecule, which competes with one of the primers used for the PCR amplification of the template for binding to the template and which can not be extended enzymatically, may be added to the PCR. The single-stranded nucleic acid molecules amplified by PCR are then detected by means of hybridization with a complementary probe. Alternatively, the nucleic acid to be detected is first amplified using a surplus of single strand by PCR and is detected by means of a subsequent hybridization with a complementary probe, wherein a competitor, which is a DNA molecule or a molecule of a nucleic acid analog capable of hybridizing to one of the two strands of the template but not to the region detected by hybridization to a probe and which cannot be enzymatically extended, is initially added to the PCR reaction.

Any molecule causing a preferred amplification of only one of the two template strands present in the PCR reaction can be used as competitor in the PCR. Thus, according to the present invention, competitors can be proteins, peptides, DNA ligands, intercalators, nucleic acids or analogs thereof. Proteins or peptides, which are capable of binding single-stranded nucleic acids with sequence specificity and which have the above-defined properties, are preferably used as competitors. Particularly preferably, nucleic acid molecules and nucleic acid analog molecules are used as to break open secondary structures.

The formation of one of the two template strands is substantially inhibited by the initial addition of the competitor to the PCR during amplification. "Substantially inhibited" means that a surplus of single strand and a amount of the other template strand sufficient to allow an efficient detection of the amplified strand by means of hybridization are produced in the PCR. Therefore, the amplification does not follow exponential kinetics of the form $2^n$ (with n=number of cycles), but rather attenuated amplification kinetics of the form $<2^n$.

The single strand surplus obtained by means of the PCR in relation to the non-amplified strand may have the factor 1.1 to 1,000, the factor 1.1 to 300, the factor 1.1 to 100, the factor 1.5 to 100, the factor 1.5 to 50, the factor 1.5 to 20, or the factor 1.5 to 10.

Typically, the function of a competitor will be to bind selectively to one of the two template strands and therefore to inhibit the amplification of the corresponding complementary strand. Therefore, competitors can be single-stranded DNA- or RNA-binding proteins having specificity for one of the two template strands to be amplified in a PCR. They can also be aptamers sequence-specifically binding only to specific regions of one of the two template strands to be amplified.

In some embodiments, nucleic acids or nucleic acid analogs are used as competitors. Usually, the nucleic acids or nucleic acid analogs will act as competitors of the PCR either by competing with one of the primers used for the PCR for the primer binding site or by being capable of hybridizing with a region of a template strand to be detected due to a sequence complementarity. This region is not the sequence detected by the probe. Such nucleic acid competitors are enzymatically not extendable.

The nucleic acid analogs can, for example, be so-called peptide nucleic acids (PNA). However, nucleic acid analogs can also be nucleic acid molecules, in which the nucleotides are linked to one another via a phosphothioate bond instead of a phosphate bond. They can also be nucleic acid analogs, wherein the naturally occurring sugar components ribose or deoxyribose have been replaced with alternative sugars, like for example arabinose or trehalose or the like. Furthermore, the nucleic acid derivative can be "locked nucleic acid" (LNA). Further nucleic acid analogs are known to the person skilled in the art.

Preferably, DNA or RNA molecules, and particularly preferably DNA or RNA oligonucleotides or their analogs, are used as competitors.

Depending on the sequence of the nucleic acid molecules or nucleic acid analogs used as competitors, the inhibition of the amplification of one of the two template strands within the scope of the PCR reaction is based on different mechanisms. In the following, this is exemplarily discussed for a DNA molecule.

If, for example, a DNA molecule is used as competitor, it may have a sequence, which is at least partially identical to the sequence of one of the primers used for the PCR such that a specific hybridization of the DNA competitor molecule with the corresponding template strand is possible under stringent conditions. Since, within the present invention, the DNA molecule used for competition in this case is not extendable by means of a DNA polymerase, the DNA molecule competes with the respective primer for binding to the template during the PCR reaction. Depending on the ratio of the DNA competitor molecule and the primer, the amplification of the template strand defined by the primer can thus be inhibited in such a way that the production of this template strand is significantly reduced. Thereby, the PCR proceeds according to exponential kinetics higher than would be expected with the amounts of competitors used. In this manner, a single strand surplus emerges in an amount, which is sufficient for the efficient detection of the amplified target molecules by means of hybridization.

In this embodiment, the nucleic acid molecules or nucleic acid analogs used for competition must not be enzymatically extendable. "Enzymatically not extendable" means that the DNA or RNA polymerase used for the amplification cannot use the nucleic acid competitor as primer, i.e. it is not capable of synthesizing the corresponding opposite strand of the template 3' from the sequence defined by the competitor.

Alternatively to the above-depicted possibility, the DNA competitor molecule can also have a sequence complementary to a region of the template strand to be detected, which is not addressed by one of the primer sequences and which is enzymatically not extendable. In a PCR, the DNA competitor molecule will then hybridize to this template strand and correspondingly block the amplification of this strand.

The person skilled in the art knows that the sequences of DNA competitor molecules or, in general, nucleic acid competitor molecules can be selected appropriately. If the nucleic acid competitor molecules have a sequence, which is not substantially identical to the sequence of one of the primers used for the PCR, but is complementary to another region of the template strand to be detected, this sequence is to be selected in such a way that it does not fall within the region of the template sequence, which is detected with a probe within the scope of the hybridization. This is necessary because there does not have to occur a processing reaction between the PCR and the hybridization reaction. If a nucleic acid molecule, which falls within the region to be detected, were used as competitor, it would compete for binding to the probe against the single-stranded target molecule.

Such competitors preferably hybridize close to the template sequence detected by the probe. According to the present invention, the position specification "close to" is to be understood in the same way as given for agents breaking open secondary structures. However, the competitors according to the present invention can also hybridize in the immediate proximity of the sequence to be detected, i.e. at exactly one nucleotide's distance from the target sequence to be detected.

If nucleic acids or nucleic acid analogs that are not enzymatically extendable are used as competing molecules, they are to be selected with respect to their sequence and structure in such a way that they cannot be enzymatically extended by DNA or RNA polymerases. Preferably, the 3'-end of a nucleic acid competitor is designed in such a way that it has no complementarity to the template and/or has at its 3'-end a substituent other than the 3'-OH group.

If the 3' end of the nucleic acid competitor has no complementarity to the template, regardless of whether the nucleic acid competitor binds to one of the primer binding sites of the template or to one of the sequences of the template to be amplified by means of the PCR, the nucleic acid competitor cannot be extended by the conventional DNA polymerases due to the lack of base complementarity at its 3'-end. This type of non-extensibility of nucleic acid competitors by DNA polymerases is known to the person skilled in the art. Preferably, the nucleic acid competitor has no complementarity to its target sequence at its 3'-end with respect to the last 4 bases, particularly preferably to the last 3 bases, in particular preferably to the last 2 bases, and most preferably to the last base. In the mentioned positions, such competitors can also have non-natural bases, which do not allow hybridization.

Nucleic acid competitors, which are enzymatically not extendable, can also have a 100% complementarity to their target sequence, if they are modified in their backbone or at their 3'-end in such a way that they are enzymatically not extendable.

If the nucleic acid competitor has at its 3'-end a group other than the OH group, these substituents are preferably a phosphate group, a hydrogen atom (dideoxynucleotide), a biotin group, or an amino group. These groups cannot be extended by conventional polymerases.

The use of a DNA molecule, which competes with one of the two primers used for the PCR for binding to the template, and which was provided with an amino linkage at its 3'-end during chemical synthesis, as a competitor in such a method is particularly preferred. Such competitors can have 100% complementary to their target sequence.

However, nucleic acid analog competitors, like for example PNAs do not have to have a blocked 3'-OH group or a non-complementary base at their 3'-end as they are not recognized by the DNA polymerases because of the backbone modified by the peptide bond and thus are not extended. Other corresponding modifications of the phosphate group, which are not recognized by the DNA polymerases, are known to the person skilled in the art. Among those are inter alia nucleic acids having backbone modifications, like for example 2'-5' amide bonds (Chan et al. (1999) J. Chem. Soc., Perkin Trans. 1, 315-320), sulfide bonds (Kawai et al. (1993) Nucleic Acids Res., 1 (6), 1473-1479), LNA (Sorensen et al. (2002) J. Am. Chem. Soc., 124 (10), 2164-2176) and TNA (Schoning et al. (2000) Science, 290 (5495), 1347-1351).

Several competitors hybridizing to different regions of the template (for example, inter alia, the primer binding site) can also simultaneously be used in a PCR. The efficiency of the hybridization can additionally be increased, if the competitors have properties of secondary structure breakers.

In an alternative embodiment, the DNA competitor molecule can also have a sequence complementary to one of the primers. Depending on the ratio of antisense DNA competitor molecule and primer, such, for example, antisense DNA competitor molecules can then be used to titrate the primer in the PCR reaction, so that it will no longer hybridize with the corresponding template strand and, correspondingly, only the template strand defined by the other primer is amplified. The person skilled in the art is aware of the fact that, in this embodiment of the invention, the nucleic acid competitor can, but does not have to, be enzymatically extendable.

If, within the present invention, it is referred to nucleic acid competitors, this includes nucleic acid analog competitors, unless a different meaning arises from the respective context. The nucleic acid competitor can bind to the corresponding strand of the template reversibly or irreversibly. The bond can take place via covalent or non-covalent interactions.

Preferably, binding of the nucleic acid competitor takes place via non-covalent interactions and is reversible. In particular preferably, binding to the template takes place via formation of Watson-Crick base pairings.

The sequences of the nucleic acid competitors normally adapt to the sequence of the template strand to be detected. In the case of antisense primers, though, they adapt to the primer sequences to be titrated, which are in turn defined by the template sequences, however.

PCR amplification of nucleic acids is a standard laboratory method, the various possibilities of variation and development of which are familiar to the person skilled in the art. In principle, a PCR is characterized in that the double-stranded nucleic acid template, usually a double-stranded DNA molecule, is first subjected to heat denaturation for 5 minutes at 95° C., whereby the two strands are separated from each other. After cooling down to the so-called "annealing" temperature (defined by the primer with the lower melting temperature), the forward and reverse primers present in the reaction solution accumulate at those sites in the respective template strands, which are complementary to their own sequence. Herein, the "annealing" temperature of the primers adapts to the length and base composition of the primers. It can be calculated on the basis of theoretical considerations. Information on the calculation of "annealing" temperatures can be found, for example, in Sambrook et al. (vide supra).

Annealing of the primers, which is typically performed in a range of temperatures between 40 to 75° C., preferably between 45 to 72° C. and in particular preferably between 50 to 72° C., is followed by an elongation step, wherein deoxyribonucleotides are linked with the 3'-end of the primers by the activity of the DNA polymerase present in the reaction solution. Herein, the identity of the inserted dNTPs depends on the sequence of the template strand hybridized with the primer. As normally thermostable DNA polymerases are used, the elongation step usually runs at between 68 to 72° C.

In a symmetrical PCR, an exponential amplification of the nucleic acid region of the target defined by the primer sequences is achieved by means of repeating the described cycle of denaturation, annealing and elongation of the primers. With respect to the buffer conditions of the PCR, the usable DNA polymerases, the production of double-stranded DNA templates, the design of primers, the selection of the annealing temperature, and variations of the classic PCR, the person skilled in the art has numerous references at his disposal.

The person skilled in the art is familiar with the fact that, for example, single-stranded RNA, such as mRNA, can be used as template as well. Usually, this mRNA is previously transcribed into a double-stranded cDNA via a reverse transcription.

In one embodiment, a thermostable DNA-dependent polymerase is used as polymerase. In a particularly preferred embodiment, a thermostable DNA-dependent DNA polymerase is used, which is selected from the group consisting of Taq-DNA polymerase (Eppendorf, Hamburg, Germany and Qiagen, Hilden, Germany), Pfu-DNA polymerase (Stratagene, La Jolla, USA), Tth-DNA polymerase (Biozym Epicenter Technol., Madison, USA), Vent-DNA polymerase, DeepVent-DNA polymerase (New England Biolabs, Beverly, USA), Expand-DNA polymerase (Roche, Mannheim, Germany).

The use of polymerases, which have been optimized from naturally occurring polymerases by means of specific or evolutive alteration, is also preferred. When performing the PCR in the presence of the substance library support, the use of the Taq-polymerase by Eppendorf (Germany) and of the Advantage cDNA Polymerase Mix by Clontech (Palo Alto, Calif., USA) is particularly preferred.

Any preceding methods may also be performed using an inventive device having a displacement structure, as described above.

Another aspect of the present invention relates to the use of an inventive device for performing microarray-based tests.

In the following, special embodiments of the inventive devices and the inventive method are described.

Figure 5C:
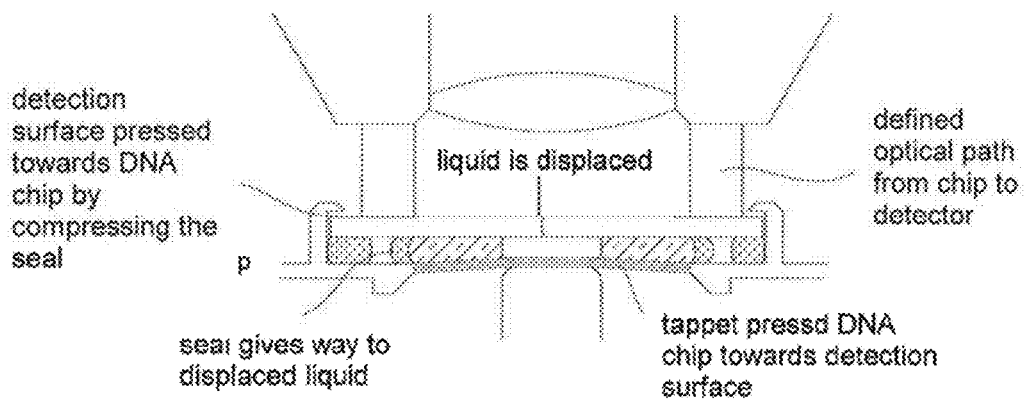
FIGS. 5A-5C are cross-sectional illustrations of the process and detection units of a device according to the invention at different stages of the corresponding inventive method.
Figure 5B:
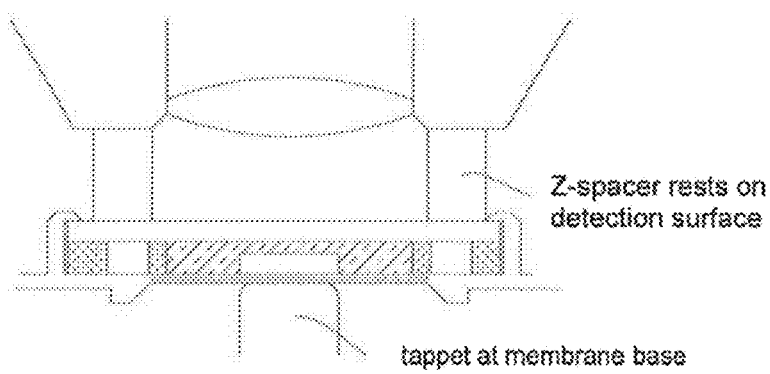
Figure 5A:
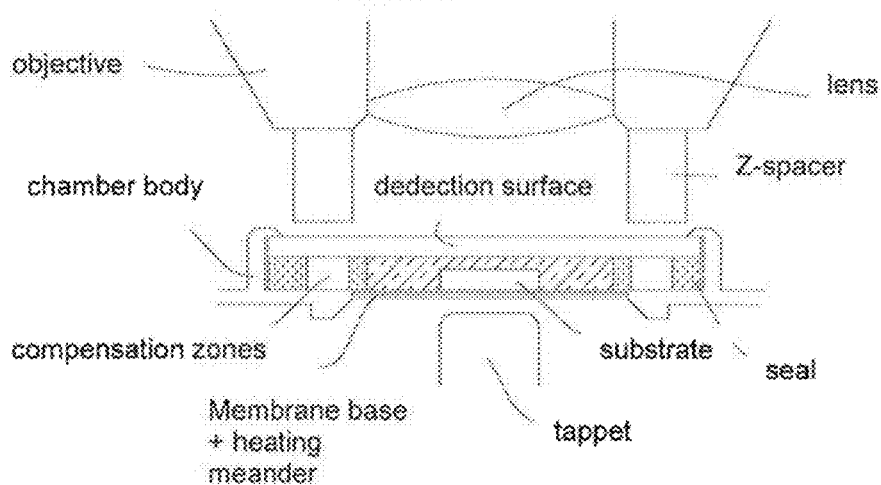

In FIGS. 5A-C, it is shown that the first surface, here an elastic membrane, in which preferably a heating device is integrated, is deformed by means of a pin or a tappet and that the chip is thus pressed towards the detection surface. Furthermore, the detection surface is pressed into the reaction chamber via a spacer on the second surface and thus approaches the DNA chip from above until the liquid between DNA chip and detection plane is almost entirely displaced. The elastic seals sealing the reaction chamber are compressed by guiding the detection surface towards the chip. The displaced fluid deforms the seal in such a way that the air is compressed in air compensation chambers. This occurs in a more efficient manner, if the second surface has the displacement structure described above.

However, the process unit can also be configured such that either only the first surface, for example in form of an elastic membrane, is deformed or only the detection plane is pressed into the chamber, potentially by using a displacement structure.

Figure 6B:
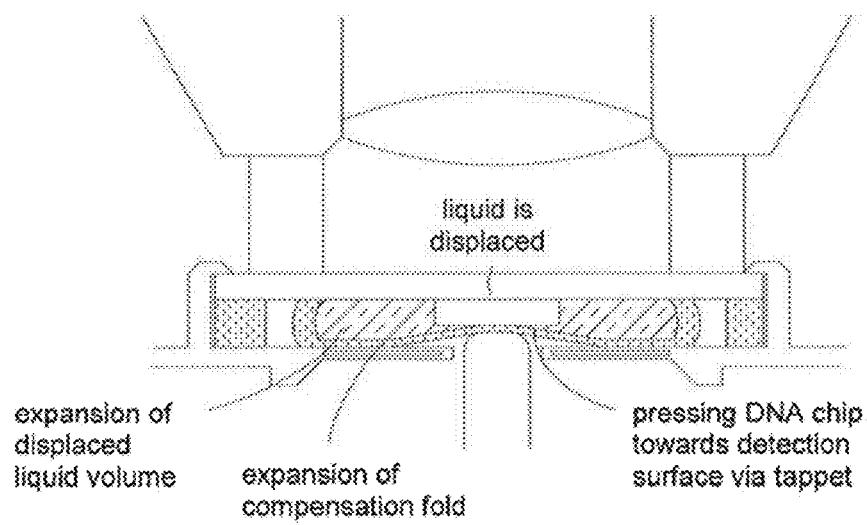
FIGS. 6A-6B are illustrations of the mode of function of the process unit according to the present invention.
Figure 6A:
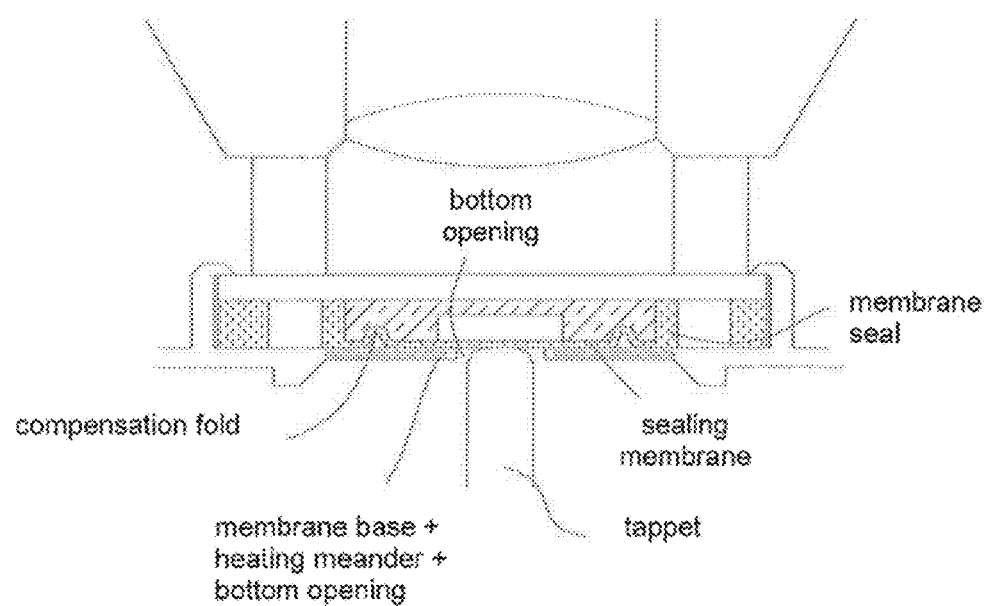

In FIGS. 6A and 6B, a further technical embodiment for compressing the process unit is depicted. The reaction chamber is sealed laterally and at the side opposite the detection surface by a sealing membrane, on which a DNA chip is attached. At the level of the DNA chip, the sealing membrane seals a hole in the lower side of the chamber body. The hole is slightly smaller than the DNA chip. When conducting a PCR in the reaction chamber, the hole is tightly sealed by the internal pressure forming due to the raised temperatures connected with the PCR. Therefore, despite the labile sealing membrane, the chamber is pressure-proof (principle of the self closing valve). For detection, a pin or a tappet is pushed through the lower side hole. The sealing membrane is lifted and the DNA chip is pressed against the detection plane. In order to ensure the required elasticity of the sealing membrane, the membrane can be provided with a compensation fold. In this embodiment, the pressure compensation chambers are also compressed by the displaced liquid. This embodiment may also have a displacement structure.

The following examples are for the purpose of illustrating the invention, and are not to be construed as limiting the scope of the invention.

EXAMPLES

Example 1

Setup of a Reaction Cartridge without an Integrated Heating

Figure 8:
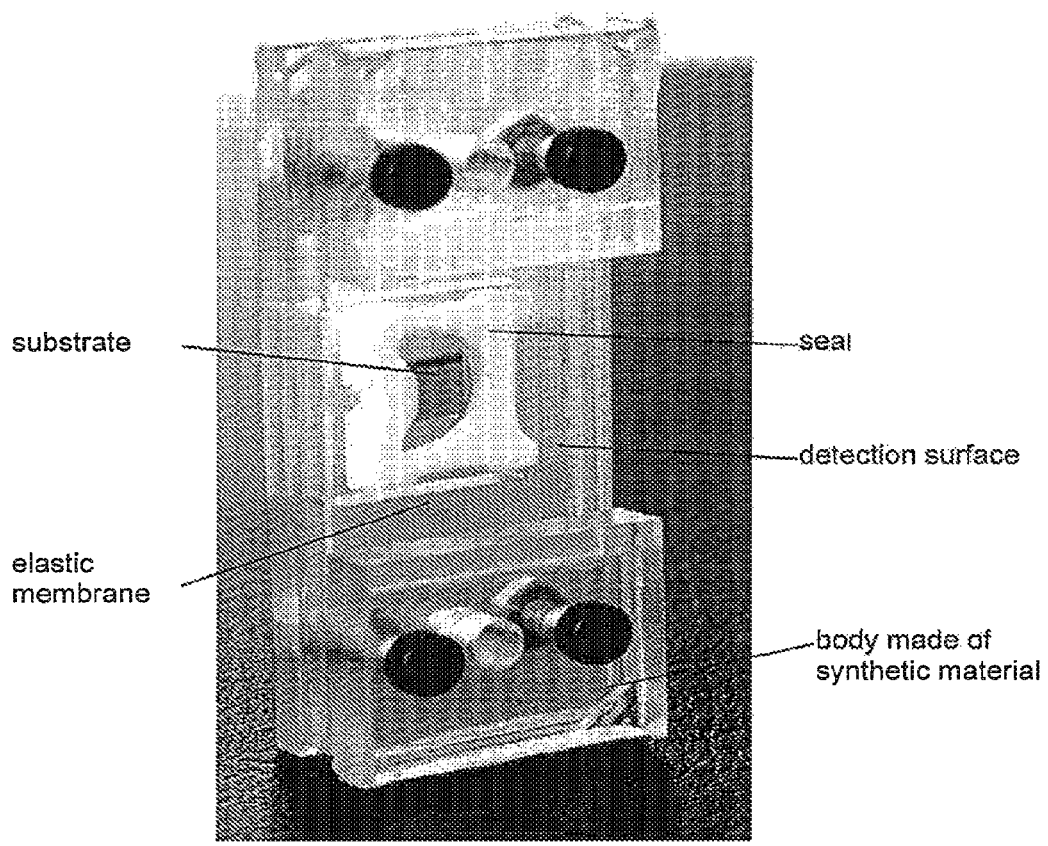
FIG. 8 illustrates a milled and bolted process unit of an inventive device.
Figure 9:
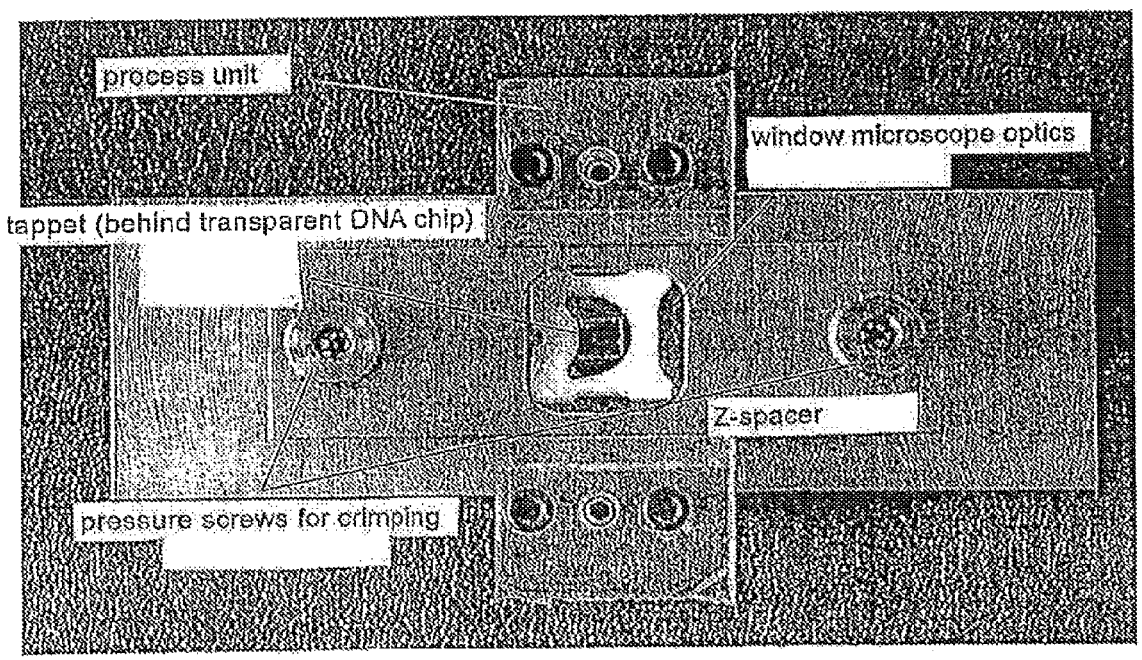
FIG. 9 illustrates a compressing or crimping device for the process unit according to the invention.

In FIGS. 8 and 9, an embodiment of a processing unit without an integrated heating and a device for guiding the DNA-chip towards the detection plane are depicted. The DNA-chip in the device can be read out using a conventional fluorescence microscope (for example Axioskop, Zeiss, Jena, Germany).

Example 2

Setup of a Reaction Cartridge having a Silicon Heating Substrate

The variant of the processing unit of the inventive device, which is shown in FIGS. 10 and 11, is a miniaturized reaction cartridge having an integrated probe array (DNA-chip), a silicon heating substrate having an integrated temperature sensor ("heating substrate") for adjusting distinctive temperatures in the reaction chamber as well as a circuit board optionally having an EPROM for electrically contacting the heating substrate. The individual components are embedded in two shells made of synthetic material. The entire unit is a spatially closed system, in which all reactions (for example PCR) can be performed in a temperature-controlled manner.

First, the circuit board is inserted into the shaft provided in the lower shell (with the EPROM facing downwards). On the upper side of the circuit board, three electric contact surfaces ("contact pads") are arranged, which ensure the electric connection with the subsequently inserted heating substrate, which in turn bears the contact pads. Said heating substrate has a size of 8 mm×6 mm and a thickness of about 0.6 mm. The heating substrate ensures exact adjustment of different temperatures (for example of 40° C. to 95° C.) during the analysis performed. Measuring the temperature in the reaction chamber can be conducted either via the sensor integrated in the heating substrate or via an external measuring unit, which measures the temperature directly on the surface of the heating substrate. In the latter case, the integrated sensor in the heating substrate can be omitted. The integrated components used for heating and/or temperature measurement can, for example, be diodes or also transistors. The surface of the silicon heating substrate, which is facing towards the reaction space, does not contain any electrical systems and is coated with an $SiO_2$ passivating layer.

The next component inserted is an elastic seal, which laterally limits the reaction space.

In the center of the reaction space, the DNA chip is attached in such a way that the probe array is facing towards the detection plane. After inserting the detection surface in the form of a glass surface, said surface still protrudes from the lower shell by 0.2 mm. By subsequently adding the upper shell, which is guided by means of locating pins, the glass surface is pressed against the seal and thus ensures optimal sealing of the reaction chamber.

Subsequently, the reaction chamber can be filled with reaction solution. There, it is to be noted that only the inner space containing the chip is filled, but not the outer chambers. The liquids required are injected into the reaction space using cannulas via the cannula guide provided.

Then, it is possible to perform biochemical reactions that are controlled via the silicon heating substrate, such as PCR and/or hybridization, in the reaction chamber.

For the determination of the intermediate or the final result, the detection plane is pressed against the DNA-chip from above via the spacers of the detection unit, until the distance between detection plane and substrate is about zero. Thereby, the surrounding liquid is displaced into the outer chambers, where it compresses the local air. This process is reversible and can, for example, be performed after each PCR cycle.

Due to its compact design as well as the internal circuit board having an EPROM and the integrated heating substrate, this variant of the inventive device is particularly suitable for mobile use.

Example 3

Detection of the Decrease of Background Signal by Displacing the Analyte

All fluorescence measurements described in this example were performed using a fluorescence microscope (Zeiss, Jena, Germany). Excitation occurred in incident light using a white light source and a filter set suitable for Cyanine 3. The signals were recorded by means of a CCD camera (PCO-Sensicam, Kehlheim, Germany). In the following, the thickness of the gap denotes the distance between microarray and detection plane.

a) Measuring the Fluorescence Signal of the Analyte Depending on the Thickness of the Gap Channel shells having defined channel depth (5 μm, 10 μm, 28 μm) made of Sylgard were cast. The channels had a width of 125 μm. A glass chip was placed across the unequally deep channels. The channels were then filled with a 200 nM solution of a Cy3-labeled oligonucleotide in 2×SSC+0.2% SDS and the signal was measured with an exposure time of 1.5 s.

Figure 12:
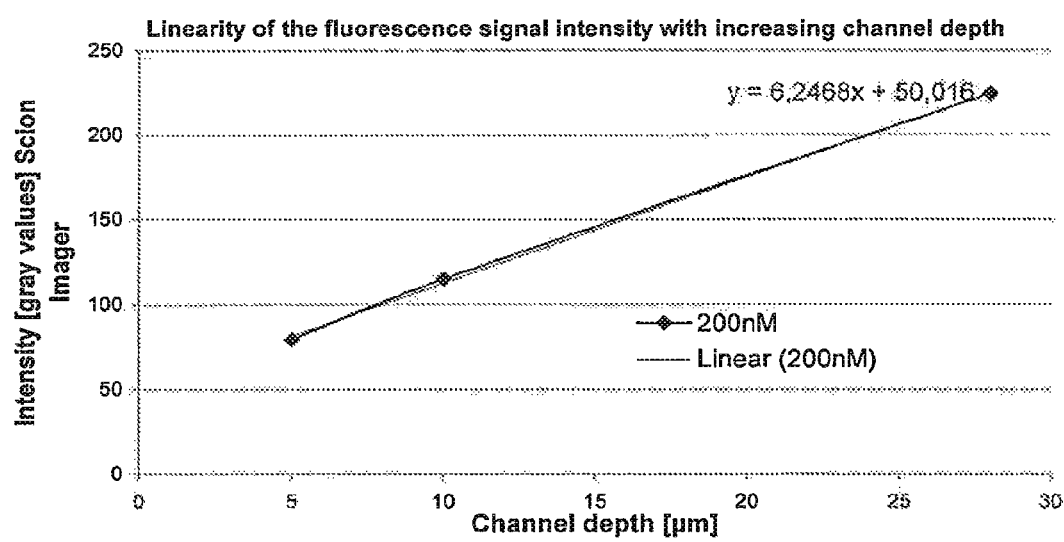
FIG. 12 illustrates the linear correlation of fluorescence signal intensity and the thickness of the capillary gap between the two surfaces of an inventive reaction chamber.

In FIG. 12, the results are depicted. The signal increases linearly as the channel depth increases. A straight regression line could be calculated (equation 1)

$$F(x)=6.2468x+50.016 \tag{Equation 1}$$

Using the regression equation obtained (equation 1), the layer thicknesses between DNA chip and detection surface can now be determined by means of the background fluorescence signal.

Figure 15:
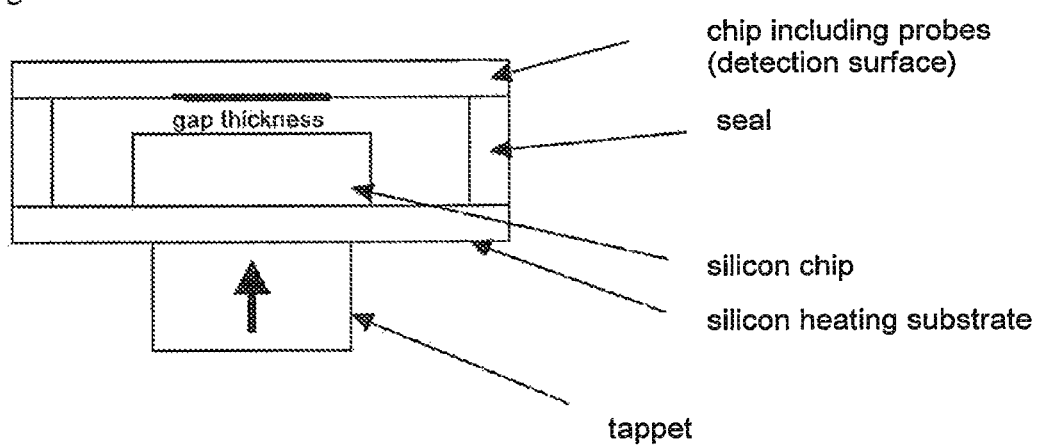
FIG. 15 is a schematic illustration of the experimental setup for analysis of DNA arrays according to the invention without performing any rinsing steps.

This was analyzed by stacking two glass surfaces (chips) having structured marks on their upper sides (crosses, numbers, and data matrix in FIG. 14), to which could be focused. The chips were stacked in such a way that the structured marks were oriented towards each other and were only separated by a thin liquid layer. A 200 nM solution of a Cy3-labeled oligonucleotide in 2×SSC+0.2% SDS was used as liquid. Using the focusing device of the microscope, which was provided with a scale, the distance between the marks and therefore the layer thickness of the liquid film could directly be determined. The intensity of the background is 158 gray values with an exposure time of 0.75 s. The thickness of the gap as measured using the fluorescence microscope, is 40 μm. Assuming that the measured gray values behave linearly in relation to exposure time (see FIG. 13), according to equation 1 the resulting thickness of the gap is 42.6 μm. The values for the thickness of the liquid layer thus obtained are well in agreement with each other.

b) Experiments for Reducing or Preventing Background Fluorescence by Means of Compressing the Process Unit In these experiments, the hybridization signal was measured depending on the displacement of the fluorescent analyte caused by applying pressure via a tappet. The experimental setup is shown in FIG. 15. By applying pressure via the tappet, the silicon chip (3.15×3.15 mm) was pressed towards a probe chip (DNA chip), and in this process the liquid located between the two surfaces was displaced.

For performing the experiment, the chamber was filled with a hybridization solution, representing a model system for the conditions in a PCR hybridization. The hybridization solution included a Cy3-labeled oligonucleotide (final concentration 2 nM in 2×SSC+0.2% SDS), which displayed complementarity to the probe array. In addition, the hybridization solution included another Cy3-labeled oligonucleotide, which does not hybridize with the probe array and therefore only contributes to the fluorescence background signal in the solution, but not the specific signals at the spots.

Hybridization was performed for 10 min. For the subsequent reading out the hybridization signals, a fixed exposure time of 1.5 s was selected. At the experimental setup, the tappet was pushed nearer towards the probe array (detection surface) after each recording, so that the gap between array and second surface, which is filled with hybridization solution, was reduced.

Figure 16:
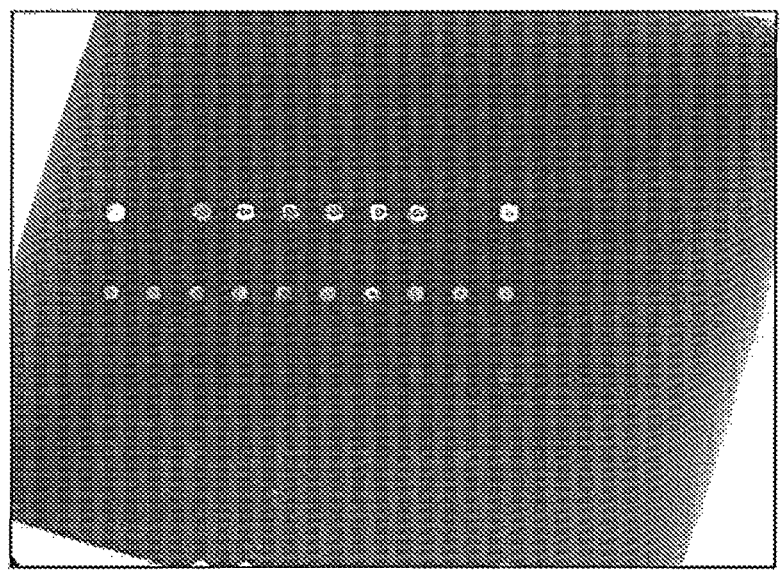
FIG. 16 illustrates a fluorescence measurement of an array with chip pressed towards it.
Figure 17:
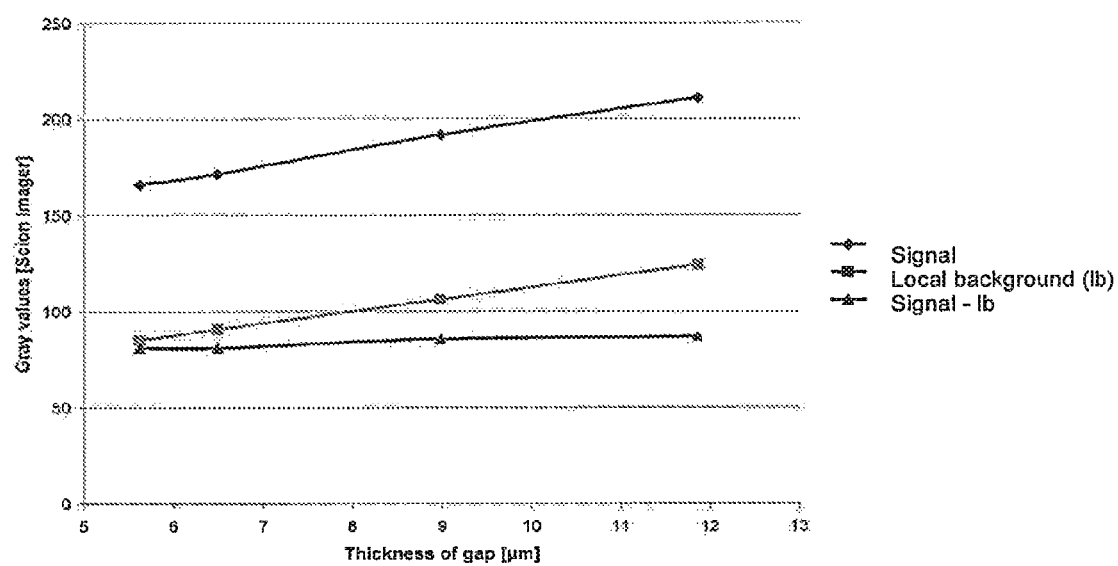
FIG. 17 illustrates the correlation of signal intensities and reduced thickness of the capillary gap.

FIG. 16 shows a recording of the hybridization signal with a thickness of the gap of 10 μm. The results for background signal and hybridization signal at the spots are depicted in FIG. 17. As expected, both signals behave linearly in relation to the thickness of the gap. Thus, the spot signal that is corrected by the background does not change with the thickness of the gap.

When a gray value of 255 is reached, the instrument is overloaded. That is., with a thickness of the gap of about 17 μm, measuring the spot intensity is only possible by reducing exposure time. For that reason, measuring sensitivity is then reduced.

Thus, the dynamic measuring range is increased by reducing the thickness of the gap. By means of background adjustment of the spot signals (difference formation), the thickness of the gap can be varied in a broad range without influencing the measurement and the results. With very large thicknesses of the gap (>20 μm), measurement is strongly impaired due to overload of the detector.

c) Amplification, Hybridization and Detection as One-stage Reaction

Two process units having a structure according to FIG. 15 were mounted and numbered.

Two identical reaction setups having the following composition were prepared:

Reaction Setup:

| | |
|---|---|
| 20 mM dNTPs | 0.5 μl |
| 1M potassium acetate (Kaac) | 3 μl |
| 25 mM Mg-acetate Eppendorf | 5 μl |
| C1Ontech C-DNA PCR buffer | 5 μl |
| Eppendorf Taq-polymerase | 3 μl |
| 10 μM primer CMV_DP_Cy3<br>Cy3_5'TGAGGCTGGGAARCTGACA3' (SEQ ID NO: 1) | 1 μl |
| 10 μM Primer CMV_UP_NH2<br>5'GGGYGAGGAYAACGAAATC3'_NH2 (SEQ ID NO: 2) | 0.66 μl |
| 10 μM primer CMV_UP<br>5'GGGYGAGGAYAACGAAATC3' (SEQ ID NO: 3) | 0.33 μl |
| 10 μM primer Entero_DP_Cy3<br>Cy3 5'CCCTGAATGCGGCTAAT3' (SEQ ID NO: 4) | 1 μl |
| 10 μM primer Entero_UP_NH2<br>5' ATTGTCACCATAAGCAGCC3' NH2 (SEQ ID NO: 5) | 0.66 μl |
| 10 μM primer Entero_UP<br>5'ATTGTCACCATAAGCAGCC3' (SEQ ID NO: 6) | 0.33 μl |
| 10 μM primer HSV1_DP_Cy3<br>Cy3_5'CTCGTAAAATGGCCCCTCC3' (SEQ ID NO: 7) | 1 μl |
| 10 μM primer HSV1_UP_NH2<br>5'CGGCCGTGTGACACTATCG3' NH2 (SEQ ID NO: 8) | 0.66 μl |
| 10 μM primer HSV1_UP<br>5'CGGCCGTGTGACACTATCG (SEQ ID NO: 9) | 0.33 μl |
| 10 μM primer HSV2_UP_Cy3<br>Cy3_5'CGCTCTCGTAAATGCTTCCCT3' (SEQ ID NO: 10) | 1 μl |
| 10 μM primer HSV2_DP_NH2<br>5'TCTACCCACAACAGACCCACG3' NH2 (SEQ ID NO: 11) | 0.66 μl1 |
| 10 μM primer HSV2_DP<br>5'TCTACCCACAACAGACCCACG3' (SEQ ID NO: 12) | 0.33 μl1 |
| 10 μM primer VZV_DP_Cy3<br>Cy3 5'TCGCGTGCTGCGGC (SEQ ID NO: 13) | 1 μl |
| 10 μM primer VZV_UP_NH2<br>5'CGGCATGGCCCGTCTAT3 NH2 (SEQ ID NO: 14) | 0.66 μl |
| 10 μM primer YZY_UP<br>5'CGGCATGGCCCGTCTAT (SEQ ID NO: 15) | 0.33 μl |
| Template CMV | 1 μl |
| PCR grade water | 22.5 μl |
| Total | 50 μl |

The process units were filled with 50 μl reaction setup each and processed according to the following temperature-time scheme.

| 1 | Denaturation | 95° C. |
|---|---|---|
|   | Duration | 300 s |
| 2 | Denaturation | 95° C. |
|   | Duration | 10 s |
| 3 | Annealing/Extension | 60° C. |
|   | Duration | 20 s |
| Repeating steps 2 to 3 | | 35 times |
| 4 | Denaturation | 95° C. |
|   | Duration | 300 s |
| 5 | Hybridization | 40° C. |
|   | Duration 3600 s | |

Then, the two process units were subjected to different treatments. In the first case (process unit 1), the background fluorescence was reduced by displacing the analyte. This was accomplished by pushing the tappet upwards in the direction of the detection surface, so that the gap filled with reaction solution is reduced as far as possible.

In the second case (process unit 2), the analyte was replaced by a non-fluorescent solution. The replacement of the solution was performed with 2×SSC buffer at a fluctuation rate of 300 µl min and a rinsing volume of 900 µl. This procedure corresponds to the state of the art.

Subsequently, both strategies for reducing background fluorescence were compared. To this end, the hybridization signals in both process units were detected with the aid of the fluorescence microscope camera setup described.

Figure 18:
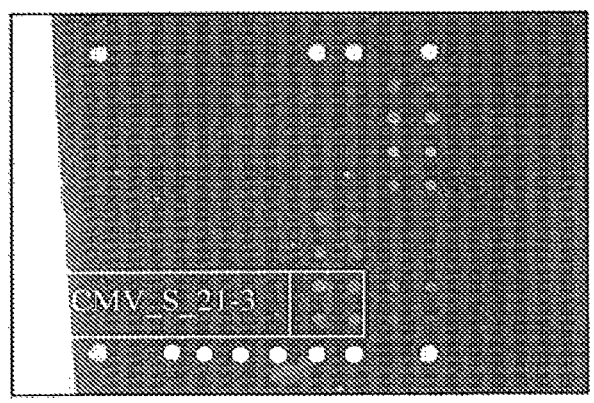
FIG. 18 illustrates the detection of the probe signals by displacing background fluorescence.
Figure 19:
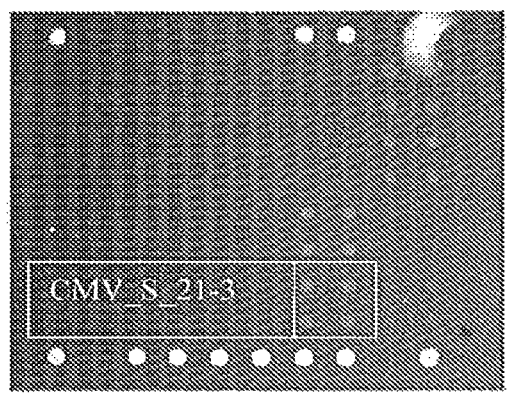
FIG. 19 illustrates the detection of the probe signals of a DNA array.

Exposure time was 5 s (see FIG. 18 and FIG. 19). Comparing the spot intensities was performed on the basis of the spot comprising substance CMV_S_21-3 (5'-NH$_2$TGTTGGGCAACCACCGCACTG-3' (SEQ ID NO: 16)). The location of the probes is indicated in FIGS. 18 and 19.

Figure 20:
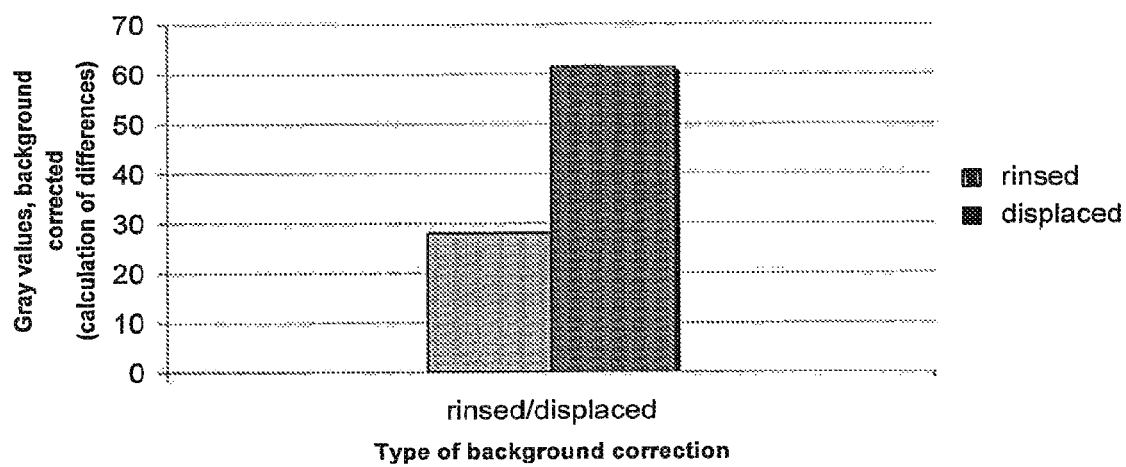
FIG. 20 depicts assay results obtained when performing the inventive detection method with two different strategies for reducing the signal background.

In FIG. 20, the result of the experiment is shown. By rinsing the reaction chamber in process unit 2, the hybridization signal is reduced compared to the displacement in process unit 1. It is assumed that "bleeding" of the probes is responsible for this.

Thus, the method of analyte displacement according to the inventive method is to be preferred compared to replacement of the solutions.

Figure 21:
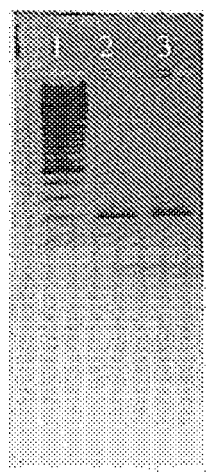
FIG. 21 depicts an analysis of the PCR products obtained in the assay according to FIG. 20 by using agarose gel electrophoresis.

In order to obtain evidence on amount and integrity of the amplification product, 5 µl of each reaction solution were additionally analyzed on a 2% agarose gel. The result (ethidium bromide-stained gel detected with an UV transilluminator) is shown in FIG. 21.

Example 4

Device for the Processing and Detection of Inventive Reaction Cartridges

Figure 28:
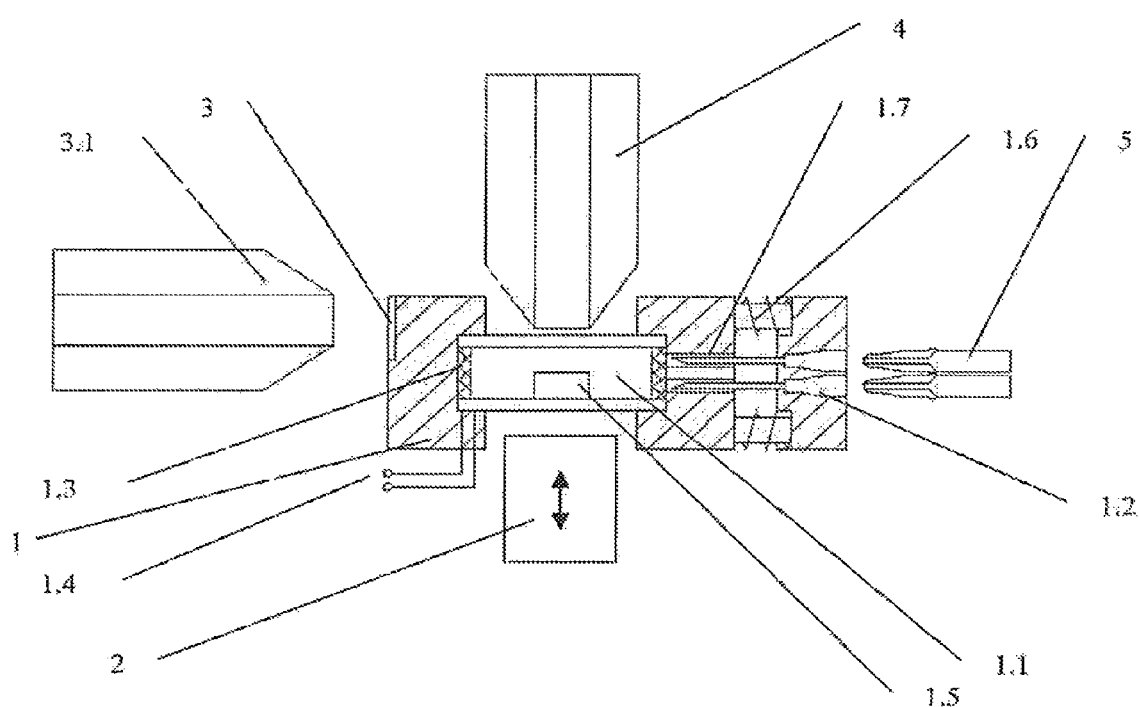
FIG. 28 is a schematic view of a device according to the invention comprising modular processing and detecting units.

A device for the processing and detection of inventive reaction cartridges in accordance with this Example is shown in FIG. 28.

The device for performing microarray-based tests with reaction cartridges according to the present invention usually consists of several components, which may be combined in one device or assembled modularly from several partial devices. Optionally, the device may be activated via an integrated computer or via an interface to an external computer. The setup of the device is illustrated in FIG. 28.

An exemplary procedure is as follows:

The fluid interface of the reaction cartridge is manually brought in the filling position by the operator, in which the cannulas penetrate the seal of the chamber body. Subsequently, the operator introduces the reaction mixture into the reaction chamber by means of a standard laboratory pipette. Both steps can also be achieved by a correspondingly configured device. The fluid interface is then again brought in the home position, wherein said procedure can also be achieved by a correspondingly configured device.

The reaction cartridge is then inserted into the device. A data matrix reader, which is arranged in the device, recognizes the unique data matrix attached to the reaction cartridge and, via a user-transmitted data set, transfers the characteristic data for the cartridge as well as for the test to be conducted to the control computer. This computer then controls the individual process steps, which can, for example, comprise an amplification and hybridization. Via the integrated pressure means, the capillary gap in the reaction chamber is subsequently reduced according to the present invention to allow for detection.

Detection can be performed with conventional fluorescence-optical imaging or non-imaging systems. The data thus obtained are transmitted to a control computer for evaluation as well as presentation or storage on an internal or external interface.

Then, the reaction cartridge can be removed from the device and discarded by the operator.

Example 5

Reaction Cartridge Made of Electrically Conductive Synthetic Material

Figure 29:
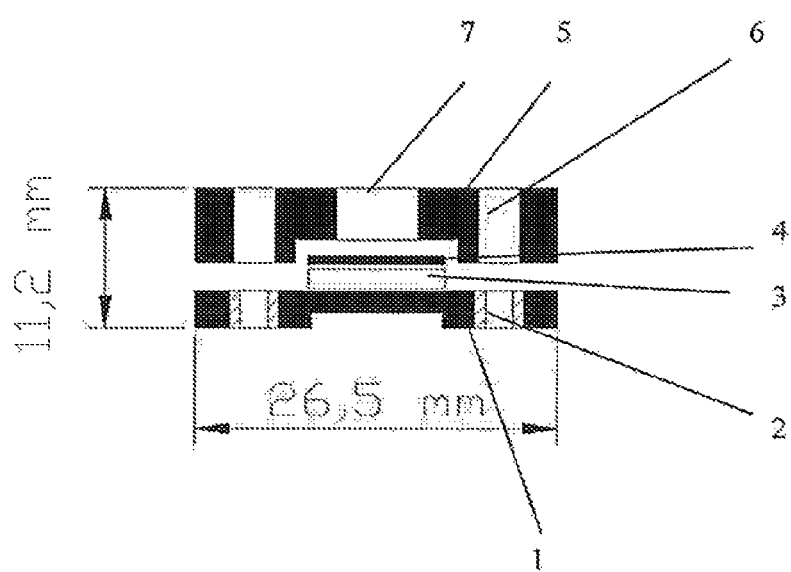
FIG. 29 illustrates a reaction cartridge as described in example 5.

A reaction cartridge as depicted in FIG. 29 is prepared.

The lower shell (1) of the reaction cartridge consists of electrically conductive synthetic material forming the base of the reaction chamber (Conduct 2, RKT, Germany). A foil PT-100 temperature sensor is fixed to the bottom side of the chamber base using a suitable adhesive, for example Loctite 401 (Loctite, Germany). Together with the seal (3) and the coverslip (4), the lower shell forms the reaction chamber of the cartridge according to the present invention.

The cartridge further has a threaded drill hole (2) for inserting screws for electrical contacting, an upper shell (5) of the reaction cartridge, for example one made of acryl, a drill hole (6) for attaching the upper shell, and a detection window (7) within the upper shell.

A standard PCR reaction mixture is prepared:

| | |
|---|---|
| 30.5 µl | de-ionized water |
| 5 µl | 10 × PCR buffer (e.g., 10 × cDNA PCR reaction buffer, Clontech, Germany) |
| 5 µl | Mg-acetate, 25 mM (e.g., Eppendorf, Germany) |
| 0.5 µl | dNTP, 20 mM each |
| 1 µl | 16sfDl (5'-AGAGTTTGATCCTGGCTCAG-3' (SEQ ID NO: 17)), 10 mM |
| 1 µl | 16sRa (5'-TACCGTCACCAT AAGGCTTCGTCCCTA-3' (SEQ ID: 18)), 10 mM |
| 3 µl | Taq DNA polymerase (e.g., Genaxxon, Germany) |
| 1 µl | template |

By using an insulin syringe (Becton Dickinson, Germany), the reaction chamber is filled with the reaction mixture. For ventilation during the filling procedure, a second cannula is penetrated through the seal of the chamber body. After filling, ventilation cannula and insulin syringe are properly discarded.

The chamber is then connected to a regulating unit (CLONDIAG chip technologies GmbH, Germany) via the two screws provided for this purpose. Likewise, the temperature sensor is connected to said regulating unit at the bottom side of the lower shell. Said regulating unit is capable of regulating specific temperatures in the lower shell according to a predefined program.

In this manner, the following PCR program is conducted: 5 min 95° C., 30×(30 s 95° C., 30 s 62° C., 50 s 72° C.).

Figure 30:
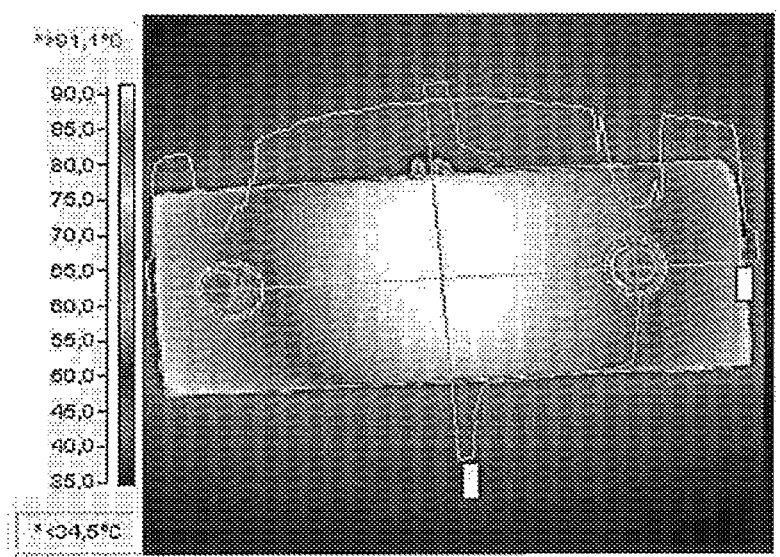
FIG. 30 is an illustration of the reaction cartridge according to example 5 using a thermal imaging camera at a temperature of 95° C.

FIG. 30 shows an image of the reaction cartridge recorded using a thermal imaging camera at a temperature of 95° C.

After completion of the program, the reaction product is removed from the reaction chamber by means of an insulin syringe. Analogously, a cannula is penetrated through the seal of the chamber body for ventilation during the emptying of the reaction chamber.

Figure 31:
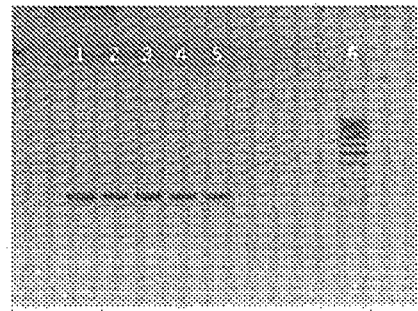
FIG. 31 depicts an analysis of the reaction product according to example 5 by using agarose gel electrophoresis.

The reaction product is analyzed by agarose gel electrophoresis. To this end, 5 µl of the reaction solution, along with a suitable buffer (for example 5 µl 250 mM in 50% glycerin, bromphenol blue), are applied to the pocket of a 2% agarose gel and an electrophoresis is performed. The result is depicted in FIG. 31.

As can clearly be seen, an amplification product of correct size and in an amount comparable to the positive control could be obtained in all cases.

Example 6

Reaction Cartridge having a Displacement Structure on the Second Surface

A reaction cartridge as shown in FIGS. 5A-C or 6A-B is prepared. In the center of the second surface of the inventive device a drop (about 20 μl) of Sylgard 184 is deposited using a pin. Subsequently, the second surface with the silicone drop is incubated, for example, in an oven at 120° C. for one hour in order to cross-link the Sylgard. Subsequently said second surface is assembled in a device according to the present invention. A DNA probe array is applied onto the first surface.

A PCR setup is prepared according to the following scheme:

| | | |
|---|---|---|
| 10 × Clontech cDNA buffer | | 20 μl |
| 25 mM Mg acetate Eppendorf | | 20 μl |
| dNTP's 20 mM each | | 2 μl |
| Genaxxon Taq polymerase | | 12 μl |
| Bidest | | 122 μl |
| Primer 1 | 10 μM with Cy3 label | 4 μl |
| Primer 2 | 10 μM | 4 μl |
| 1M K acetate | | 12 μl |
| Template DNA | | 4 μl |

20 μl of this mixture are introduced in the inventive device. Subsequently, the device is connected to a corresponding controller (prototype, Join, Jena, Germany), and a PCR is preformed according to the following scheme.

| | | | |
|---|---|---|---|
| 1) | Denaturation | 95° C. | 500 s |
| 2) | Denaturation | 95° C. | 10 s |
| 3) | Annealing | 60° C. | 30 s |
| 4) | Elongation | 72° C. | 30 s |
| 5) | 37 times repeating steps 2 to 4 | | |
| 6) | Denaturation | 95° C. | 60 s |
| 7) | Hybridization | 50° C. | 45 min |

Figure 33:
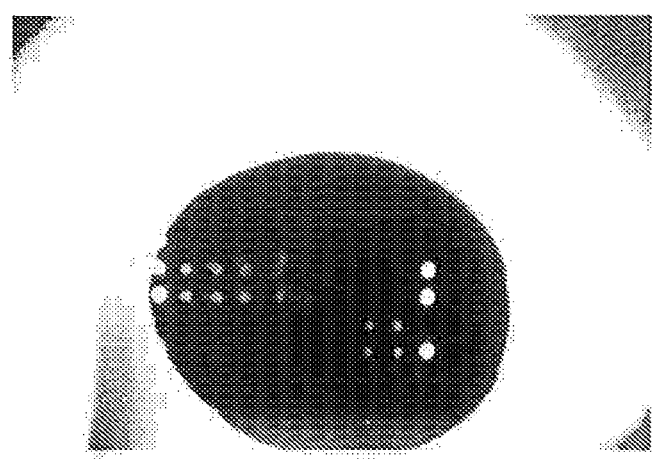
FIG. 33 depicts the hybridization results of a probe array obtained using a reaction chamber having a displacement structure as described in example 6.

Then, the first surface is guided towards the second surface until the displacement structure contacts the surface area of the first surface. By flattening the elastic displacement structure on the surface of the microarray, the fluorescent solution causing the background is displaced completely and the signal can be detected. (see FIG. 33)

FIGURES

FIG. 1: Schematic view of the device according to the present invention comprising a read out device and the process unit.

FIG. 2: View of the process unit according to the present invention.

FIG. 3: Exploded view of the process unit according to the present invention comprising detection surface, seal, DNA-chip, and chamber body. The chamber body has a reversibly deformable elastic membrane.

Figure 4:
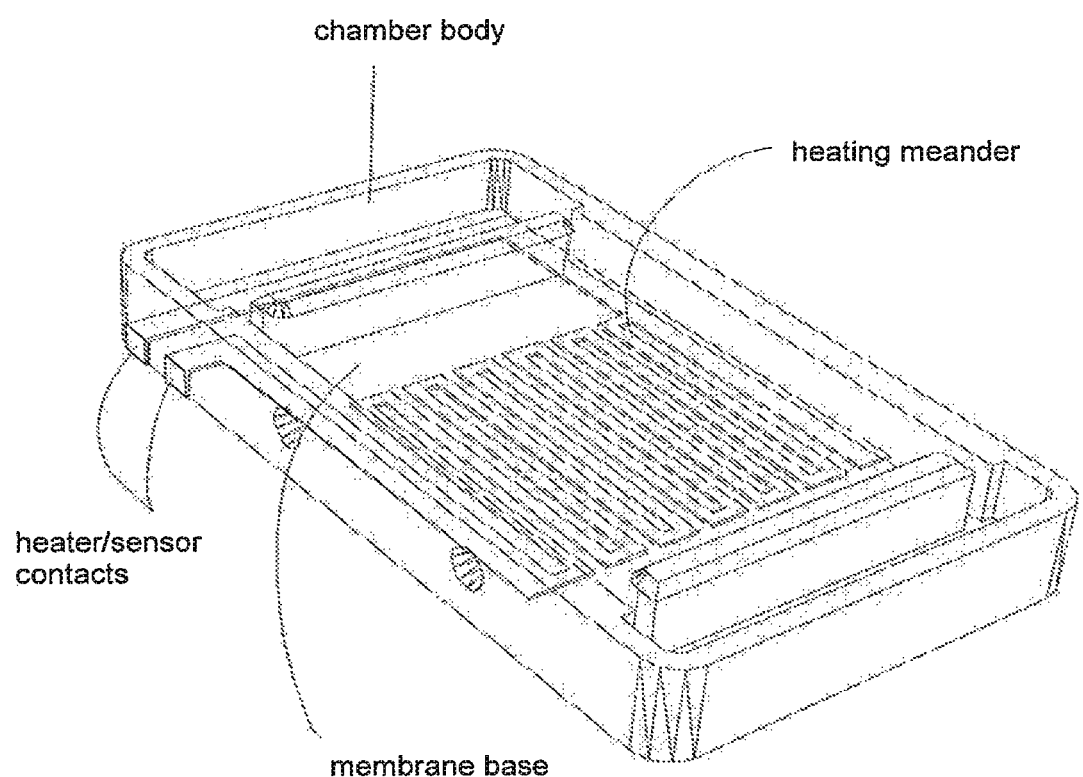
FIG. 4 is a perspective view of the chamber body of a device according to the invention.

FIG. 4: View of the chamber body having a heating meander embedded by injection-molded synthetic material in the elastic membrane.

FIGS. 5A-C: Illustration of the status of the process unit according to the present invention in the read out device A) during PCR, B) before detection, and C) during detection.

FIGS. 6A-B: Illustration of the mode of function of the process unit according to the present invention having membrane seal, compensation fold, and bottom hole. In A), the process unit is shown in home position. In B), the process unit is shown in compressed form, in which the fluorescent solution between DNA-chip and detection surface is displaced.

FIG. 7: View of a rotary disc, whereon four temperature blocks are installed. The temperature blocks are thermostaticized to one temperature each. By means of rotating the disc and/or the process unit, the temperature in the reaction chamber can be altered.

FIG. 8: View of an exemplary milled and bolted process unit.

FIG. 9: View of an exemplary compressing or crimping device for the process unit according to the present invention for the detection of the hybridization signals in a conventional fluorescence microscope.

FIG. 10: View of a process unit according to the present invention having a circuit board as electric connection for heater and temperature sensor. The heater is developed as a semiconductor component.

FIG. 11: Exploded view of the process unit shown in FIG. 10.

FIG. 12: View of the straight regression line for determining the width of a gap filled with fluorophore.

Figure 13:
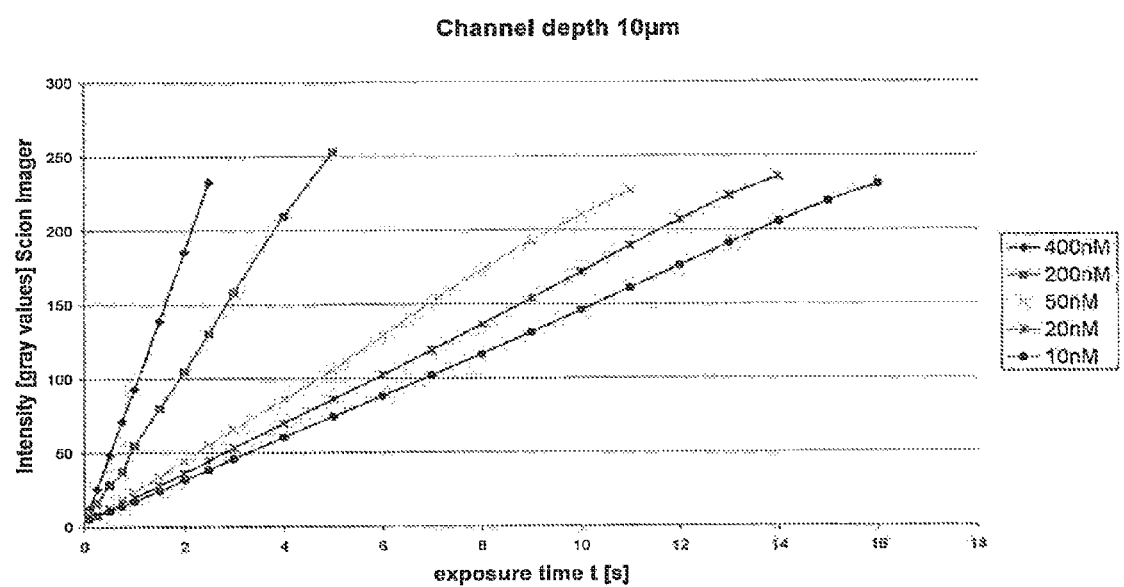
FIG. 13 illustrates the linear correlation of fluorescence signal intensity and the exposure time when performing detection of analytes according to the invention.

FIG. 13: View of the linearity of the fluorescence signal as the exposure time increases over the metering range.

Figure 14:
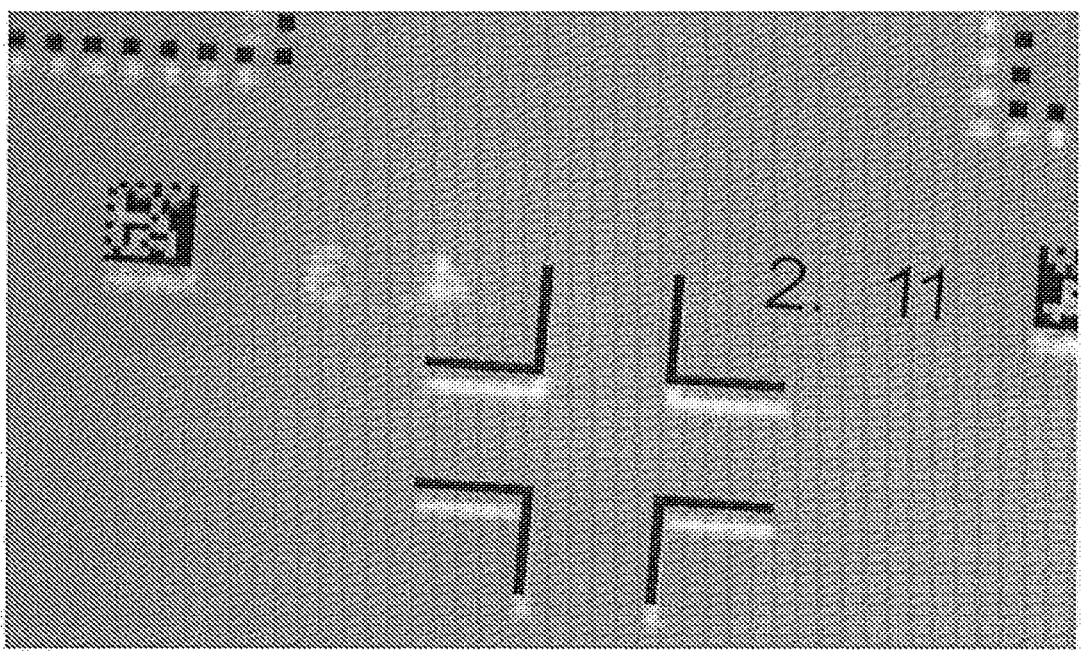
FIG. 14 illustrates the fluorescence recording of two superimposed chips, the gap between them comprising a Cy3 fluorophore.

FIG. 14: Fluorescence recording of two superimposed chips, the gap between which is filled with 200 nM Cy3 fluorophore. The intensity of the background is 158 gray values at an exposure time of 0.75 s. The thickness of the gap measured using a fluorescence microscope is 40.00 μm. Assuming that the measured gray values behave linearly in relation to the exposure time (see FIG. 13), the resulting thickness of the gap, as determined by using equation 1, is 42.6 μm. The values for the thickness of the layer thus obtained are in well agreement with each other.

FIG. 15: Illustration of the experimental setup for the detection of DNA arrays without rinsing.

FIG. 16: Fluorescence measurement of an array with chip pressed against it. The white margins are indicative for the background radiation caused by the displaced sample solution.

FIG. 17: Decrease of absolute intensities of signal and background with reduced thickness of the gap. The difference of both values is constant throughout the metered region.

FIG. 18: Detection of the probe signals by displacing background fluorescence. At the left margin, the non-displaced liquid is shown.

FIG. 19: Detection of the probe signals of a DNA array. The background was corrected by rinsing.

FIG. 20: Measurement results of an experimental comparison of displacement and replacement of the analyte.

FIG. 21: Reference analytics of the PCR in a process unit, measured by gel electrophoresis.

FIG. 22: Schematic view of a detachable filling unit for filling reaction cartridges with reactive substances or buffers. The following reference numbers are used:
- 1 Filling unit
- 1.1 Mechanical interface filling unit—cartridge
- 2 Cartridge
- 2.1 Mechanical interface cartridge—filling unit
- 2.2 Seal
- 2.3 Reaction chamber
- 2.4 Preferred opening for the cannulas in the cartridge
- 3 Filling channel
- 3.1 Fluidic and mechanical interface to sample-adding tools 3.2 Filling cannula
4 Waste channel with waste container
4.1 Ventilation hole
4.2 Waste cannula FIGS. 23A-B: View of the procedure for filling a reaction cartridge by means of a modular filling unit.

FIG. 24: Schematic view of an integrated filling unit for filling reaction cartridges with reactive substances or buffers in the preferred position without penetration of the seal of the chamber body. The following reference numbers are used:
1 Filling unit—cartridge
1.1 Mechanical interface cartridge—filling unit
2 Reaction cartridge
2.1 Mechanical interface cartridge—filling unit
2.2 Seal
2.3 Reaction space
2.4 Preferred opening for the cannulas in the cartridge casing
3 Filling channel
3.1 Fluidic and mechanical interface to sample-introducing tools
3.2 Filling cannula
4 Waste channel with waste container
4.1 Fluidic and mechanical interface to sample-removing units
4.2 Waste cannula
5 Equipment for preferred position, here: spring FIGS. 25A-B: Illustration of the procedure for filling a reaction cartridge having an integrated filling unit.

FIG. 26: Schematic view of an integrated filling unit having an integrated waste container for filling reaction cartridges with reactive substances or buffers in the preferred position without penetration of the seal of the chamber body. The following reference numbers are used in addition to the reference numbers in FIG. 24:
4 Waste channel with waste container
4.1 Ventilation hole FIGS. 27A-B: A) Filling of the reaction space when removing the surplus liquid into a waste container or channel, B) removal of surplus liquid when reducing the reaction space for detection. The following reference numbers are used:
1 Reaction chamber
2 Seal
3 Pressure means
4 Fluid interface
4.1 Removing cannula
4.2 Introducing cannula FIG. 28: Device for processing and detecting inventive reaction cartridges according to example 4. The following reference numbers are used:
1 Reaction cartridge
1.1 Reaction chamber with microarray
1.2 Fluid system interface
1.3 Seal of the chamber body
1.4 Electric connections for heating system, optionally also temperature sensors
1.5 Chip
1.6 Position-securing system for implementing a preferred position and guiding the cannulas
1.7 Cannulas
2 Pressure nleans
3 Identification system, for example bar code or data matrix
3.1 Identification optics, for example bar code- or data matrix reader
4 Detection optics
5 Fluid connections FIG. 29: Reaction cartridge according to Example 5.

FIG. 30: Recording of the reaction cartridge according to example 5 using a thermal imaging camera at a temperature of 95° C.

FIG. 31: Analysis of the reaction product according to example 5 using agarose gel electrophoresis. The reference numbers indicate:
1, 5: Positive control from the thermocycler
2-4: Reaction products from cartridges
6: 100 bp standard FIG. 32:
View exemplarily depicting the arrangement of the displacement structure.
1: second surface
2: first surface
3: displacement structure
4: solution
5: microarray FIG. 33: Analysis of the results of example 6, in which the hybridization results of a probe array during detection using the inventive method in a reaction chamber having a displacement structure are described.

The invention claimed is:

1. Device for the qualitative and/or quantitative detection of analytes,
   comprising:
   a) a micro array on a substrate, onto which probe molecules are immobilized on array elements, said microarray being disposed on a first surface of the device; and
   b) a detection chamber formed between the first surface including the micro array disposed thereon and a second surface,
   wherein the distance between the micro array and the second surface is variable, wherein the second surface has a displacement structure that is a bulge of the second surface and wherein the displacement structure, when viewed from the first surface, has a convex shape.

2. Device according to claim 1, wherein the displacement structure is located on the side of the second surface that is facing the microarray.

3. Device according to claim 2, wherein the displacement structure is located on the side of the second surface that is facing the micro array in such a way that, when a reaction chamber is in a compressed state, it is located at least partially opposite the surface of the micro array.

4. Device according to claim 1, wherein the detection chamber comprises at least two sub-chambers, wherein in a first non-compressed state the sub-chambers are in fluid connection, and in a second compressed state there is no fluid connection between the sub-chambers.

5. Device according to claim 4, wherein each sub-chamber is assigned to a defined area of the micro array.

6. Device according to claim 4, wherein the microarray and/or the second surface is/are provided with cavities acting as walls between the sub-chambers.

7. Device according to claim 4, wherein the walls between the sub-chambers are formed by elastic seals.

8. Device according to claim 1, wherein the device further comprises a filling unit and/or reprocessing unit for purifying and/or concentrating a sample solution and/or for controlling the charging and/or discharging of the reaction chamber with fluids.

* * * * *